(12) United States Patent
Olson et al.

(10) Patent No.: US 7,994,150 B2
(45) Date of Patent: Aug. 9, 2011

(54) MICRO-RNAS THAT MODULATE SMOOTH MUSCLE PROLIFERATION AND DIFFERENTIATION AND USES THEREOF

(75) Inventors: Eric Olson, Dallas, TX (US); Eric Small, Dallas, TX (US); Mei Xin, Dallas, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 67 days.

(21) Appl. No.: 12/391,028

(22) Filed: Feb. 23, 2009

(65) Prior Publication Data
US 2009/0226375 A1  Sep. 10, 2009

Related U.S. Application Data

(60) Provisional application No. 61/030,467, filed on Feb. 21, 2008.

(51) Int. Cl.
*C12N 15/11* (2006.01)
*A61K 48/00* (2006.01)
(52) U.S. Cl. .................................. 514/44 A; 514/44 R
(58) Field of Classification Search ............... 514/44 A, 514/44 R
See application file for complete search history.

(56) References Cited

U.S. PATENT DOCUMENTS
2009/0232893 A1* 9/2009 Bader et al. .................. 424/489

FOREIGN PATENT DOCUMENTS
WO  WO 03/029459 A2  4/2003
WO  WO 2009/137807 A3  11/2009

OTHER PUBLICATIONS
International Search Report and Written Opinion based on International Application PCT/US2009/034887 (Nov. 25, 2009).

* cited by examiner

*Primary Examiner* — Jon E Angell
(74) *Attorney, Agent, or Firm* — Cooley LLP

(57) ABSTRACT

The present invention relates to the identification of microRNAs that regulate smooth muscle cell proliferation and differentiation, including the miR-143/miR-145 cluster. Methods of treating restenosis and neointima formation by increasing expression of miR-143 and/or miR-145 are disclosed. The present invention also relates to the identification of two microRNAs, miR-486 and miR-422a, that regulate cell survival in the heart. Methods of treating or preventing cardiac hypertrophy, heart failure, or myocardial infarction by increasing expression of miR-486 and/or miR-422a in heart tissue are also disclosed.

37 Claims, 26 Drawing Sheets

A

| MicroRNA | control | ligated |
|---|---|---|
| hsa-miR-145 | 26,869 | 3,953 |
| hsa-miR-143 | 15,386 | 1,631 |
| hsa-miR-486 | 4,729 | 1,824 |
| hsa-miR-21 | 8,715 | 60,412 |

FIGURE 8A

Mouse Strain:          FVB

Number of mice:        10 mice per mimics group

Dose per mouse:        125 mg/kg/day x 2 days
                       (~ same cholesterol level in 125 mg of antagomirs)

Surgery procedure:     Left carotid artery ligation

Sham:                  Right unligated carotid artery

Mimics                 miR143 and miR145

Control for mimics     Saline

Samples to be collected   Heart, carotid arteries, lung, liver and kidney

Day 1          Day 2          Day 3          Day 31

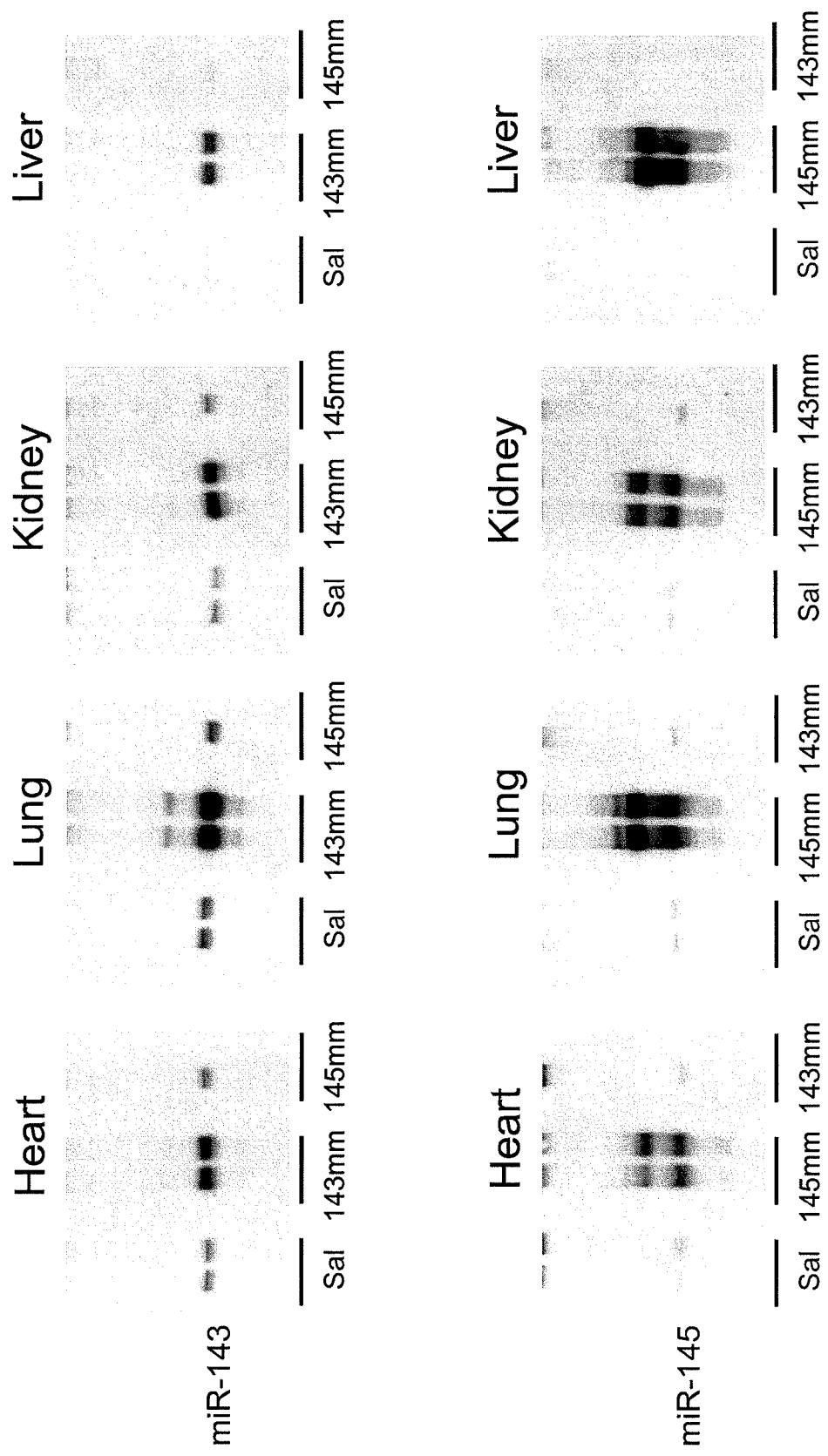

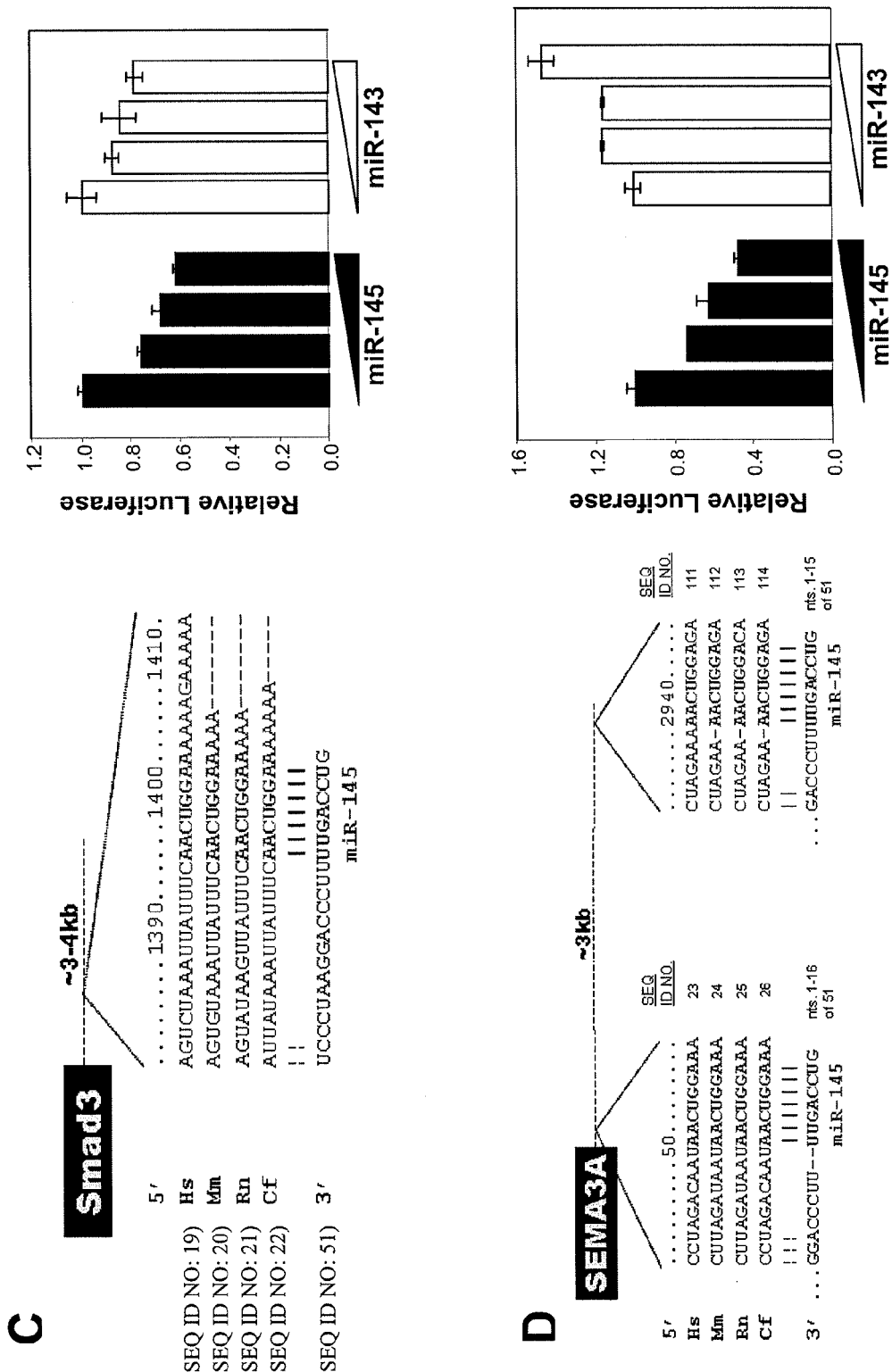
FIGURE 9C-D

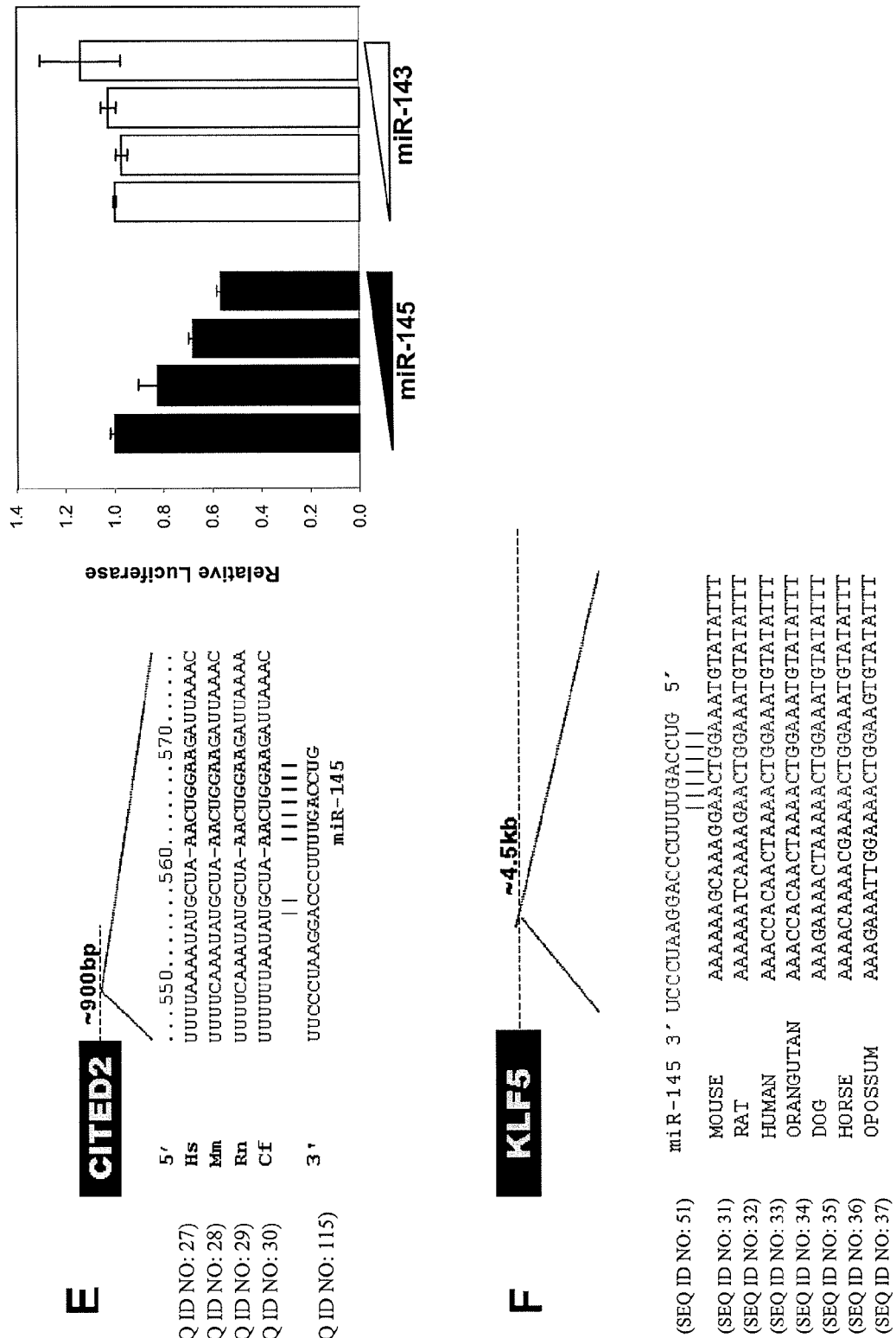
FIGURE 9E-F

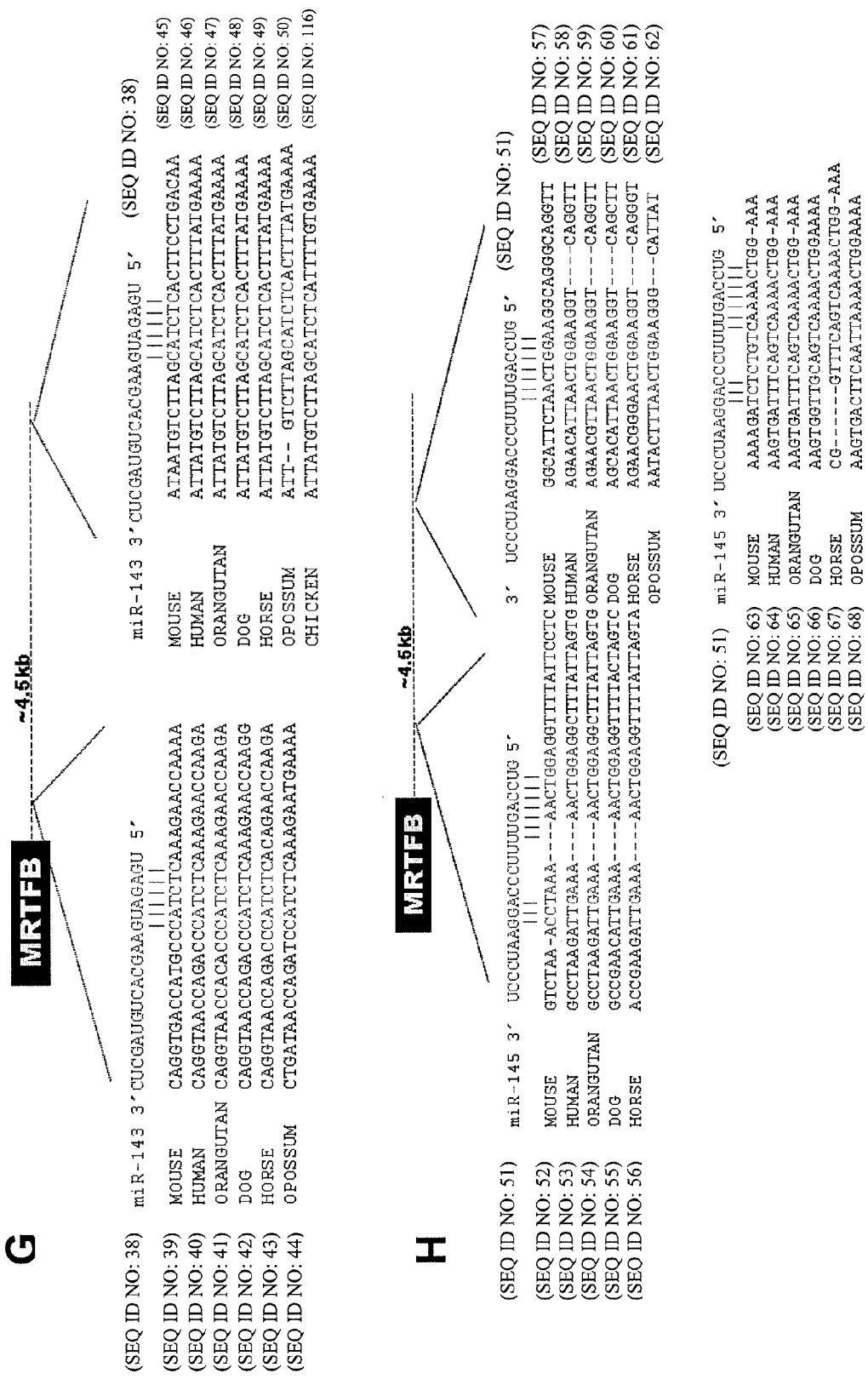
FIGURE 9G-H

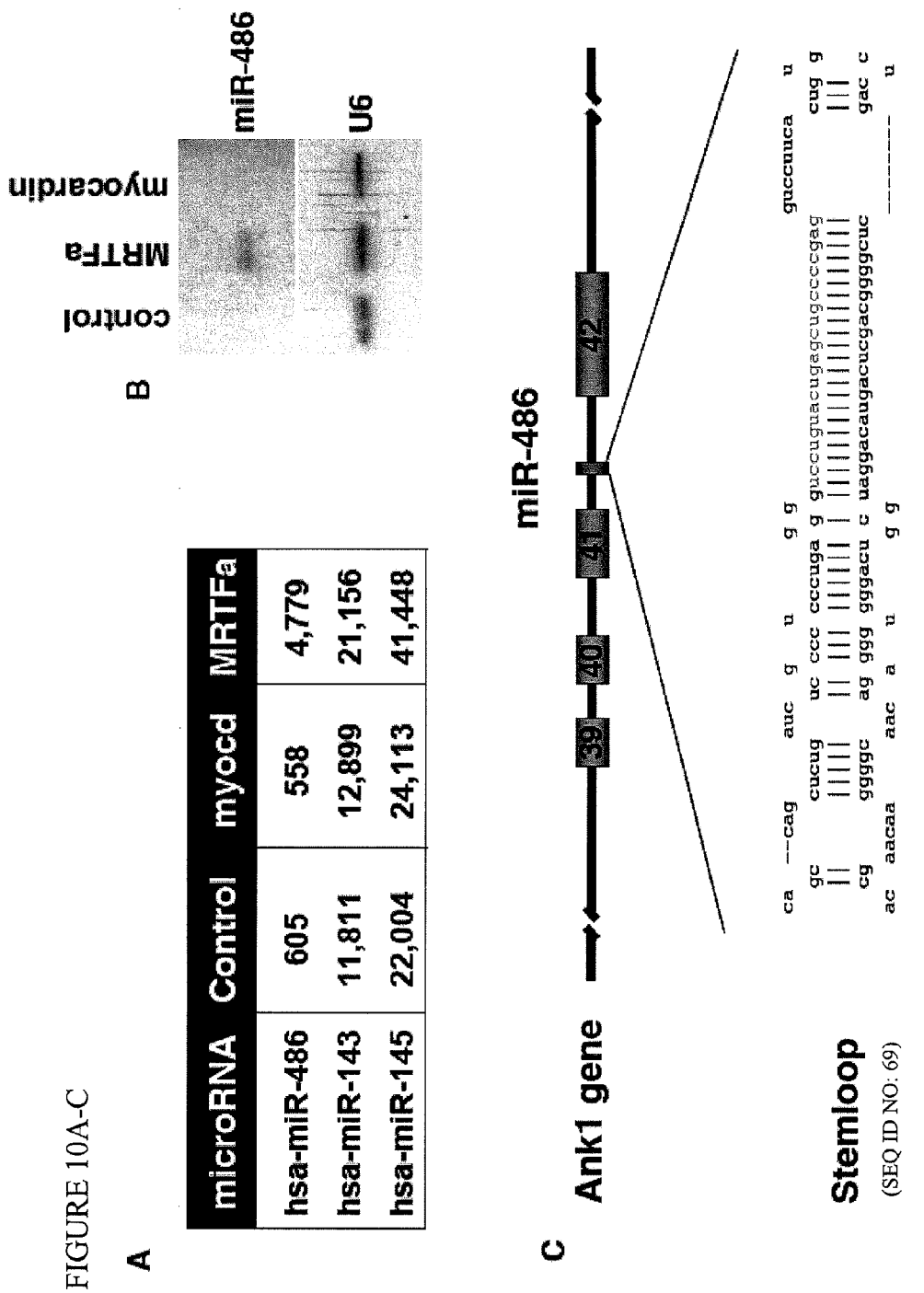
FIGURE 10A-C

FIGURE 10D-E
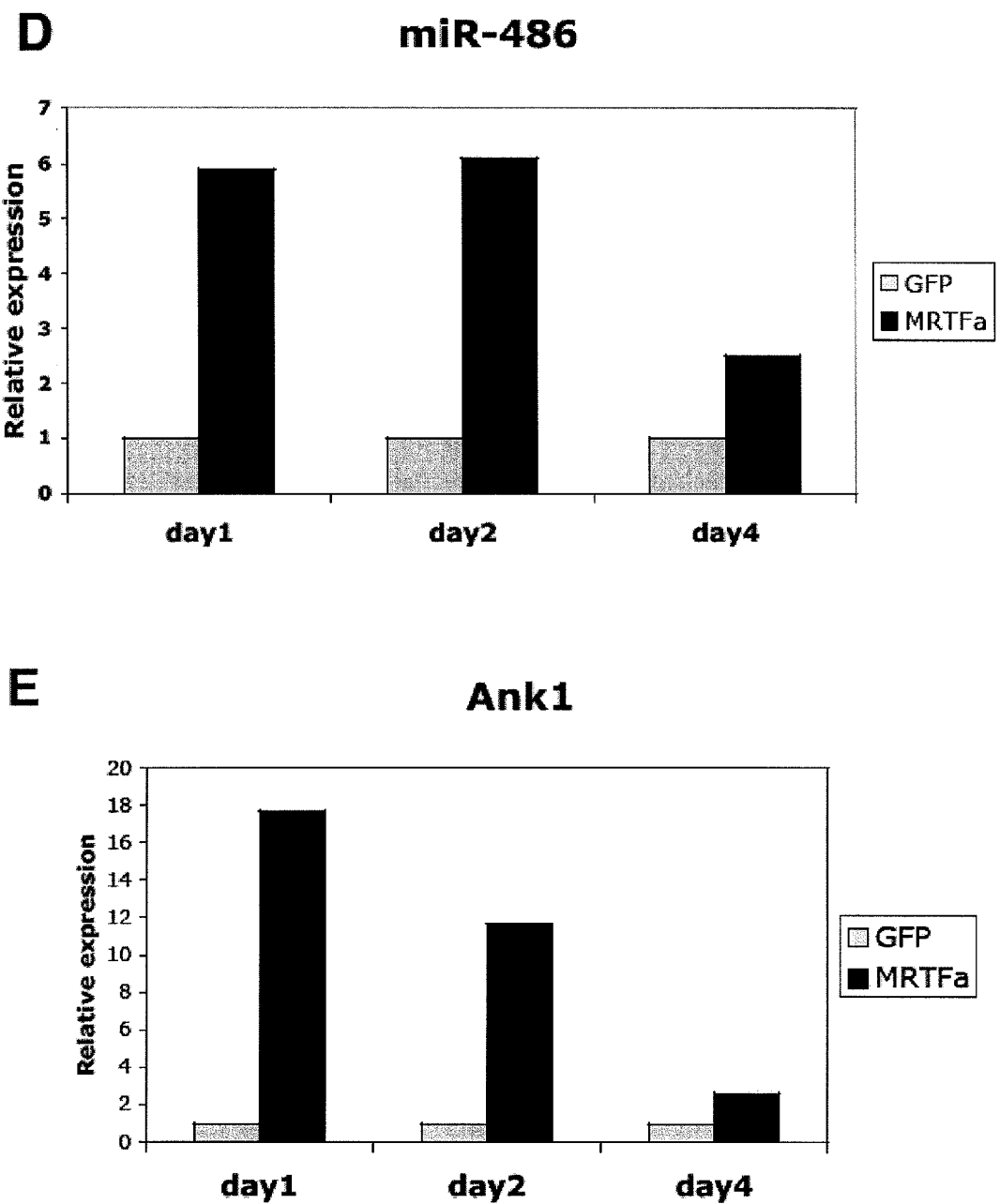

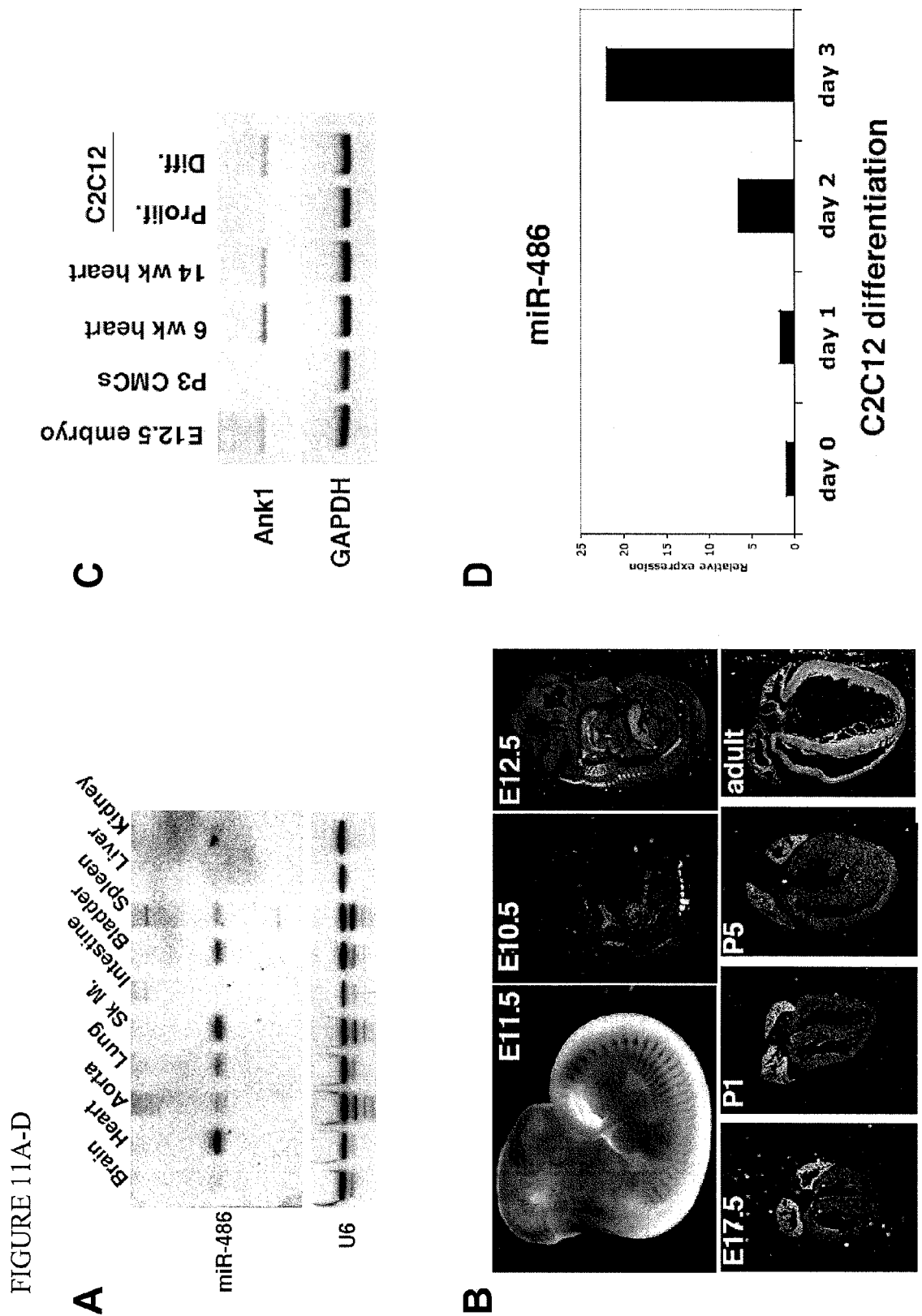
FIGURE 11A-D

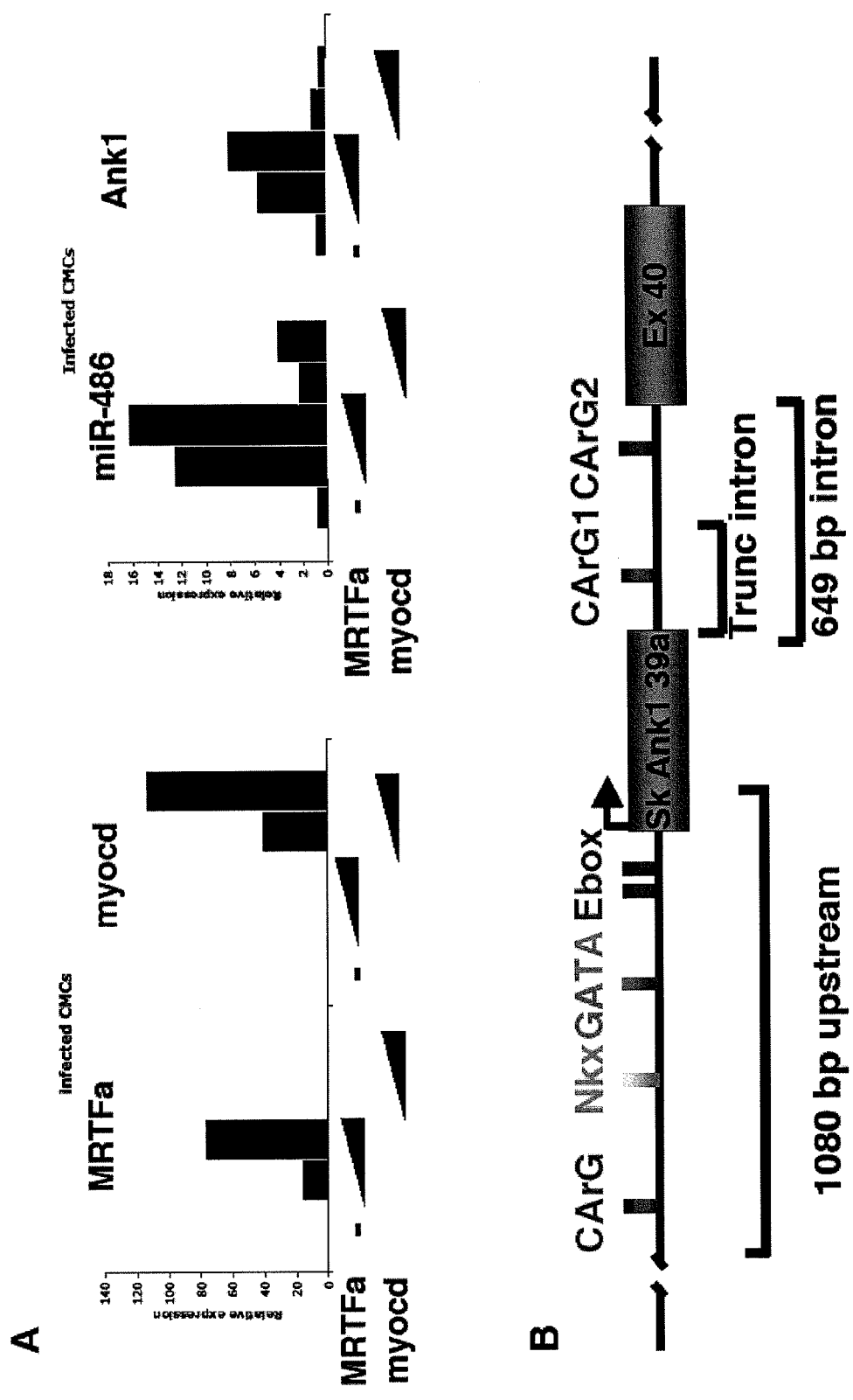
FIGURE 12A-B

FIGURE 12C-D
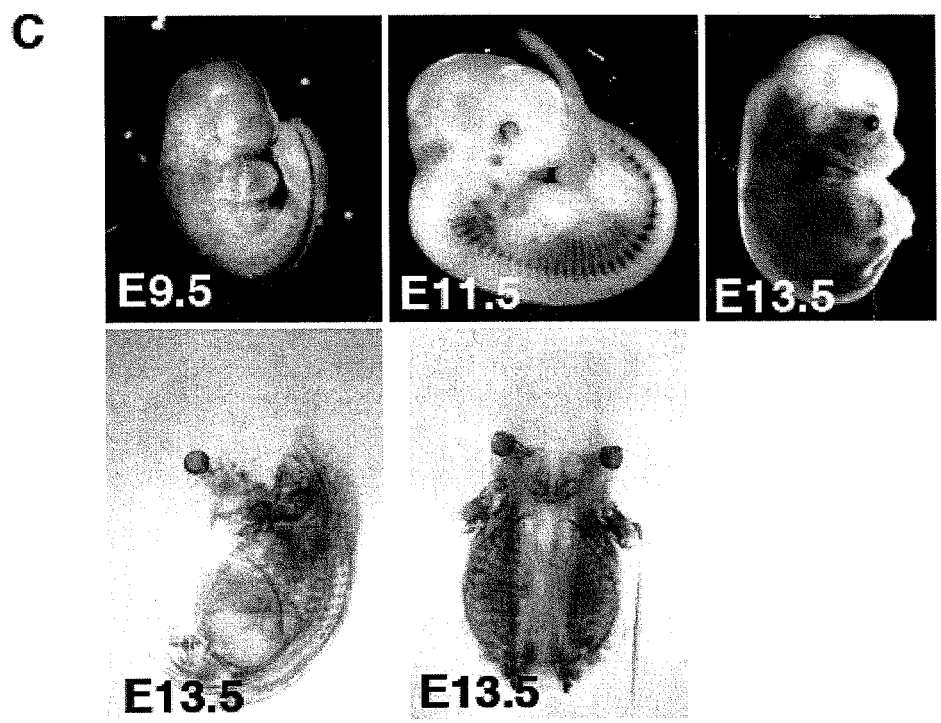
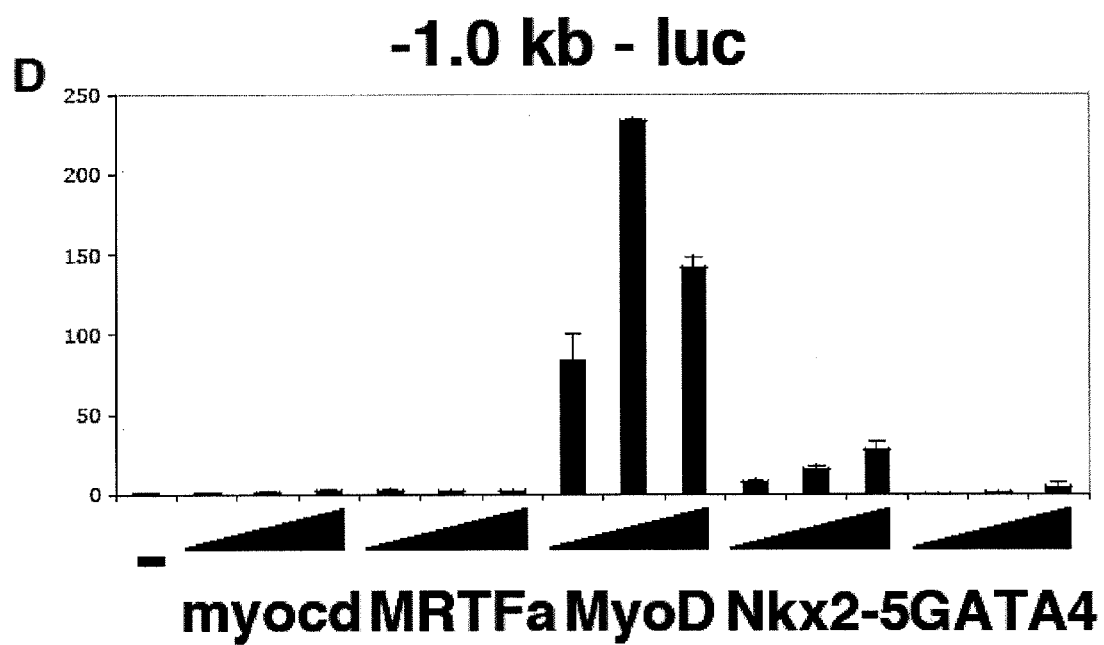

FIGURE 12E-G
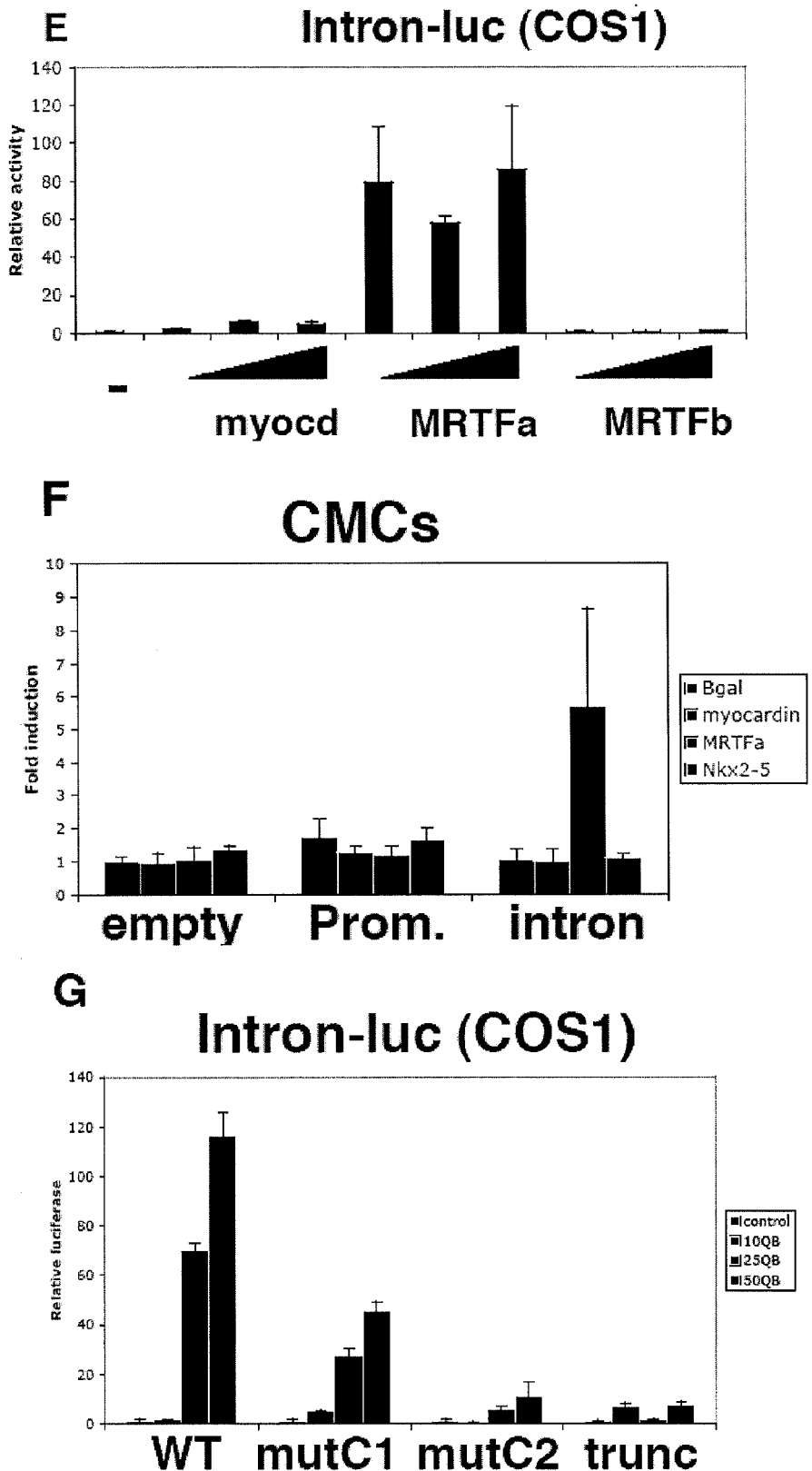

PTEN 3' UTR site 1 (8mer):

```
miR-486    3'- CAUGUCCU - 5'    (SEQ ID NO: 71)
                |||||||||
Hs    5' AUUGGGGUACAGGAAUGAACC 3'   (SEQ ID NO: 72)
Mm    5' AUUGGGGUACAGGAAUGAACC 3'   (SEQ ID NO: 73)
Rn    5' AUUGGGGUACAGGAAUGAACC 3'   (SEQ ID NO: 74)
Cf    5' AUUGGGGUACAGGAAUGAACC 3'   (SEQ ID NO: 75)
Gg    5' AUUGGGGUACAGGAAUGAACC 3'   (SEQ ID NO: 76)
```

PTEN 3' UTR site 2 (8mer):

```
miR-486    3'- CAUGUCCU - 5'    (SEQ ID NO: 71)
                |||||||||
Hs    5' AUGAUGUGUACAGGAUAAUGCC 3'   (SEQ ID NO: 77)
Mm    5' AUGACGUGUACAGGAUAAUGCC 3'   (SEQ ID NO: 78)
Rn    5' ACGACGUGUACAGGAUAAUGCC 3'   (SEQ ID NO: 79)
Cf    5' AUGAUGUGUACAGGAUAAUGCC 3'   (SEQ ID NO: 80)
Gg    5' AUGACAUGUACAGGAUAAUGCC 3'   (SEQ ID NO: 81)
```

FOXO1A 3' UTR (7mer):

```
miR-486    3'- CAUGUCCU - 5'    (SEQ ID NO: 71)
                |||||||
Hs    5' AUGAUGUGUACAGGUCUUUU 3'   (SEQ ID NO: 82)
Mm    5' AUGACGUGUACAGGUCUUUU 3'   (SEQ ID NO: 83)
Rn    5' ACGACGUGUACAGGUCUUUU 3'   (SEQ ID NO: 84)
Cf    5' AUGAUGUGUACAGGUCUUUU 3'   (SEQ ID NO: 85)
Gg    5' AUGACUUUGAUAAGUUUACC 3'   (SEQ ID NO: 86)
```

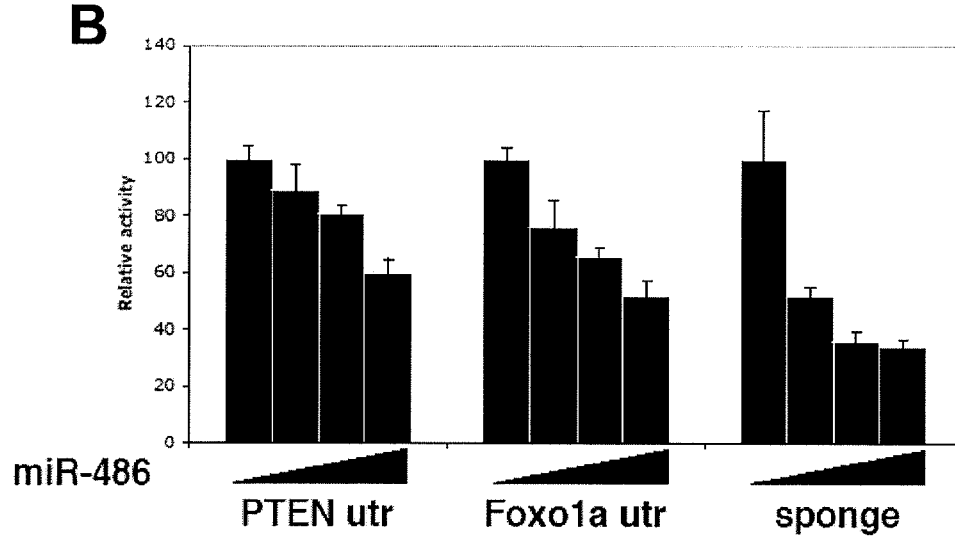

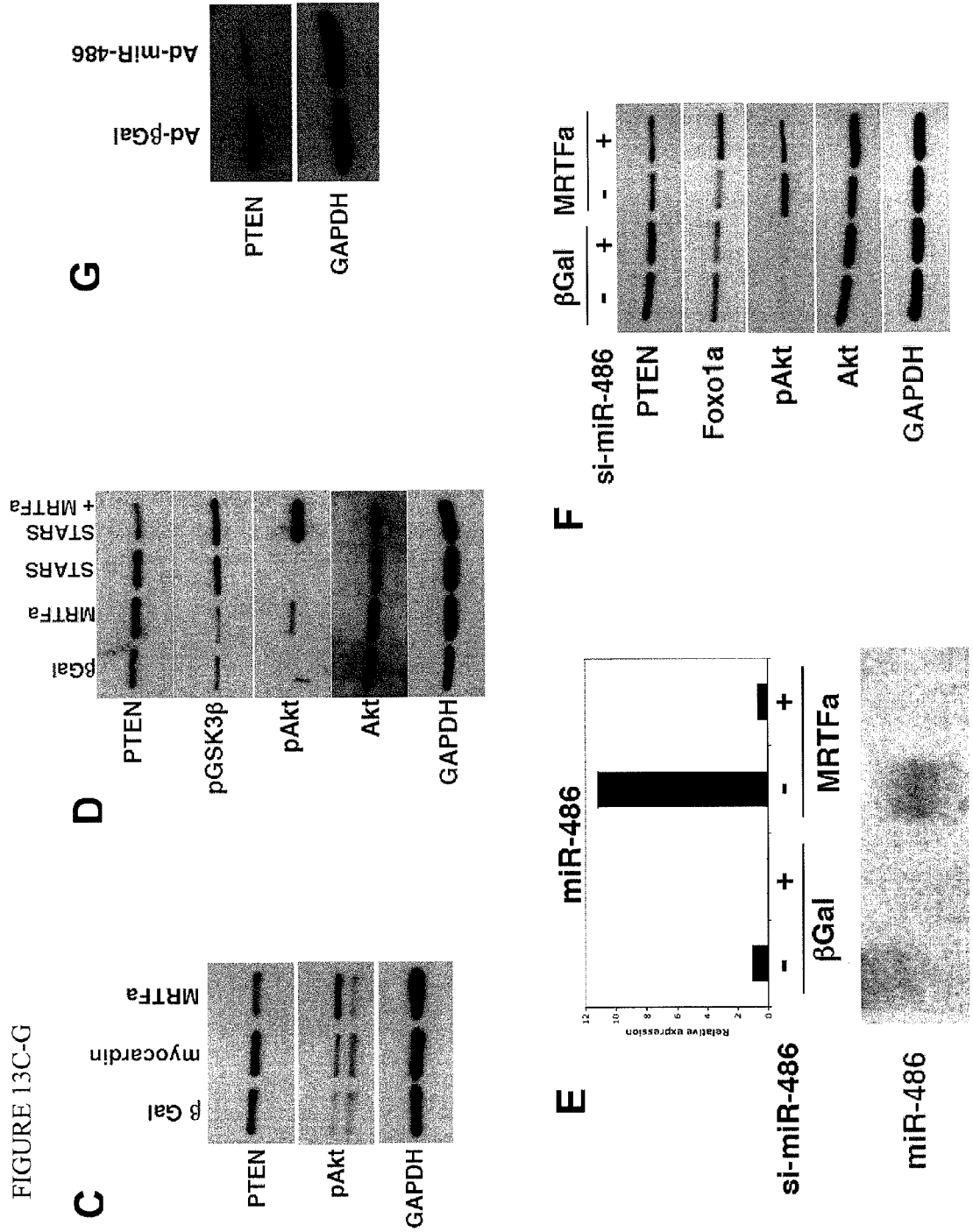
FIGURE 13C-G

FIGURE 14A-C
A
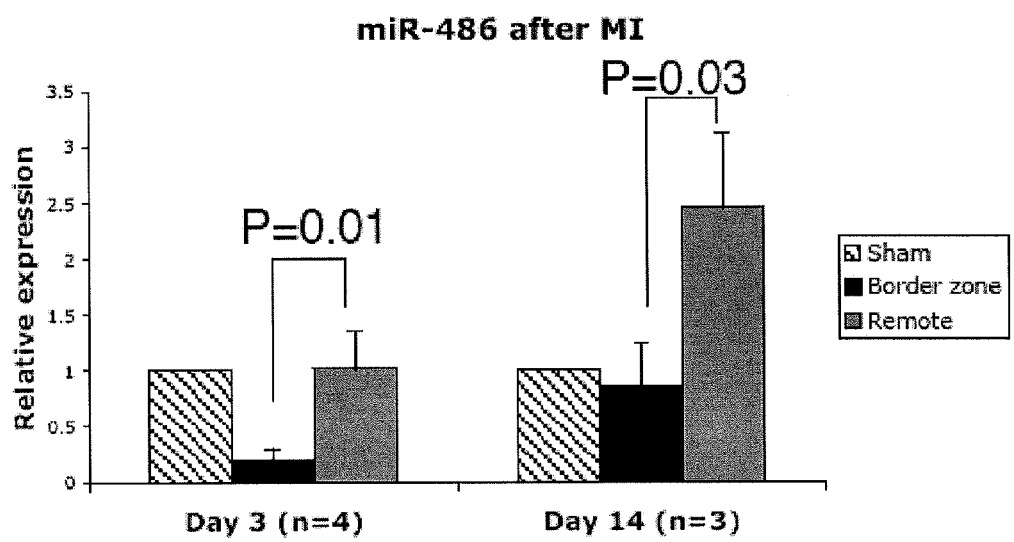
B
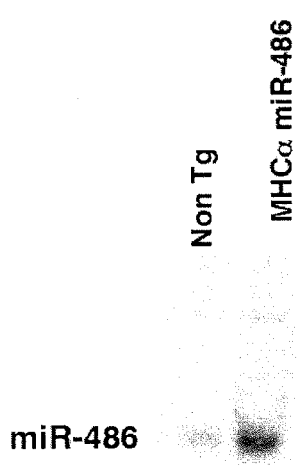
C
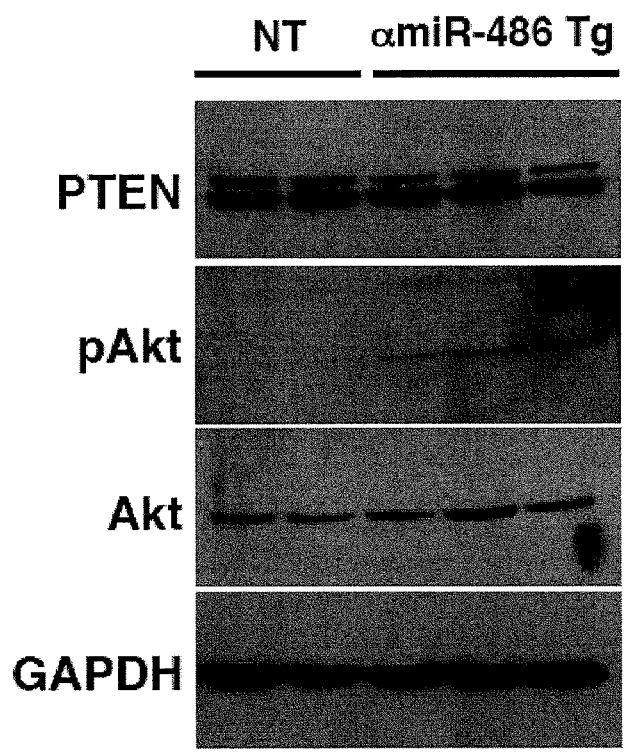

SEQUENCE LISTING

```
<160> NUMBER OF SEQ ID NOS: 116

<210> SEQ ID NO 1
<211> LENGTH: 33
<212> TYPE: DNA
<213> ORGANISM: Mus musculus

<400> SEQUENCE: 1
ggctcctgcc cttatatggc aaggctgctc tga                                33

<210> SEQ ID NO 2
<211> LENGTH: 33
<212> TYPE: DNA
<213> ORGANISM: Rattus norvegicus

<400> SEQUENCE: 2
ggctcctgtc cttatatggc aaggctgctc tga                                33

<210> SEQ ID NO 3
<211> LENGTH: 33
<212> TYPE: DNA
<213> ORGANISM: Homo sapiens

<400> SEQUENCE: 3
agctccttcc cttatatggc caggctgctc tgg                                33

<210> SEQ ID NO 4
<211> LENGTH: 33
<212> TYPE: DNA
```

-continued

<210> SEQ ID NO 4
<211> LENGTH: 33
<212> TYPE: DNA
<213> ORGANISM: Pongo sp.

<400> SEQUENCE: 4
ggctccttcc cttatatggc caggctgctc tgg          33

<210> SEQ ID NO 5
<211> LENGTH: 33
<212> TYPE: DNA
<213> ORGANISM: Canis familiaris

<400> SEQUENCE: 5
ggctccttcc cttatatggc caagccgctc cgg          33

<210> SEQ ID NO 6
<211> LENGTH: 33
<212> TYPE: DNA
<213> ORGANISM: Equus caballus

<400> SEQUENCE: 6
ggctccttcc cttatatggc caggccgctc tgg          33

<210> SEQ ID NO 7
<211> LENGTH: 33
<212> TYPE: DNA
<213> ORGANISM: Didelphis sp.

<400> SEQUENCE: 7
tgttccttcc cttatatggc tatgtaggtc caa          33

<210> SEQ ID NO 8
<211> LENGTH: 10
<212> TYPE: DNA
<213> ORGANISM: Artificial Sequence
<220> FEATURE:
<223> OTHER INFORMATION: Mutant serum response factor (SRF) binding
      site

<400> SEQUENCE: 8
ccttatattt          10

<210> SEQ ID NO 9
<211> LENGTH: 24
<212> TYPE: DNA
<213> ORGANISM: Unknown
<220> FEATURE:
<223> OTHER INFORMATION: Conserved serum response factor (SRF) binding
      site

<400> SEQUENCE: 9
gggccttgcc atataagggc agga          24

<210> SEQ ID NO 10
<211> LENGTH: 24
<212> TYPE: DNA
<213> ORGANISM: Unknown
<220> FEATURE:
<223> OTHER INFORMATION: Conserved serum response factor (SRF) binding
      site

<400> SEQUENCE: 10
ggtcctgccc ttatatggca aggc          24

<210> SEQ ID NO 11
<211> LENGTH: 17
<212> TYPE: RNA
<213> ORGANISM: Homo sapiens

```
<400> SEQUENCE: 11
gugcuuauaa cuggaga                                              17

<210> SEQ ID NO 12
<211> LENGTH: 17
<212> TYPE: RNA
<213> ORGANISM: Mus musculus

<400> SEQUENCE: 12
gcgcuuauaa cuggaga                                              17

<210> SEQ ID NO 13
<211> LENGTH: 17
<212> TYPE: RNA
<213> ORGANISM: Rattus norvegicus

<400> SEQUENCE: 13
gcccuuauaa cuggaga                                              17

<210> SEQ ID NO 14
<211> LENGTH: 17
<212> TYPE: RNA
<213> ORGANISM: Canis familiaris

<400> SEQUENCE: 14
gugcuuauaa cuggaga                                              17

<210> SEQ ID NO 15
<211> LENGTH: 23
<212> TYPE: RNA
<213> ORGANISM: Homo sapiens

<400> SEQUENCE: 15
gcucacugca aacaacugga auu                                       23

<210> SEQ ID NO 16
<211> LENGTH: 19
<212> TYPE: RNA
<213> ORGANISM: Mus musculus

<400> SEQUENCE: 16
gcucacuuca acuggaauu                                            19

<210> SEQ ID NO 17
<211> LENGTH: 19
<212> TYPE: RNA
<213> ORGANISM: Rattus norvegicus

<400> SEQUENCE: 17
gcucacuuca acuggaauu                                            19

<210> SEQ ID NO 18
<211> LENGTH: 22
<212> TYPE: RNA
<213> ORGANISM: Canis familiaris

<400> SEQUENCE: 18
gcuccugcag ucaacuggaa uu                                        22

<210> SEQ ID NO 19
<211> LENGTH: 33
<212> TYPE: RNA
<213> ORGANISM: Homo sapiens
```

```
<400> SEQUENCE: 19
agucuaaauu auucaacug gaaaaagaa aaa                              33

<210> SEQ ID NO 20
<211> LENGTH: 26
<212> TYPE: RNA
<213> ORGANISM: Mus musculus

<400> SEQUENCE: 20
aguguaaauu auucaacug gaaaaa                                     26

<210> SEQ ID NO 21
<211> LENGTH: 26
<212> TYPE: RNA
<213> ORGANISM: Rattus norvegicus

<400> SEQUENCE: 21
aguauaaguu auucaacug gaaaaa                                     26

<210> SEQ ID NO 22
<211> LENGTH: 28
<212> TYPE: RNA
<213> ORGANISM: Canis familiaris

<400> SEQUENCE: 22
auuauaaauu auucaacug gaaaaaaa                                   28

<210> SEQ ID NO 23
<211> LENGTH: 19
<212> TYPE: RNA
<213> ORGANISM: Homo sapiens

<400> SEQUENCE: 23
ccuagacaau aacuggaaa                                            19

<210> SEQ ID NO 24
<211> LENGTH: 19
<212> TYPE: RNA
<213> ORGANISM: Mus musculus

<400> SEQUENCE: 24
cuuagauaau aacuggaaa                                            19

<210> SEQ ID NO 25
<211> LENGTH: 19
<212> TYPE: RNA
<213> ORGANISM: Rattus norvegicus

<400> SEQUENCE: 25
cuuagauaau aacuggaaa                                            19

<210> SEQ ID NO 26
<211> LENGTH: 19
<212> TYPE: RNA
<213> ORGANISM: Canis familiaris

<400> SEQUENCE: 26
ccuagacaau aacuggaaa                                            19

<210> SEQ ID NO 27
<211> LENGTH: 31
<212> TYPE: RNA
<213> ORGANISM: Homo sapiens
```

```
<400> SEQUENCE: 27
uuuuaaaaua ugcuaaacug gaagauuaaa c                              31

<210> SEQ ID NO 28
<211> LENGTH: 31
<212> TYPE: RNA
<213> ORGANISM: Mus musculus

<400> SEQUENCE: 28
uuuucaaaua ugcuaaacug gaagauuaaa c                              31

<210> SEQ ID NO 29
<211> LENGTH: 31
<212> TYPE: RNA
<213> ORGANISM: Rattus norvegicus

<400> SEQUENCE: 29
uuuucaaaua ugcuaaacug gaagauuaaa a                              31

<210> SEQ ID NO 30
<211> LENGTH: 31
<212> TYPE: RNA
<213> ORGANISM: Canis familiaris

<400> SEQUENCE: 30
uuuuuuaaua ugcuaaacug gaagauuaaa c                              31

<210> SEQ ID NO 31
<211> LENGTH: 31
<212> TYPE: DNA
<213> ORGANISM: Mus musculus

<400> SEQUENCE: 31
aaaaaagcaa aggaactgga aatgtatatt t                              31

<210> SEQ ID NO 32
<211> LENGTH: 31
<212> TYPE: DNA
<213> ORGANISM: Rattus norvegicus

<400> SEQUENCE: 32
aaaaaatcaa aagaactgga aatgtatatt t                              31

<210> SEQ ID NO 33
<211> LENGTH: 31
<212> TYPE: DNA
<213> ORGANISM: Homo sapiens

<400> SEQUENCE: 33
aaaccacaac taaaactgga aatgtatatt t                              31

<210> SEQ ID NO 34
<211> LENGTH: 31
<212> TYPE: DNA
<213> ORGANISM: Pongo sp.

<400> SEQUENCE: 34
aaaccacaac taaaactgga aatgtatatt t                              31

<210> SEQ ID NO 35
<211> LENGTH: 31
<212> TYPE: DNA
<213> ORGANISM: Canis familiaris
```

```
<400> SEQUENCE: 35
aaagaaaact aaaaactgga aatgtatatt t                              31

<210> SEQ ID NO 36
<211> LENGTH: 31
<212> TYPE: DNA
<213> ORGANISM: Equus caballus

<400> SEQUENCE: 36
aaaacaaaac gaaaactgga aatgtatatt t                              31

<210> SEQ ID NO 37
<211> LENGTH: 31
<212> TYPE: DNA
<213> ORGANISM: Didelphis sp.

<400> SEQUENCE: 37
aaagaaattg gaaaactgga agtgtatatt t                              31

<210> SEQ ID NO 38
<211> LENGTH: 21
<212> TYPE: RNA
<213> ORGANISM: Homo sapiens

<400> SEQUENCE: 38
ugagaugaag cacuguagcu c                                         21

<210> SEQ ID NO 39
<211> LENGTH: 32
<212> TYPE: DNA
<213> ORGANISM: Mus musculus

<400> SEQUENCE: 39
caggtgacca tgcccatctc aaagaaccaa aa                             32

<210> SEQ ID NO 40
<211> LENGTH: 32
<212> TYPE: DNA
<213> ORGANISM: Homo sapiens

<400> SEQUENCE: 40
caggtaacca gacccatctc aaagaaccaa ga                             32

<210> SEQ ID NO 41
<211> LENGTH: 32
<212> TYPE: DNA
<213> ORGANISM: Pongo sp.

<400> SEQUENCE: 41
caggtaacca cacccatctc aaagaaccaa ga                             32

<210> SEQ ID NO 42
<211> LENGTH: 32
<212> TYPE: DNA
<213> ORGANISM: Canis familiaris

<400> SEQUENCE: 42
caggtaacca gacccatctc aaagaaccaa gg                             32

<210> SEQ ID NO 43
<211> LENGTH: 32
<212> TYPE: DNA
<213> ORGANISM: Equus caballus
```

```
<400> SEQUENCE: 43
caggtaacca gacccatctc acagaaccaa ga                                32

<210> SEQ ID NO 44
<211> LENGTH: 32
<212> TYPE: DNA
<213> ORGANISM: Didelphis sp.

<400> SEQUENCE: 44
ctgataacca gatccatctc aaagaatgaa aa                                32

<210> SEQ ID NO 45
<211> LENGTH: 30
<212> TYPE: DNA
<213> ORGANISM: Mus musculus

<400> SEQUENCE: 45
ataatgtctt agcatctcac ttcctgacaa                                   30

<210> SEQ ID NO 46
<211> LENGTH: 30
<212> TYPE: DNA
<213> ORGANISM: Homo sapiens

<400> SEQUENCE: 46
attatgtctt agcatctcac tttatgaaaa                                   30

<210> SEQ ID NO 47
<211> LENGTH: 30
<212> TYPE: DNA
<213> ORGANISM: Pongo sp.

<400> SEQUENCE: 47
attatgtctt agcatctcac tttatgaaaa                                   30

<210> SEQ ID NO 48
<211> LENGTH: 30
<212> TYPE: DNA
<213> ORGANISM: Canis familiaris

<400> SEQUENCE: 48
attatgtctt agcatctcac tttatgaaaa                                   30

<210> SEQ ID NO 49
<211> LENGTH: 30
<212> TYPE: DNA
<213> ORGANISM: Equus caballus

<400> SEQUENCE: 49
attatgtctt agcatctcac tttatgaaaa                                   30

<210> SEQ ID NO 50
<211> LENGTH: 28
<212> TYPE: DNA
<213> ORGANISM: Didelphis sp.

<400> SEQUENCE: 50
attgtcttag catctcactt tatgaaaa                                     28

<210> SEQ ID NO 51
<211> LENGTH: 23
<212> TYPE: RNA
<213> ORGANISM: Homo sapiens
```

```
<400> SEQUENCE: 51
guccaguuuu cccaggaauc ccu                                          23

<210> SEQ ID NO 52
<211> LENGTH: 33
<212> TYPE: DNA
<213> ORGANISM: Mus musculus

<400> SEQUENCE: 52
gtctaaacct aaaaactgga ggttttattc ctc                               33

<210> SEQ ID NO 53
<211> LENGTH: 34
<212> TYPE: DNA
<213> ORGANISM: Homo sapiens

<400> SEQUENCE: 53
gcctaagatt gaaaaactgg aggctttatt agtg                              34

<210> SEQ ID NO 54
<211> LENGTH: 34
<212> TYPE: DNA
<213> ORGANISM: Pongo sp.

<400> SEQUENCE: 54
gcctaagatt gaaaaactgg aggctttatt agtg                              34

<210> SEQ ID NO 55
<211> LENGTH: 34
<212> TYPE: DNA
<213> ORGANISM: Canis familiaris

<400> SEQUENCE: 55
gccgaacatt gaaaaactgg aggttttact agtc                              34

<210> SEQ ID NO 56
<211> LENGTH: 34
<212> TYPE: DNA
<213> ORGANISM: Equus caballus

<400> SEQUENCE: 56
accgaagatt gaaaaactgg aggttttatt agta                              34

<210> SEQ ID NO 57
<211> LENGTH: 29
<212> TYPE: DNA
<213> ORGANISM: Mus musculus

<400> SEQUENCE: 57
ggcattctaa ctggaaggca gggcaggtt                                    29

<210> SEQ ID NO 58
<211> LENGTH: 25
<212> TYPE: DNA
<213> ORGANISM: Homo sapiens

<400> SEQUENCE: 58
agaacattaa ctggaaggtc aggtt                                        25

<210> SEQ ID NO 59
<211> LENGTH: 25
<212> TYPE: DNA
<213> ORGANISM: Pongo sp.
```

```
<400> SEQUENCE: 59
agaacgttaa ctggaaggtc aggtt                                              25

<210> SEQ ID NO 60
<211> LENGTH: 25
<212> TYPE: DNA
<213> ORGANISM: Canis familiaris

<400> SEQUENCE: 60
agcacattaa ctggaaggtc agctt                                              25

<210> SEQ ID NO 61
<211> LENGTH: 25
<212> TYPE: DNA
<213> ORGANISM: Equus caballus

<400> SEQUENCE: 61
agaacgggaa ctggaaggtc agggt                                              25

<210> SEQ ID NO 62
<211> LENGTH: 25
<212> TYPE: DNA
<213> ORGANISM: Didelphis sp.

<400> SEQUENCE: 62
aatactttaa ctggaagggc attat                                              25

<210> SEQ ID NO 63
<211> LENGTH: 25
<212> TYPE: DNA
<213> ORGANISM: Mus musculus

<400> SEQUENCE: 63
aaaagatctc tgtcaaaact ggaaa                                              25

<210> SEQ ID NO 64
<211> LENGTH: 25
<212> TYPE: DNA
<213> ORGANISM: Homo sapiens

<400> SEQUENCE: 64
aagtgatttc agtcaaaact ggaaa                                              25

<210> SEQ ID NO 65
<211> LENGTH: 25
<212> TYPE: DNA
<213> ORGANISM: Pongo sp.

<400> SEQUENCE: 65
aagtgatttc agtcaaaact ggaaa                                              25

<210> SEQ ID NO 66
<211> LENGTH: 26
<212> TYPE: DNA
<213> ORGANISM: Canis familiaris

<400> SEQUENCE: 66
aagtggttgc agtcaaaact ggaaaa                                             26

<210> SEQ ID NO 67
<211> LENGTH: 22
<212> TYPE: DNA
<213> ORGANISM: Equus caballus
```

```
<400> SEQUENCE: 67
cggtttcagt caaaactgga aa                                              22

<210> SEQ ID NO 68
<211> LENGTH: 26
<212> TYPE: DNA
<213> ORGANISM: Pongo sp.

<400> SEQUENCE: 68
aagtgacttc aattaaaact ggaaaa                                          26

<210> SEQ ID NO 69
<211> LENGTH: 128
<212> TYPE: RNA
<213> ORGANISM: Homo sapiens

<400> SEQUENCE: 69
cagccagcuc ugaucucgcc cucccugagg gguccuguac ugagcugccc cgagguccuu     60
cacugugcuc agcucggggc agcucaguac aggaugcguc aggugggag acaacgggga    120 acaagcca                                                            128

<210> SEQ ID NO 70
<211> LENGTH: 22
<212> TYPE: RNA
<213> ORGANISM: Homo sapiens

<400> SEQUENCE: 70
uccuguacug agcugccccg ag                                              22

<210> SEQ ID NO 71
<211> LENGTH: 8
<212> TYPE: RNA
<213> ORGANISM: Homo sapiens

<400> SEQUENCE: 71 cauguccu                                                               8

<210> SEQ ID NO 72
<211> LENGTH: 21
<212> TYPE: RNA
<213> ORGANISM: Homo sapiens

<400> SEQUENCE: 72 auuggguac aggaaugaac c                                                21

<210> SEQ ID NO 73
<211> LENGTH: 21
<212> TYPE: RNA
<213> ORGANISM: Mus musculus

<400> SEQUENCE: 73 auuggguac aggaaugaac c                                                21

<210> SEQ ID NO 74
<211> LENGTH: 21
<212> TYPE: RNA
<213> ORGANISM: Rattus norvegicus

<400> SEQUENCE: 74 auuggguac aggaaugaac c                                                21
```

-continued

```
<210> SEQ ID NO 75
<211> LENGTH: 21
<212> TYPE: RNA
<213> ORGANISM: Canis familiaris

<400> SEQUENCE: 75 auuggggguac aggaaugaac c                                              21

<210> SEQ ID NO 76
<211> LENGTH: 21
<212> TYPE: RNA
<213> ORGANISM: Gallus gallus

<400> SEQUENCE: 76
auugggguac aggaaugaac c                                               21

<210> SEQ ID NO 77
<211> LENGTH: 22
<212> TYPE: RNA
<213> ORGANISM: Homo sapiens

<400> SEQUENCE: 77
augaugugua caggauaaug cc                                              22

<210> SEQ ID NO 78
<211> LENGTH: 22
<212> TYPE: RNA
<213> ORGANISM: Mus musculus

<400> SEQUENCE: 78
augacgugua caggauaaug cc                                              22

<210> SEQ ID NO 79
<211> LENGTH: 22
<212> TYPE: RNA
<213> ORGANISM: Rattus norvegicus

<400> SEQUENCE: 79
acgacgugua caggauaaug cc                                              22

<210> SEQ ID NO 80
<211> LENGTH: 22
<212> TYPE: RNA
<213> ORGANISM: Canis familiaris

<400> SEQUENCE: 80
augaugugua caggauaaug cc                                              22

<210> SEQ ID NO 81
<211> LENGTH: 22
<212> TYPE: RNA
<213> ORGANISM: Gallus gallus

<400> SEQUENCE: 81
augacaugua caggauaaug cc                                              22

<210> SEQ ID NO 82
<211> LENGTH: 20
<212> TYPE: RNA
<213> ORGANISM: Homo sapiens

<400> SEQUENCE: 82
augaugugua caggucuuuu                                                 20
```

```
<210> SEQ ID NO 83
<211> LENGTH: 20
<212> TYPE: RNA
<213> ORGANISM: Mus musculus

<400> SEQUENCE: 83
augacgugua caggucuuuu                                                     20

<210> SEQ ID NO 84
<211> LENGTH: 20
<212> TYPE: RNA
<213> ORGANISM: Rattus norvegicus

<400> SEQUENCE: 84
acgacgugua caggucuuuu                                                     20

<210> SEQ ID NO 85
<211> LENGTH: 20
<212> TYPE: RNA
<213> ORGANISM: Canis familiaris

<400> SEQUENCE: 85
augaugugua caggucuuuu                                                     20

<210> SEQ ID NO 86
<211> LENGTH: 20
<212> TYPE: RNA
<213> ORGANISM: Gallus gallus

<400> SEQUENCE: 86
augacuuuga uaaguuuacc                                                     20

<210> SEQ ID NO 87
<211> LENGTH: 21
<212> TYPE: DNA
<213> ORGANISM: Mus musculus

<400> SEQUENCE: 87
ggcaatagga cattgtgtca g                                                   21

<210> SEQ ID NO 88
<211> LENGTH: 21
<212> TYPE: DNA
<213> ORGANISM: Mus musculus

<400> SEQUENCE: 88
tgacaagaat gagactttaa t                                                   21

<210> SEQ ID NO 89
<211> LENGTH: 21
<212> TYPE: DNA
<213> ORGANISM: Mus musculus

<400> SEQUENCE: 89
gttagtgagc aggctacatt t                                                   21

<210> SEQ ID NO 90
<211> LENGTH: 21
<212> TYPE: DNA
<213> ORGANISM: Mus musculus

<400> SEQUENCE: 90
aagacttggt gctatgcgct g                                                   21
```

-continued

<210> SEQ ID NO 91
<211> LENGTH: 22
<212> TYPE: RNA
<213> ORGANISM: Homo sapiens

<400> SEQUENCE: 91
ggugcagugc ugcaucucug gu                                              22

<210> SEQ ID NO 92
<211> LENGTH: 22
<212> TYPE: RNA
<213> ORGANISM: Homo sapiens

<400> SEQUENCE: 92
ggauuccugg aaauacuguu cu                                              22

<210> SEQ ID NO 93
<211> LENGTH: 21
<212> TYPE: RNA
<213> ORGANISM: Homo sapiens

<400> SEQUENCE: 93
cggggcagcu caguacagga u                                               21

<210> SEQ ID NO 94
<211> LENGTH: 22
<212> TYPE: RNA
<213> ORGANISM: Homo sapiens

<400> SEQUENCE: 94
acuggacuua gggucagaag gc                                              22

<210> SEQ ID NO 95
<211> LENGTH: 22
<212> TYPE: RNA
<213> ORGANISM: Homo sapiens

<400> SEQUENCE: 95
aauuuuuuua aauaacugga ca                                              22

<210> SEQ ID NO 96
<211> LENGTH: 22
<212> TYPE: RNA
<213> ORGANISM: Mus musculus

<400> SEQUENCE: 96
aauuuuuuuu aauaacugga ca                                              22

<210> SEQ ID NO 97
<211> LENGTH: 21
<212> TYPE: RNA
<213> ORGANISM: Rattus norvegicus

<400> SEQUENCE: 97
aauuuuuuua auaacuggac a                                               21

<210> SEQ ID NO 98
<211> LENGTH: 35
<212> TYPE: RNA
<213> ORGANISM: Canis familiaris

<400> SEQUENCE: 98
aauuuuuuuu cuuuuuuuuu uuuaauaacu ggaca                                35

```
<210> SEQ ID NO 99
<211> LENGTH: 18
<212> TYPE: RNA
<213> ORGANISM: Homo sapiens

<400> SEQUENCE: 99
gcagccugua aacuggaa                                                 18

<210> SEQ ID NO 100
<211> LENGTH: 18
<212> TYPE: RNA
<213> ORGANISM: Mus musculus

<400> SEQUENCE: 100
gcagcuuaga aacuggaa                                                 18

<210> SEQ ID NO 101
<211> LENGTH: 18
<212> TYPE: RNA
<213> ORGANISM: Rattus norvegicus

<400> SEQUENCE: 101
gcagcuuaua aacuggaa                                                 18

<210> SEQ ID NO 102
<211> LENGTH: 18
<212> TYPE: RNA
<213> ORGANISM: Canis familiaris

<400> SEQUENCE: 102
gcagccugua aacuggaa                                                 18

<210> SEQ ID NO 103
<211> LENGTH: 23
<212> TYPE: RNA
<213> ORGANISM: Homo sapiens

<400> SEQUENCE: 103
cgggaugcgc agagcacugg aag                                           23

<210> SEQ ID NO 104
<211> LENGTH: 23
<212> TYPE: RNA
<213> ORGANISM: Mus musculus

<400> SEQUENCE: 104
caggaugaac agaccacugg aag                                           23

<210> SEQ ID NO 105
<211> LENGTH: 27
<212> TYPE: RNA
<213> ORGANISM: Rattus norvegicus

<400> SEQUENCE: 105
caggaugaac agacagacca cuggaag                                       27

<210> SEQ ID NO 106
<211> LENGTH: 23
<212> TYPE: RNA
<213> ORGANISM: Canis familiaris

<400> SEQUENCE: 106
caggaugaac agaccacugg aag                                           23
```

```
<210> SEQ ID NO 107
<211> LENGTH: 21
<212> TYPE: RNA
<213> ORGANISM: Homo sapiens

<400> SEQUENCE: 107
uaguguugau aacuggaaua u                                              21

<210> SEQ ID NO 108
<211> LENGTH: 21
<212> TYPE: RNA
<213> ORGANISM: Mus musculus

<400> SEQUENCE: 108
uaguguugau aacuggaaua u                                              21

<210> SEQ ID NO 109
<211> LENGTH: 21
<212> TYPE: RNA
<213> ORGANISM: Rattus norvegicus

<400> SEQUENCE: 109
uaguguugau aacuggaaua u                                              21

<210> SEQ ID NO 110
<211> LENGTH: 21
<212> TYPE: RNA
<213> ORGANISM: Canis familiaris

<400> SEQUENCE: 110
uaguguugau aacuggaaua u                                              21

<210> SEQ ID NO 111
<211> LENGTH: 16
<212> TYPE: RNA
<213> ORGANISM: Homo sapiens

<400> SEQUENCE: 111
cuagaaaaac uggaga                                                    16

<210> SEQ ID NO 112
<211> LENGTH: 15
<212> TYPE: RNA
<213> ORGANISM: Mus musculus

<400> SEQUENCE: 112
cuagaaaacu ggaga                                                     15

<210> SEQ ID NO 113
<211> LENGTH: 15
<212> TYPE: RNA
<213> ORGANISM: Rattus norvegicus

<400> SEQUENCE: 113
cuagaaaacu ggaca                                                     15

<210> SEQ ID NO 114
<211> LENGTH: 15
<212> TYPE: RNA
<213> ORGANISM: Canis familiaris

<400> SEQUENCE: 114
cuagaaaacu ggaga                                                     15
```

```
<210> SEQ ID NO 115
<211> LENGTH: 24
<212> TYPE: RNA
<213> ORGANISM: Homo sapiens

<400> SEQUENCE: 115
guccaguuuu cccaggaauc ccuu                                          24

<210> SEQ ID NO 116
<211> LENGTH: 30
<212> TYPE: DNA
<213> ORGANISM: Gallus gallus

<400> SEQUENCE: 116
attatgtctt agcatctcat tttgtgaaaa                                    30
```

MICRO-RNAS THAT MODULATE SMOOTH MUSCLE PROLIFERATION AND DIFFERENTIATION AND USES THEREOF

CROSS-REFERENCE TO RELATED APPLICATIONS

This application claims the benefit of U.S. Provisional Application No. 61/030,467, filed Feb. 21, 2008, which is herein incorporated by reference in its entirety.

STATEMENT OF GOVERNMENT SUPPORT

This invention was made with grant support under grant no. HL53351-06 from the National Institutes of Health. The government has certain rights in the invention.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG 011 01US SeqList_ST25.txt, date recorded: Apr. 17, 2009, file size 18 kilobytes).

FIELD OF THE INVENTION

The present invention relates generally to the fields of developmental biology and molecular biology. More particularly, it concerns gene regulation and cellular physiology in smooth muscle cells, including those present in vascular tissue. Specifically, the invention relates to miRNAs that are involved in regulating smooth muscle cell differentiation and proliferation. Up-regulation of these miRNAs to treat or inhibit restenosis and neointima formation is disclosed.

BACKGROUND OF THE INVENTION

Cardiovascular disease remains by far the leading cause of death in Western nations and carries an unparalleled health and economic burden. Treatment by balloon angioplasty (percutaneous transluminal angioplasty, or PTA) has been shown to improve life expectancy. Although angioplasty is an alternative to bypass surgery for relieving stenosis of obstructive atherosclerotic blood vessels, the long-term success of the angioplasty is often compromised by the onset of restenosis and neointima formation. In the PTA procedure, an inflatable balloon disposed at the distal end of a catheter is positioned in the region of a stenosis. The balloon is inflated under fluid pressure to reconfigure the narrowed lumen thus permitting increased blood flow through the affected artery. It is not unusual that inflation-deflation cycles will be repeated, several times where the narrowing is severe. This mechanical violence to the arterial wall may produce the desired opening of the artery, but the procedure is followed by an estimated 25% to 50% incidence of restenosis, typically within 6 months to 2 years of the procedure at or near the injured site.

Serial intravascular ultrasound studies have shown that restenosis after stent deployment is due almost entirely to smooth muscle hyperplasia and matrix proliferation. In-stent neointima formation thus remains a major procedural limitation for stent use, limiting both utilization and long-term clinical benefits.

Vessel injury, such as endothelial denudation, injury to the vascular wall, and rupture of the vase vasorum, can result as an unwanted consequence to an angioplasty thereby making the treated site susceptible to restenosis. Upon injury, the ensuing deposition of platelets, in connection with the vessel's healing mechanism, signals smooth muscle cell proliferation within the arterial wall. The deposition of platelets may lead to acute thrombosis in some circumstances. More significantly, the proliferation of smooth muscle cells is a process which frequently continues unabated and has therefore been widely implicated as a prominent factor in the resulting restenosis. No pharmacologic or mechanical intervention has heretofore proven sufficiently effective in preventing restenosis following angioplasties. Therefore, novel therapies for preventing restenosis and enhancing the benefit of angioplasty are needed.

SUMMARY OF THE INVENTION

The present invention is based, in part, on the discovery that miR-143 and miR-145 are enriched in smooth muscle tissue, can regulate smooth muscle proliferation, and can reduce neointima formation after vessel injury. Accordingly, the present invention provides a method of inhibiting restenosis or neointima formation in a subject in need thereof. In one embodiment, the method comprises administering to the subject an agonist of miR-143 and/or miR-145. Agonists of miR-143 and/or miR-145 can be polynucleotides comprising a pri-miRNA, pre-miRNA, or mature miRNA sequence of miR-143 and/or miR-145. In some embodiments, the miR-143 and/or miR-145 agonist is expressed in vivo from an expression vector.

In another embodiment, the method of inhibiting restenosis or neointima formation in a subject in need thereof comprises administering to the subject an inhibitor of miR-486. MiR-486 downregulates PTEN, a negative regulator of cell proliferation, contributing to smooth muscle cell proliferation and neointima formation. A miR-486 inhibitor may be an antagomir, an antisense oligonucleotide, or an inhibitory RNA molecule. In another embodiment of the invention, the method comprises administering to the subject a miR-143/miR-145 agonist and a miR-486 inhibitor. In still another embodiment, the method further comprises administering to the subject a second agent that inhibits restenosis or neointima formation.

The present invention also includes a method of inhibiting smooth muscle cell proliferation. In one embodiment, the method comprises contacting a smooth muscle cell with an agonist of miR-143 and/or miR-145. In another embodiment, the method comprises contacting a smooth muscle cell with an inhibitor of miR-486.

The present invention also encompasses a pharmaceutical composition comprising an agonist of miR-143 and/or miR-145 and a pharmaceutically acceptable carrier. In another embodiment, the composition further comprises an inhibitor of miR-486. In another embodiment, the composition is formulated as a coating for a medical device, such as a catheter or a stent.

The present invention also provides a method of treating pathologic cardiac hypertrophy, heart failure, or myocardial infarction in a subject in need thereof comprising administering an agonist of miR-486 and/or miR-422a. Agonists of miR-486 and/or miR-422a include polynucleotides comprising a pri-miRNA, pre-miRNA, or mature miRNA sequence of miR-486 and/or miR-422a. In some embodiments, the miR-486 and/or miR-422a agonists are expressed from an expression vector.

In yet another embodiment, there is provided a transgenic, non-human mammal, the cells of which fail to express a functional miR-143, miR-145, miR-422a, and/or miR-486.

Another embodiment includes a transgenic, non-human mammal, the cells of which comprise a miR-143, miR-145, miR-422a, and/or miR-486 coding region under the control of a heterologous promoter active in the cells of the non-human mammal. The promoter may be a tissue specific promoter, such as a smooth muscle specific promoter, or a heart muscle specific promoter. Still another embodiment provides for a transgenic, non-human mammalian cell lacking one or both native alleles of miR-143, miR-145, miR-422a, and/or miR-486. The cell may lack both native miR-143, miR-145, miR-422a, or miR-486 alleles.

In another embodiment, there is provided a method for identifying a modulator of miR-143, miR-145, miR-422a, and/or miR-486 activity in vascular smooth muscle or cardiac muscle comprising (a) contacting a vascular smooth muscle cell or cardiomyocyte with a candidate compound; (b) assessing miR-143, miR-145, miR-422a, and/or miR-486 activity or expression; and (c) comparing the activity or expression in step (b) with the activity or expression in the absence of the candidate compound, wherein a difference between the measured activities or expression indicates that the candidate compound is a modulator of miR-143, miR-145, miR-422a, and/or miR-486. The cell may be contacted with the candidate compound in vitro or in vivo. The modulator of miR-143, miR-145, miR-422a, and/or miR-486 may be an agonist of miR-143, miR-145, miR-422a, and/or miR-486 or an inhibitor of miR-143, miR-145, miR-422a, and/or miR-486. In some embodiments, assessing miR-143, miR-145, miR-422a, and/or miR-486 activity or expression comprises assessing expression or activity of a gene regulated by miR-143, miR-145, miR-422a, and/or miR-486. Genes regulated by miR-143 and/or miR-145 include Slit-Robo GTPase activating proteins 1 and 2, Smad3, Sema3, Cited2, KLF5, or MRTFb. Genes regulated by miR-486 include PTEN and Foxo1a.

BRIEF DESCRIPTION OF THE DRAWINGS

The invention may be better understood by reference to one or more of these drawings in combination with the detailed description of specific embodiments presented herein.

FIG. 10. Identification of microRNAs enriched by myocardin or MRTFa. A. Cardiac myocytes were infected with adenovirus directing expression of βgal, MRTFa or myocardin. Enriched microRNAs were identified by microarray. B. MiR-486 was significantly enriched specifically upon overexpression of MRTFa, but not myocardin (myocd) as observed by Northern blot. C. MiR-486 is located in the final intron of the Ank1 gene, which contains an alternative promoter that directs muscle-specific expression. The stem loop structure (SEQ ID NO: 69) and mature microRNA (SEQ ID NO: 70)

Figure 1:
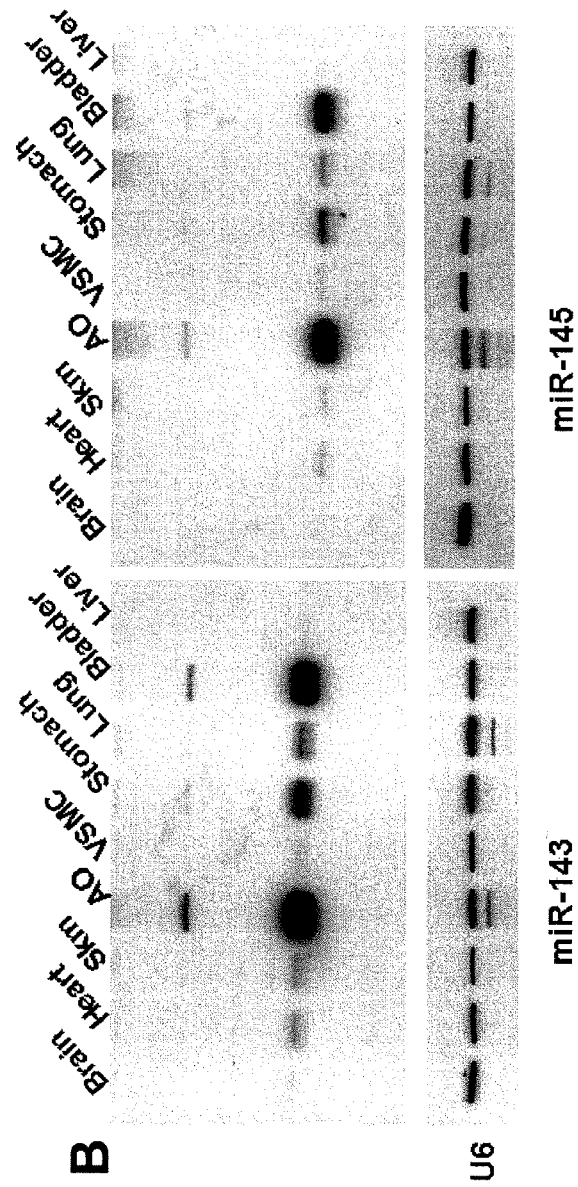
FIG. 1. A. MicroRNA microarray analysis identified microRNA genes enriched in smooth muscle (Aorta, Ao) as compared with skeletal muscle (Extensor Digitorum Longus, EDL) and heart muscle. MiR-145 and miR-143 are significantly enriched in smooth muscle. B. Northern blot of multiple adult mouse tissues showing tissue distribution of miR-143 (left panel) and miR-145 (right panel). Significant enrichment is observed in smooth muscle of the aorta (Ao), stomach, lung, and bladder. Skeletal muscle (Skm); Vascular Smooth Muscle Cells (VSMC).

sequence are shown. Real time PCR analysis of cardioymyocytes expressing MRTFa or GFP shows that miR-486 (D) and Ank1 (E) are rapidly induced by MRTFa.

FIG. 11. Expression of miR-486 A. Multiple tissue Northern blot depicting the expression of miR-486 in the adult mouse. Expression is enriched in cardiac, skeletal and smooth muscle derivatives. B. Expression of the miR-486 host gene, sAnk1, during embryogenesis. Wholemount in situ hybridization (ISH) of an E11.5 embryo depicting expression in the somites. Radioactive section ISH demonstrates sAnk1 expression in the somites at E10.5 and E12.5. Expression is observed in the developing skeletal muscle progenitors, tongue, diaphragm, and weakly in the atrium and liver. C. Expression of miR-486 host gene, Ank1, in the heart during embryonic stages as demonstrated by semi-quantitative RT-PCR. D. MiR-486 expression correlates with differentiation of the skeletal muscle cell line C2C12.

FIG. 12. Identification of miR-486/Ank1 regulatory sequences. A. MiR-486 and Ank1 expression are induced specifically by MRTFa in cardiomyocytes. Myocardin is insufficient to induce miR-486 or Ank1. B. Schematic depicting the predicted transcription factor binding sites in the regulatory region of the sAnk1 gene. C. Transgenic animals harboring the 1080 bpAnk1-hsp68lacZ reporter construct exhibit skeletal muscle specific βgal activity. Somite staining is observed at E9.5, and somite and developing skeletal muscle staining is observed at E11.5 and E13.5. D. COS cells were co-transfected with 50 ng, 100 ng and 200 ng of expression plasmids for MyoD, Nkx2-5, GATA-4, myocardin, or MRTFa and the luciferase reporter construct. The 1080 bp region upstream of the sAnk1 gene is activated by MyoD, Nkx2-5 and GATA-4 in COS cells, but not myocardin or MRTFa. E. 650 bp of sAnk1 intron 1 is specifically activated by MRTFa, but not myocardin or MRTFb in transiently transfected COS cells. F. Transfection of various luciferase reporters in cardiomyocytes transduced with 10 MOI of βgal, myocardin, MRTFa, or Nkx2-5 adenovirus. sAnk1 intron-luc (intron) is responsive to MRTFa in cardiomyocytes. The construct containing the promoter region of the sAnk1 (prom.) is not responsive to MRTFa in cardiomyocytes. G. Mutational analysis of sAnk1 intron-luciferase reporter in COS cells. 3' truncation (trunc) or mutation of the distal CArG2 (mutC2) result in loss of activity. 10QB, 25QB, and 50QB represent different concentrations of MRTFa.

FIG. 13. miR-486 targets PTEN and Foxo1a and regulates Akt signaling. A. Illustration of evolutionarily conserved predicted target 3'UTR sites for PTEN and Foxo1a, and the corresponding miR-486 seed sequence. B. Luciferase constructs linked to the 3'UTRs of the PTEN and Foxo1a genes and an artificial miR-486 binding site (sponge) are repressed by transfection of miR-486 in COS cells. C. Endogenous PTEN protein levels are reduced in cardiac myocytes upon MRTFa-induced miR-486 overexpression, which also display an increase in phosphorylated Akt. D. STARS and MRTFa co-expression result in a more robust repression of PTEN in cardiomyocytes than MRTFa alone. Downstream Akt signaling readouts, phospho-Akt and phospho-GSK3β, are synergistically induced upon co-expression of STARS and MRTFa. E. siRNA-mediated knockdown of miR-486 in cardiac myocytes completely abolishes the increase in miR-486 levels in response to MRTFa. F. siRNA to miR-486 abrogates the repression of PTEN and Foxo1a and the activation of Akt signaling in cardiomyocytes. G. Adenovirus-directed expression of miR-486 in cardiomyocytes results in reduction of PTEN protein levels.

FIG. 14. Modulation of miR-486 expression in cardiac stress response. A. MiR-486 expression is significantly reduced in the border zone 3 days post myocardial infarction (MI) while expression in remote tissue is unchanged. By 14 days post-MI, miR-486 levels are normal in the border zone and increased in remote tissues. B. Northern blot showing elevated expression of miR-486 in the heart of a MHCα-miR-486 transgenic mouse as compared to a non-transgenic littermate. C. MHCα-miR-486 transgenic animals exhibit an increase in phospho-Akt in the heart as compared to non-transgenic littermate.

DETAILED DESCRIPTION

MicroRNAs (miRNAs or miRs) have recently been implicated in a number of biological processes including regulation of developmental timing, apoptosis, fat metabolism, and hematopoietic cell differentiation among others. mRNAs are small, non-protein coding RNAs of about 18 to about 25 nucleotides in length that regulate gene expression in a sequence-specific manner. mRNAs act as repressors of target mRNAs by promoting their degradation, when their sequences are perfectly complementary, or by inhibiting translation, when their sequences contain mismatches.

mRNAs are transcribed by RNA polymerase II (pol II) or RNA polymerase III (pol III; see Qi et al. (2006) Cellular & Molecular Immunology Vol. 3:411-419) and arise from initial transcripts, termed primary miRNA transcripts (pri-miRNAs), that are generally several thousand bases long and are derived from individual miRNA genes, from introns of protein coding genes, or from poly-cistronic transcripts that often encode multiple, closely related miRNAs. See review of Carrington et al. (2003). Pri-miRNAs are processed in the nucleus by the RNase Drosha into about 70- to about 100-nucleotide hairpin-shaped precursors (pre-miRNAs). Following transport to the cytoplasm, the hairpin pre-miRNA is further processed by Dicer to produce a double-stranded miRNA (Lee et al., 1993). The mature miRNA strand is then incorporated into the RNA-induced silencing complex (RISC), where it associates with its target mRNAs by base-pair complementarity. In the relatively rare cases in which a miRNA base pairs perfectly with an mRNA target, it promotes mRNA degradation. More commonly, miRNAs form imperfect heteroduplexes with target mRNAs, affecting either mRNA stability or inhibiting mRNA translation.

Using an unbiased microarray approach, the inventors identified a cluster of two miRNAs that are enriched in smooth muscle cells of the aorta. Using multiple-tissue Northern blots, they validated the expression of the miR-143/miR-145 cluster in smooth muscle cell derivatives of the mouse. Both miR-143 and miR-145 are down-regulated after vessel injury and administration of miR-143 agonists reduced neointima formation induced by carotid artery ligation (see Example 3). Thus, the present invention is based, in part, on the discovery that miR-143 and miR-145 are enriched in smooth muscle tissue, can regulate smooth muscle proliferation, and can reduce neointima formation after vessel injury. Accordingly, the present invention provides a method of inhibiting smooth muscle cell proliferation. In one embodiment, the method comprises contacting a smooth muscle cell with an agonist of miR-143 or miR-145. In another embodiment, the smooth muscle cell is a human smooth muscle cell.

The inventors have also shown that overexpression of miR-486, a miRNA enriched in cardiac, skeletal, and smooth muscle, represses the translation of a PTEN 3'UTR-containing reporter in vitro (see Example 6). The PTEN gene, which is a negative regulator of pro-survival Akt signaling, has been an intriguing target of therapeutic investigation for arterial restenosis and myocardial infarction (Huang et al., 2004;

Mocanu and Yellon, 2007). Overexpression of PTEN in balloon injured carotid arteries in rats has resulted in a reduction of neointima formation (Huang et al., 2004). Thus, inhibition of miR-486 in smooth muscle tissue can lead to an increase in PTEN expression and subsequent reduction in neointima formation. Therefore, in another embodiment, the present invention provides a method of inhibiting smooth muscle cell proliferation comprising contacting a smooth muscle cell with an inhibitor of miR-486.

MiR-143 and miR-145 comprise a microRNA cluster in the intergenic region of human chromosome 5. Adjacent regulatory sequences contain conserved binding sites for the SRF protein, a previously described co-activator of myocardin and MRTF. The pre-miRNA sequences for miR-143 and miR-145 are processed into a mature sequence and a star sequence. The star sequence is processed from the other strand of the stem loop structure. The mature and star sequences for miR-143 and miR-145 are given below:

```
Human mature miR-143
UGAGAUGAAGCACUGUAGCUC        (SEQ ID NO: 38)

Human miR-143*
GGUGCAGUGCUGCAUCUCUGGU       (SEQ ID NO: 91)

Human mature miR-145
GUCCAGUUUUCCCAGGAAUCCCU      (SEQ ID NO: 51)

Human miR-145*
GGAUUCCUGGAAAUACUGUUCU       (SEQ ID NO: 92)
```

MiR-486 is located in the last intron, which is part of an alternative transcript expressed specifically in muscle cells, of the Ankl gene on human chromosome 8. Adjacent regulatory sequences contain conserved binding sites for the SRF protein. The human sequence for miR-486-5p is UCCUGUACUGAGCUGCCCCGAG (SEQ ID NO: 70). The human sequence for miR-486-3p is CGGGGCAGCUCAGUACAGGAU (SEQ ID NO: 93), which is processed from the other strand of the stem-loop structure.

MiR-422a is an intergenic microRNA located on chromosome 15. MiR-422a, like miR-486, was also found to be regulated by MRTFa. Adjacent regulatory sequences contain conserved binding sites for the SRF protein. The sequence for miR-422a is 5'-ACUGGACUUAGGGUCAGAAGGC-3' (SEQ ID NO: 94).

In one embodiment, the present invention provides a method for inhibiting smooth muscle cell proliferation by utilizing agonists of miR-143 and/or miR-145 or inhibitors of miR-486. In another embodiment, the present invention provides a method of inhibiting restenosis or neointima formation in a subject in need thereof. In one embodiment, the method comprises administering to the subject an inhibitor of miR-486. In another embodiment, the method comprises administering an agonist of miR-143 and/or miR-145. In another embodiment, the method comprises administering a miR-143/miR-145 agonist and a miR-486 inhibitor. In yet another embodiment, the subject is human. Restenosis literally means the reoccurrence of stenosis. Restenosis usually occurs in an artery, or other blood vessel, but possibly any hollow organ that has been "unblocked." This term is common in vascular surgery, cardiac surgery, interventional radiology, or interventional cardiology following angioplasty, all of which are branches of medicine that frequently treat stenotic lesions and neointima. Preferably, one or more symptoms of restenosis or neointima formation are reduced following administration of the miR-486 inhibitor and/or the miR-143/miR-145 agonist. Such symptoms include, but are not limited to, angina or myocardial infarction, and the need for additional angioplasty or stenting.

In one embodiment, an agonist of miR-143 and/or miR-145 can be a polynucleotide comprising a mature miR-143 and/or miR-145 sequence. In another embodiment, an agonist of miR-143 and/or miR-145 can be a polynucleotide comprising a star miR-143 and/or miR-145 sequence. In some embodiments, the polynucleotide comprises the sequence of SEQ ID NO: 38, SEQ ID NO: 51, SEQ ID NO: 91, or SEQ ID NO: 92. In another embodiment, the agonist of miR-143 and/or miR-145 can be a polynucleotide comprising the pri-miRNA or pre-miRNA sequence for miR-143 and/or miR-145. The polynucleotide comprising the mature miR-143/miR-145, pre-miR-143/pre-miR-145, or pri-miR-143/pri-miR-145 sequence can be single stranded or double stranded. The polynucleotides can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-143 and/or miR-145 sequence is conjugated to cholesterol. In another embodiment, the agonist of miR-143 and/or miR-145 can be an agent distinct from miR-143 or miR-145 that acts to increase, supplement, or replace the function of miR-143 and/or miR-145. For instance, serum response factor (SRF) or myocardin, both of which up-regulate expression of miR-143 and miR-145, can be agonists of miR-143 and/or miR-145.

In another embodiment, the agonist of miR-143 and/or miR-145 can be expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-143 and/or miR-145 comprises a promoter "operably linked" to a polynucleotide encoding miR-143 and/or miR-145. In another embodiment, the polynucleotide may encode the miR-143/miR-145 cluster. The phrase "operably linked" or "under transcriptional control" as used herein means that the promoter is in the correct location and orientation in relation to a polynucleotide to control the initiation of transcription by RNA polymerase and expression of the polynucleotide. The polynucleotide encoding miR-143 and/or miR-145 may encode the primary microRNA-miR-143 and/or miR-145 sequence (pri-miR-miR-143/pri-miR-145), the precursor-microRNA-miR-143 and/or miR-145 sequence (pre-miR-miR-143/pre-miR-145), the mature miR-143 and/or miR-145 sequence, or the star miR-143 and/or miR-145 sequence. In another embodiment, the expression vector comprises a polynucleotide operably linked to a promoter, wherein said polynucleotide comprises the sequence of SEQ ID NO: 38. In another embodiment, the expression vector comprises a polynucleotide operably linked to a promoter, wherein said polynucleotide comprises the sequence of SEQ ID NO: 51. In still another embodiment, the expression vector comprises a polynucleotide operably linked to a promoter, wherein said polynucleotide comprises the sequence of SEQ ID NO: 91 or SEQ ID NO: 92. The polynucleotide comprising the sequence of SEQ ID NO: 38, SEQ ID NO: 51, SEQ ID NO: 91 or SEQ ID NO: 92 may be about 18 to about 2000 nucleotides in length, about 70 to about 200 nucleotides in length, about 20 to about 50 nucleotides in length, or about 18 to about 25 nucleotides in length.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III.

In some embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the polynucleotide sequence of interest. The use of other viral or mammalian cellular or bacterial phage promoters which are well-known in the art to achieve expression of a polynucleotide sequence of interest is contemplated as well, provided that the levels of expression are sufficient for a given purpose.

By employing a promoter with well-known properties, the level and pattern of expression of the polynucleotide of interest following transfection or transformation can be optimized. Further, selection of a promoter that is regulated in response to specific physiologic signals can permit inducible expression of the polynucleotide. Tables 1 and 2 list several regulatory elements that may be employed, in the context of the present invention, to regulate the expression of the polynucleotide of interest (e.g. agonists or inhibitors of miR-143, miR-145, miR-486, and/or miR-422a). This list is not intended to be exhaustive of all the possible elements involved in the promotion of gene expression but, merely, to be exemplary thereof.

Below is a list of viral promoters, cellular promoters/enhancers and inducible promoters/enhancers that could be used in combination with the polynucleotide of interest in an expression construct (Table 1 and Table 2). Additionally, any promoter/enhancer combination (as per the Eukaryotic Promoter Data Base EPDB) could also be used to drive expression of the polynucleotide. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $α_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; |

TABLE 1-continued

Promoter and/or Enhancer

| Promoter/Enhancer | References |
|---|---|
| | Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI) x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober and Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

A polyadenylation signal may be included to effect proper polyadenylation of the gene transcript where desired. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express a polynucleotide that has been cloned therein. The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

The typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

Retroviral vectors are also suitable for expressing agonists of miR-143, miR-145, miR-422a, and/or miR-486 in cells. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Porter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ohosh and Bachhawat, 1991). Also contemplated are lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-I) (Kato et al., 1991). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In a particular example, the oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877, 302, 6,008,336, 6,077,835, 5,972,901, 6,200,801, and 5,972, 900, which are incorporated by reference for those aspects.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

In another embodiment of the invention, the method for inhibiting smooth muscle cell proliferation comprises contacting a smooth muscle cell with an inhibitor of miR-486. In yet another embodiment of the invention, the method of inhibiting restenosis or neointima formation in a subject in need thereof comprises administering to the subject an inhibitor of miR-486. Inhibitors of miR-486 can include antagomirs, antisense oligonucleotides, and inhibitory RNA molecules.

Inhibition of microRNA function may be achieved by administering antisense oligonucleotides targeting a mature sequence of miR-486. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Preferable antisense oligonucleotides useful for inhibiting the activity of microRNAs are about 19 to about 25 nucleotides in length. Antisense oligonucleotides may comprise a sequence that is at least partially complementary to a mature miRNA sequence, e.g. at least about 75%, 80%, 85%, 90%, 95%, 96%, 97%, 98%, or 99% complementary to a mature miRNA sequence. In some embodiments, the antisense oligonucleotide may be substantially complementary to a mature miRNA sequence, that is at least about 95%, 96%, 97%, 98%, or 99% complementary to a target polynucleotide sequence. In one embodiment, the antisense oligonucleotide comprises a sequence that is 100% complementary to a mature miRNA sequence.

In some embodiments, the antisense oligonucleotides are antagomirs. "Antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol or other moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomir may be substantially complementary to a mature miRNA sequence, that is at least about 95%, 96%, 97%, 98%, or 99% complementary to a target polynucleotide sequence. In other embodiments, the antagomirs are 100% complementary to the mature miRNA sequence.

Another approach for inhibiting the function of miR-486 is administering an inhibitory RNA molecule having a double stranded region that is at least partially identical and partially complementary to a mature sequence of miR-486. The inhibitory RNA molecule may be a double-stranded, small interfering RNA (siRNA) or a short hairpin RNA molecule (shRNA) comprising a stem-loop structure. The double-stranded regions of the inhibitory RNA molecule may comprise a sequence that is at least partially identical and partially complementary, e.g. about 75%, 80%, 85%, 90%, 95%, 96%, 97%, 98%, or 99% identical and complementary, to the mature miRNA sequence. In some embodiments, the double-stranded regions of the inhibitory RNA comprise a sequence that is at least substantially identical and substantially complementary to the mature miRNA sequence. "Substantially identical and substantially complementary" refers to a sequence that is at least about 95%, 96%, 97%, 98%, or 99% identical and complementary to a target polynucleotide sequence. In other embodiments, the double-stranded regions of the inhibitory RNA molecule may contain 100% identity and complementarity to the target miRNA sequence.

The inhibitory nucleotide molecules described herein preferably target a mature sequence of miR-486 (e.g. SEQ ID NO: 70 or SEQ ID NO: 93). In some embodiments, inhibitors of miR-486 are antagomirs comprising a sequence that is perfectly complementary to a mature sequence of miR-486. In one embodiment, an inhibitor of miR-486 is an antagomir having a sequence that is partially or perfectly complementary to SEQ ID NO: 70 or SEQ ID NO: 93.

In some embodiments, inhibitors of miR-486 are chemically-modified antisense oligonucleotides. In one embodiment, an inhibitor of miR-486 is a chemically-modified antisense oligonucleotide comprising a sequence substantially complementary to SEQ ID NO: 70 or SEQ ID NO: 93. As used herein "substantially complementary" refers to a sequence that is at least about 95%, 96%, 97%, 98%, 99%, or 100% complementary to a target polynucleotide sequence (e.g. mature or precursor miRNA sequence).

Antisense oligonucleotides may comprise a sequence that is substantially complementary to a precursor miRNA sequence (pre-miRNA) for miR-486 (e.g. pre-miR-486). In some embodiments, the antisense oligonucleotide comprises a sequence that is substantially complementary to a sequence located outside the stem-loop region of the pre-miRNA sequence.

In other embodiments of the invention, inhibitors of miR-486 may be inhibitory RNA molecules, such as ribozymes, siRNAs, or shRNAs. In one embodiment, an inhibitor of miR-486 is an inhibitory RNA molecule comprising a double-stranded region, wherein the double-stranded region comprises a sequence having 100% identity and complementarity to a mature sequence of miR-486 (e.g. SEQ ID NO: 70 or SEQ ID NO: 93). In some embodiments, inhibitors of miR-486 are inhibitory RNA molecules which comprise a double-stranded region, wherein said double-stranded region comprises a sequence of at least about 75%, 80%, 85%, 90%, 95%, 96%, 97%, 98%, or 99% identity and complementarity to a mature sequence of miR-486.

In another embodiment of the invention, an agonist of miR-143 and/or miR-145 or an inhibitor of miR-486 can be used in combination with other therapeutic modalities, for instance, other agents that inhibit restenosis or neointima formation. Cardiologists have tried a number of approaches to decrease the risk of restenosis. Stenting is becoming more commonplace, replacing balloon angioplasty. During the stenting procedure, a metal mesh (stent) is deployed against the wall of the artery revascularizing the artery. Other approaches include local radiotherapy and the use of immunosuppressive drugs, coated onto the stenting mesh. Thus, examples of combination therapies include any of the foregoing.

Combinations may be achieved by contacting vascular smooth muscle cells with a single composition or pharmacological formulation that includes both agents, or by contacting the cell with two distinct compositions or formulations, at the same time, wherein one composition includes the miR-143/miR-145 agonist and/or the miR-486 inhibitor and the other includes the second agent. Alternatively, the therapy using a miR-143/miR-145 agonist and/or a miR-486 inhibitor may precede or follow administration of the other agent(s) by intervals ranging from minutes to weeks. In embodiments where the other agent and miR-143/miR-145 agonist or miR-486 inhibitor are applied separately to the cell, one would generally ensure that a significant period of time did not expire between the time of each delivery, such that the agent and the miR-143/miR-145 agonist or miR-486 inhibitor would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of the miR-143/miR-145 agonist or miR-486 inhibitor, or the other agent will be desired. In this regard, various combinations may be employed. By way of illustration, where the miR-143/miR-145 agonist or miR-486 inhibitor is "A" and the other agent is "B," the following permutations based on 3 and 4 total administrations are exemplary:

A/B/A B/A/B B/B/A A/A/B B/A/A A/B/B B/B/B/A

B/B/A/B A/A/B/B A/B/A/B A/B/B/A B/B/A/A B/A/B/A

B/A/A/B B/B/B/A A/A/A/B B/A/A/A A/B/A/A A/A/B/A

A/B/B/B B/A/B/B B/B/A/B

Other combinations are likewise contemplated. Specific examples of the "other" therapy are provided below.

In another embodiment of the invention, the method of inhibiting restenosis or neointima formation in a subject in need thereof further comprises administering to the subject a second agent that inhibits restenosis or neointima formation. Specific agents shown herein to be anti-restenotic agents include angiotensin converting enzyme inhibitors; nicotine receptor agonists, agents that increase concentrations of nitric oxide, anti-angiogenic agents, agonists of the TGF-β receptor; death domain receptor ligands; and thrombin inhibitors. The agents may be delivered in the form of polypeptides, peptides, small organic molecules, nucleic acids encoding a polypeptide of interest, and the like. A polypeptide may be any translation product of a nucleic acid regardless of size and glycosylation. Agents may also be in the form of simple drugs, peptides, peptide fragments, DNA, RNA, ribozymes or engineered hybrids of nucleic acids and peptides or peptide fragments, or derivatives of each. Analogues of rapamycin, such as tacrolimus (FK-506), sirolimus and everolimus, normally used as immunosuppressants but recently discovered to also inhibit the proliferation of vascular smooth muscle cells, have appeared to be quite effective in preventing restenosis in clinical trials. Antisense knockdown of c-myc, a protein critical for progression of cell replication, is another approach to inhibit cell proliferation in the artery wall and has been through preliminary clinical trials using m oligos.

Angiotensin converting enzyme inhibitors (ACE-I) are used for antihypertensive and renoprotective actions. ACE inhibitor include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include losartan, irbesartan, candesartan, cilexetil, and valsartan. Nicotine receptor agonist, e.g., nicotine (S-3-(1-methyl-2-pyrrolidinyl)pyridine) and other compounds that substantially specifically bind a nicotine receptor and provide a pharmacological effect. "Nicotine receptor agonists" encompass naturally-occurring compounds (including, but not-limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., smallmolecules, peptides, etc.) The term "nicotine" further includes any pharmacologically acceptable derivative or metabolite of nicotine which: exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

Agents that increase nitric oxide are of interest as anti-restenotic agents, e.g., S-nitrosopenicillamine, sodium nitroprusside, N-ethyl-2-(1-ethyl-2-hydroxy-2nitrosohydrazino) ethanamine (NOC 12), etc. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al. Any of the forms of nitric oxide synthase can be utilized, as the protein or an active fragment derived therefrom, or as a DNA construct for expression.

Also of interest for the inhibition of restenosis are compounds with an anti-angiogenic effect. These include the anti-angiogenic polypeptides: angiostatin (O'Reilly et al., 1994); endostatin (O'Reilly et al., 1997); and anti-angiogenic anti-thrombin III (Bock et al., 1982); and the like, and further include functionally active variants and derivatives thereof. Other anti-angiogenic agents include inhibitors of matrix metalloproteases, e.g., amifostine, WR-1065; marimastat, primomastat, α-1 antitrypsin; sphingosine and the like.

Alternatively, compounds that block thrombin, and other anti-coagulants, may be used to inhibit restenosis, such compounds based on the tripeptide motif D-Phe-Pro-Arg; e.g., LY287045, etc. Many compounds, such as inogatran and melagatran, are known in the art. For non-limiting examples, see U.S. Pat. Nos. 6,326,386; 6,232,315; 6,201,006; 6,174,855; 6,060,451; and 5,985,833; among others.

Agonists of the TGF-β receptor are also of interest. TGF-β receptor Type I and type II mediate most activities of TGF-β (Ebner et al., 1993; and Franzen et al., 1993). Ligands include TGF-β, and mimetics and biologically active derivatives thereof. Non-covalent attachment of rapamycin to a stent-based delivery system is also of interest. Non-covalent attachment can consist of hydrogen bonding, van der waals forces, or simply passive entanglement in a highly viscous surface, or some combination thereof. Carriers specific to angiostatin can be applied for tight regulated binding, and cleavable linkers sensitive to moisture (time dependant in vivo), pH, osmolality, or a particular antigen among others are included, as are future linkers and related linkers well known to those skilled in the art.

Covalent or non-covalent attachment of antiplatelet agents are also of interest, including GPIIb/IIIa inhibitors, e.g., RheoPro.

For the induction of apoptosis, agents of interest include death domain receptor ligands, which are compounds, usually polypeptide compounds, that bind to mammalian cell surface receptors comprising a death domain, or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity (Huang et al., 1996). The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). Death domain ligands include proteins that regulate cellular proliferation and differentiation by binding to specific death domain receptors. These ligands include the TNF family, e.g., TNF, lymphotoxin, CD30 ligand, 4-1 BB ligand, CD40 ligand, CD27 ligand, and TRAIL (TNF-related apoptosis-inducing ligand), and homologs and analogs thereof. The functional, soluble forms of TNF as well as human FasL exists as trimers. Lymphotoxin β, a member of the TNF family, consists of a heterotrimer of one (lymphotoxin-α, or TNF-β) and two β chains (lymphotoxin-β) on the membrane.

Anti-restenotic polypeptides and peptides can be administered in their native form, or through the administration of expression vectors encoding the molecule of interest as described herein.

Complex systems of drugs may be carried by a stent. An anticoagulant or antiplatelet may be included in the outermost surface of the device in order to elute off very quickly for the first several days. Anti-inflammatories and anti-replicates can be formulated into the device to continue to elute later, when in contact with non-blood cells after neointima overgrowth has surrounded the device. The drug elution rate does not need to be uniform, and may be tailored to fit the need of the patient.

In still another embodiment of the invention, a miR-143/miR-145 agonist or miR-486 inhibitor as described herein may be formulated as a coating for a medical device, such as a stent, balloon, or catheter. Particularly useful in methods of treating restenosis in a subject, the miR-143/miR-145 agonist or miR-486 inhibitor can be used to coat a metal stent to produce a drug-eluting stent. A drug-eluting stent is a scaffold that holds open narrowed or diseased arteries and releases a compound to prevent cellular proliferation and/or inflammation. MiR-143/miR-145 agonists or miR-486 inhibitors may be applied to a metal stent imbedded in a thin polymer for release of the agonists or inhibitors over time. Methods for device-based delivery and methods of coating devices are well know in the art, as are drug-eluting stents and other implantable devices. See, e.g., U.S. Pat. Nos. 7,294,329, 7,273,493, 7,247,313, 7,236,821, 7,232,573, 7,156,869, 7,144,422, 7,105,018, 7,087,263, 7,083,642, 7,055,237, 7,041,127, 6,716,242, and 6,589,286, and WO 2004/004602, which are herein incorporated by reference in their entireties. Thus, the present invention includes a medical device, such as a balloon, catheter, or stent, coated with a miR-143 agonist, miR-145 agonist, and/or miR-486 inhibitor. In some embodiments, the miR-143/miR-145 agonist or miR-486 inhibitor can be used in combination with other anti-restenosis compounds as described herein to produce a formulation for incorporation into drug-eluting stents. Additional suitable compounds for use in combination with the miR-143/miR-145 agonist or miR-486 inhibitor include, but are not limited to, paclitaxel, rapamycin (sirolimus), tacrolimus, zotarolimus, everolimus, docetaxel, pimecrolimus, and derivatives thereof.

The present invention also includes a method of treating pathologic cardiac hypertrophy, heart failure, or myocardial infarction in a subject in need thereof. In one embodiment, the method comprises administering an agonist of miR-486 and/or miR-422a to the subject. Preferably, administration of the agonist of miR-486 and/or miR-422a results in the improvement of one or more symptoms of cardiac hypertrophy, heart failure, or myocardial infarction in the subject, or in the delay in the transition from cardiac hypertrophy to heart failure. The one or more improved symptoms may be, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, decreased wall tension, increased quality of life, and decreased disease related morbidity or mortality. In addition, use of miR-486/miR-422a agonists may prevent cardiac hypertrophy and its associated symptoms from arising. In one embodiment, administration of an agonist of miR-486 and/or miR-422a to a subject suffering from myocardial infarction may reduce infarct size by decreasing the loss of heart cells. In another embodiment, cardiac function is stabilized in a subject suffering from myocardial infarction following administration of an agonist of miR-486 and/or miR-422a.

In one embodiment, an agonist of miR-486 and/or miR-422a can be a polynucleotide comprising a mature miR-486 and/or miR-422a sequence. In some embodiments, the polynucleotide comprises the sequence of SEQ ID NO: 70, SEQ ID NO: 93, or SEQ ID NO: 94. In another embodiment, the agonist of miR-486 and/or miR-422a can be a polynucleotide comprising the pri-miRNA or pre-miRNA sequence for miR-486 and/or miR-422a. The polynucleotide comprising the mature miR-486 and/or miR-422a, pre-miR-486/pre-miR-422a, or pri-miR-486/pri-miR-422a sequence can be single stranded or double stranded. The polynucleotides can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-486 and/or miR-422a sequence is conjugated to cholesterol. In another embodiment, the agonist of miR-486 and/or miR-422a can be an agent distinct from miR-486 or miR-422a that acts to increase, supplement, or replace the function of miR-486 and/or miR-422a. For instance, SRF or MRTFa, both of which up-regulate expression of miR-486, can be agonists of miR-486.

In some embodiments, the agonist of miR-486 and/or miR-422a can be expressed in vivo from a vector as described herein. In one embodiment, an expression vector for expressing miR-486 and/or miR-422a comprises a promoter operably linked to a polynucleotide encoding miR-486 and/or miR-422a. The polynucleotide encoding miR-486 and/or miR-422a can encode the primary microRNA-miR-486 and/or miR-422a sequence (pri-miR-miR-486/pri-miR-422a), the precursor-microRNA-miR-486 and/or miR-422a sequence (pre-miR-miR-486/pre-miR-422a), or the mature miR-486 and/or miR-422a sequence. In another embodiment, the expression vector comprises a polynucleotide operably linked to a promoter, wherein said polynucleotide comprises the sequence of SEQ ID NO: 70. In another embodiment, the expression vector comprises a polynucleotide operably linked to a promoter, wherein said polynucleotide comprises the sequence of SEQ ID NO: 93. In still another embodiment, the expression vector comprises a polynucleotide operably linked to a promoter, wherein said polynucleotide comprises the sequence of SEQ ID NO: 94.

The present invention also contemplates methods for scavenging or clearing miR-143, miR-145, miR-486 and/or miR-422a agonists following treatment. In one embodiment, the method comprises overexpression of binding site regions for miR-143 and/or miR-145 in smooth muscle cells using a smooth muscle specific promoter. In another embodiment, the method comprises overexpression of binding site regions for miR-486 and/or miR-422a in cardiomyocytes using a cardiac specific promoter. The binding site regions preferably contain a sequence of the seed region, the 5' portion of a miRNA spanning bases 2-8, for miR-143, miR-145, miR-486 and/or miR-422a. In some embodiments, the binding site may contain a sequence from the 3' UTR of one or more targets of miR-143 and/or miR-145, such as Srgap1, Srgap2, Smad3, Sema3, Cited2, KLF5, and MRTFb. In other embodiments, the binding site may contain a sequence from the 3' UTR of one or more targets of miR-486, such as PTEN and Foxo1a. In another embodiment, a miR-143, miR-145, miR-486 and/or miR-422a inhibitor may be administered after a miR-143, miR-145, miR-486 and/or miR-422a agonist to attenuate or stop the function of the microRNA. In another embodiment, the present invention provides a method for scavenging or clearing miR-486 inhibitors following treatment. The method may comprise overexpressing binding sites for the miR-486 inhibitors in smooth muscle cells or other tissue in which a miR-486 inhibitor was administered.

The present invention also encompasses pharmaceutical compositions comprising miR-143, miR-145, miR-486 and/or miR-422a agonists and a pharmaceutically acceptable carrier. In another embodiment, the pharmaceutical composition comprises a miR-486 inhibitor as described herein and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Colloidal dispersion systems, such as macromolecule complexes, nanocapsules, microspheres, beads, and lipid-based systems including oil-in-water emulsions, micelles, mixed micelles, and liposomes, may be used as delivery vehicles for the agonists or inhibitors of microRNA function described herein. Commercially available fat emulsions that are suitable for delivering the nucleic acids of the invention to tissues, such as cardiac muscle tissue and smooth muscle tissue, include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO 03/093449, which are herein incorporated by reference in their entireties.

One will generally desire to employ appropriate salts and buffers to render delivery vehicles stable and allow for uptake by target cells. Buffers also will be employed when recombinant cells are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the nucleic acids of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal, intraarterial or intravenous injection, or by direct injection into cardiac tissue. Pharmaceutical compositions comprising miRNA inhibitors or agonists can also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions, as described supra. In one embodiment, the pharmaceutical compositions of the invention can be administered by a stent coated with the pharmaceutical composition. This embodiment is particularly useful for treating or inhibiting restenosis and neointima formation.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Any of the compositions described herein may be comprised in a kit. In a non-limiting example, a miR-143, miR-145, miR-486 and/or miR-422a agonist is included in a kit. The kit may further include water and hybridization buffer to facilitate hybridization of the two strands of the miRNAs. The kit may also include one or more transfection reagent(s) to facilitate delivery of the polynucleotide agonists to cells.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

Such kits may also include components that preserve or maintain the miRNAs/polynucleotides or that protect against their degradation. Such components may be RNAse-free or protect against RNAses. Such kits generally will comprise, in suitable means, distinct containers for each individual reagent or solution.

A kit will also include instructions for employing the kit components as well the use of any other reagent not included in the kit. Instructions may include variations that can be implemented. A kit may also include utensils or devices for administering the miRNA agonist or inhibitor by various administration routes, such as parenteral or catheter administration or coated stent.

The present invention further comprises methods for identifying modulators of miR-143, miR-145, miR-422a, and/or miR-486. Identified agonists of the function of miR-143 and/or miR-145 are useful in the prevention or treatment of restenosis or neointima formation or inhibition of smooth muscle cell proliferation. Identified agonists of the function of miR-486 and/or miR-422a are useful in the prevention or treatment or reversal of cardiac hypertrophy, heart failure or myocardial infarction. Modulators (e.g. agonists) of miR-143, miR-145, miR-422a, and/or miR-486 can be included in pharmaceutical compositions for the treatment of restenosis or cardiac disorders according to the methods of the present invention.

These assays may comprise random screening of large libraries of candidate substances; alternatively, the assays may be used to focus on particular classes of compounds selected with an eye towards structural attributes that are believed to make them more likely to promote the expression and/or function of miR-143, miR-145, miR-422a, and/or miR-486.

To identify a modulator of miR-143, miR-145, miR-422a, and/or miR-486, one generally will determine the expression or activity of miR-143, miR-145, miR-422a, and/or miR-486 in the presence and absence of the candidate compound. For example, a method generally comprises:
  (a) providing a candidate compound;
  (b) admixing the candidate compound with a cell expressing miR-143, miR-145, miR-422a, and/or miR-486;
  (c) measuring miR-143, miR-145, miR-422a, and/or miR-486 expression or activity; and
  (d) comparing the expression or activity in step (c) with the activity in the absence of the candidate compound,
  wherein a difference between the measured expression or activity indicates that the candidate compound is, indeed, a modulator of miR-143, miR-145, miR-422a, and/or miR-486.
Assays also may be conducted in isolated tissues, organs, or in living organisms.

Assessing the activity or expression of miR-143, miR-145, miR-422a, and/or miR-486 may comprise assessing the expression level of miR-143, miR-145, miR-422a, and/or miR-486. Those in the art will be familiar with a variety of methods for assessing RNA expression levels including, for example, northern blotting or RT-PCR. Assessing the activity or expression of miR-143, miR-145, miR-422a, and/or miR-486 may comprise assessing the activity of miR-143, miR-145, miR-422a, and/or miR-486. In some embodiments, assessing the activity of miR-143, miR-145, miR-422a, and/or miR-486 comprises assessing expression or activity of a gene regulated by miR-143, miR-145, miR-422a, and/or miR-486. Genes regulated by miR-143 and/or miR-145 include, for example, Slit-Robo GTPase activating protein 1, Slit-Robo GTPase activating protein 2, Smad3, Sema3, Cited2, KLF5, or MRTFb. Genes regulated by miR-486 include, for example, PTEN and Foxo1a. Those in the art will be familiar with a variety of methods for assessing the activity or expression of genes regulated by miR-143, miR-145, miR-422a, and/or miR-486. Such methods include, for example, northern blotting, RT-PCR, ELISA, or western blotting.

It will, of course, be understood that all the screening methods of the present invention are useful in themselves notwithstanding the fact that effective candidates may not be found. The invention provides methods for screening for such candidates, not solely methods of finding them.

As used herein the term "candidate compound" refers to any molecule that may potentially modulate expression or proliferation-regulating aspects of miR-143, miR-145, miR-422a, and/or miR-486. One will typically acquire, from various commercial sources, molecular libraries that are believed to meet the basic criteria for useful drugs in an effort to "brute force" the identification of useful compounds. Screening of such libraries, including combinatorially-generated libraries, is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds. Non-limiting examples of candidate compounds that may be screened according to the methods of the present invention are proteins, peptides, polypeptides, polynucleotides, oligonucleotides or small molecules. Modulators of miR-143, miR-145, miR-422a, and/or miR-486 may also be agonists or inhibitors of upstream regulators of any one of miR-143, miR-145, miR-422a, and/or miR-486.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

A technique for high throughput screening of compounds is described in WO 84/03564. Large numbers of small compounds may be synthesized on a solid substrate, such as plastic pins or some other surface. Such molecules can be rapidly screened for their ability to induce miR-143, miR-145, miR-422a, and/or miR-486.

The present invention also contemplates the screening of compounds for their ability to modulate miR-143, miR-145, miR-422a, and/or miR-486 activity and expression in cells. Various cell lines, including those derived from vascular smooth muscle cells, can be utilized for such screening assays, including cells specifically engineered for this purpose.

In vivo assays involve the use of various animal models of restenosis, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria, including but not limited to alteration of proliferation of vascular smooth muscle cells.

The present invention includes a method of regulating expression of Slit-Robo GTPase activating protein 1, Slit-Robo GTPase activating protein 2, Smad3, Sema3, Cited2, KLF5, or MRTFb in a cell comprising contacting the cell with a modulator of a miR-143 and/or miR-145. In one embodiment, the expression of Slit-Robo GTPase activating protein 1, Slit-Robo GTPase activating protein 2, Smad3, Sema3, Cited2, KLF5, or MRTFb is decreased in the cell following administration of a miR-143 and/or miR-145 agonist. In another embodiment, the expression of Slit-Robo GTPase activating protein 2, Smad3, Sema3, Cited2, KLF5, or MRTFb is increased in the cell following administration of a miR-143 and/or miR-145 inhibitor.

The present invention includes a method of modulating the expression or activity of Slit-Robo GTPase activating protein 1, Slit-Robo GTPase activating protein 2, Smad3, Sema3, Cited2, KLF5, or MRTFb in a subject for treating or preventing restenosis. Suitable modulators include the miR agonists described herein, as well as small molecules, peptides, proteins, and inhibitory nucleic acids (e.g. ribozymes, siRNAs, antisense oligonucleotides).

In another embodiment, the present invention provides a method for regulating expression of PTEN or Foxo1a in a cell comprising contacting the cell with a modulator of a miR-486. In one embodiment, the expression of PTEN or Foxo1a is decreased in the cell following administration of a miR-486 agonist. In another embodiment, the expression of PTEN or Foxo1a is increased in the cell following administration of a miR-486 inhibitor. The present invention also encompasses a method of modulating the expression or activity of PTEN or Foxo1a in a subject for treating or preventing cardiac hypertrophy, heart failure, or myocardial infarction.

In still another embodiment, the present invention provides a method for regulating Akt signaling in a cell comprising contacting the cell with a modulator of miR-486. In one embodiment, Akt signaling in the cell is enhanced following administration of a miR-486 agonist. In another embodiment, Akt signaling in the cell is suppressed following administration of a miR-486 inhibitor.

A particular embodiment of the present invention provides transgenic animals that lack one or both functional miR-143, miR-145, miR-422a, and/or miR-486 alleles. Also, transgenic animals that express miR-143, miR-145, miR-422a, and/or miR-486 under the control of an inducible, tissue selective or a constitutive promoter, recombinant cell lines derived from such animals, and transgenic embryos may be useful in determining the exact role that these miRs play in the control of smooth muscle cell differentiation and proliferation, and thus in restenosis and neointima formation. The use of an inducible or repressable miR-143, miR-145, miR-422a, and/or miR-486 encoding nucleic acid provides a model for over- or unregulated expression. Also, transgenic animals that are "knocked out" for miR-143, miR-145, miR-422a, and/or miR-486, in one or both alleles, are contemplated. Also, transgenic animals that are "knocked out" for miR-143, miR-145, miR-422a, and/or miR-486, in one or both alleles for one or both clusters, are contemplated.

In a general aspect, a transgenic animal is produced by the integration of a given transgene into the genome in a manner that permits the expression of the transgene. Methods for producing transgenic animals are generally described by Wagner and Hoppe (U.S. Pat. No. 4,873,191; incorporated herein by reference), and Brinster et al. (1985; incorporated herein by reference).

Typically, a gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish.

DNA clones for microinjection can be prepared by any means known in the art. For example, DNA clones for microinjection can be cleaved with enzymes appropriate for removing the bacterial plasmid sequences, and the DNA fragments electrophoresed on 1% agarose gels in TBE buffer, using standard techniques. The DNA bands are visualized by staining with ethidium bromide, and the band containing the expression sequences is excised. The excised band is then placed in dialysis bags containing 0.3 M sodium acetate, pH 7.0. DNA is electroeluted into the dialysis bags, extracted with a 1:1 phenol:chloroform solution and precipitated by two volumes of ethanol. The DNA is redissolved in 1 ml of low salt buffer (0.2 M NaCl, 20 mM Tris, pH 7.4, and 1 mM EDTA) and purified on an Elutip-D™ column. The column is first primed with 3 ml of high salt buffer (1 M NaCl, 20 mM Tris, pH 7.4, and 1 mM EDTA) followed by washing with 5 ml of low salt buffer. The DNA solutions are passed through the column three times to bind DNA to the column matrix. After one wash with 3 ml of low salt buffer, the DNA is eluted with 0.4 ml high salt buffer and precipitated by two volumes of ethanol. DNA concentrations are measured by absorption at 260 nm in a UV spectrophotometer. For microinjection, DNA concentrations are adjusted to 3 µg/ml in 5 mM Tris, pH 7.4 and 0.1 mM EDTA. Other methods for purification of DNA for microinjection are described in Palmiter et al. (1982); and in Sambrook et al. (2001).

In an exemplary microinjection procedure, female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG injection, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection. Embryos can be implanted at the two-cell stage.

Randomly cycling adult female mice are paired with vasectomized males. C57BL/6 or Swiss mice or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS (Dulbecco's phosphate buffered saline) and in the tip of a transfer pipet (about 10 to 12 embryos). The pipet tip is inserted into the infundibulum and the embryos transferred. After the transfer, the incision is closed by two sutures.

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

MiR-143 and miR-145 are Enriched in Smooth Muscle Cells

Figure 2:
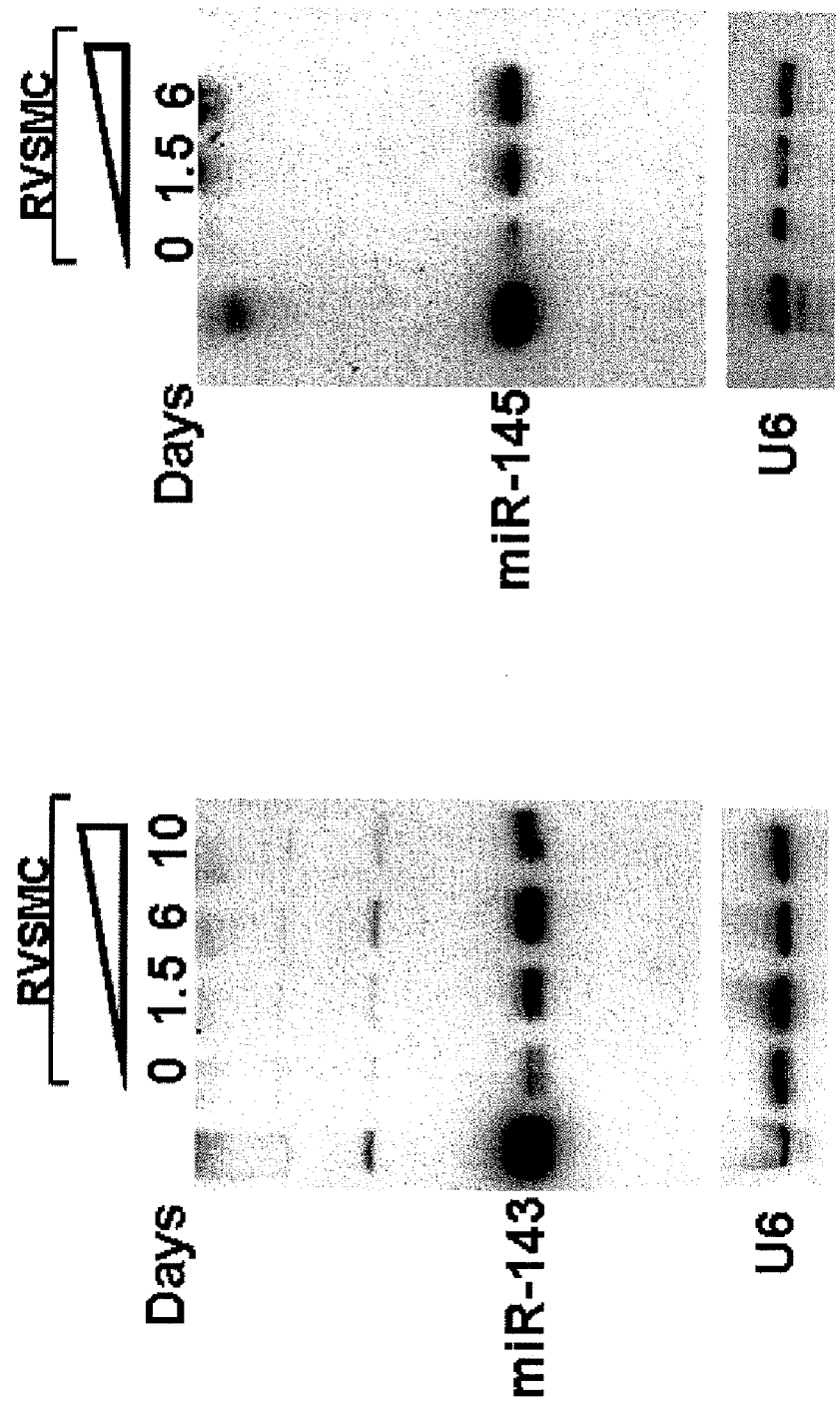
FIG. 2. Analysis of miR-143 and miR-145 expression during differentiation of rat aorta vascular smooth muscle cells (RVSMC) for 10 days. Expression of both miR-143 and miR-145 are increased during RVSMC differentiation, as assessed by Northern blot.

To identify smooth muscle enriched microRNAs, a micro array analysis was performed to compare microRNAs from the smooth muscle-enriched tissue of the aorta with those of the heart and skeletal muscle. The miR-143/145 microRNA cluster was identified as highly expressed in the aorta compared with that in the heart and skeletal muscle (FIG. 1A). The expression of miR-143/145 in smooth muscle-enriched tissues was further confirmed by Northern blot. MiR-143/145 were highly expressed in aorta, stomach, lung and bladder. These two microRNAs were also expressed to a lesser extent in the heart and skeletal muscle (FIG. 1B). In addition, Northern blot analysis for miR-143 and miR-145 in rat aorta vascular smooth muscle cells (RVSMCs) revealed that the expression of these two miRNAs increases during smooth muscle differentiation (FIG. 2), suggesting a potential role for miR-143/145 in this process.

Figure 3:
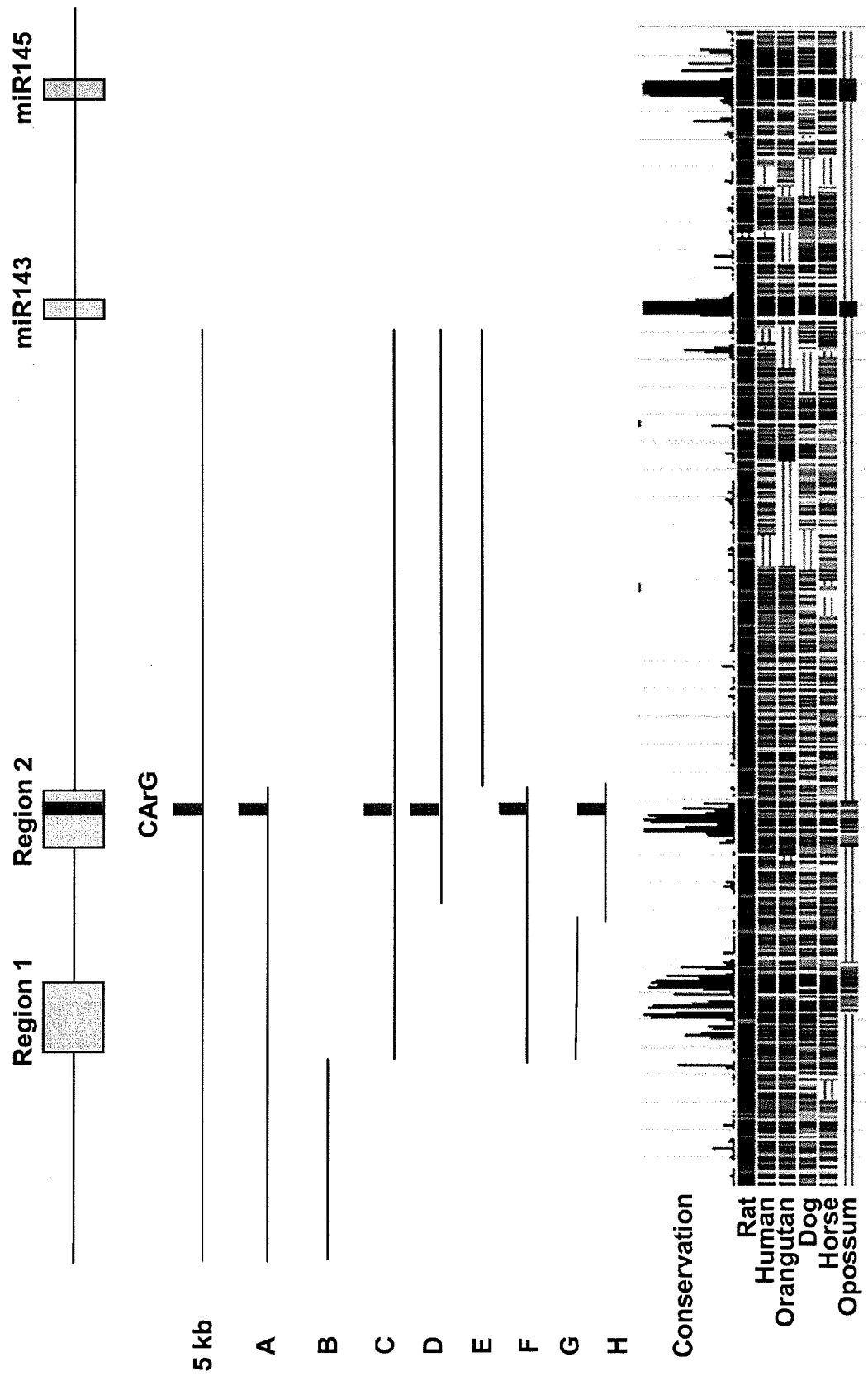
FIG. 3. Diagram depicting evolutionary conservation of miR-143 and miR-145 and upstream regulatory DNA. Location of a conserved SRF binding site (CArG) is highlighted. Various truncations used in constructs to map promoter activity are also shown.

To better understand the transcriptional regulation of miR-143/145, the inventors cloned a 5 kb upstream regulatory region of miR-143/145 into a lacZ reporter vector and generated various truncations of the regulatory region to map promoter activity (FIG. 3). The regulatory region of miR-143/145 contains a conserved serum response factor (SRF) binding site (CArG). Sequences of the regulatory region comprising the conserved CArG site (underlined) for seven different species are shown below:

diation, and baked at 85° C. Blots were hybridized overnight at 39° C. with $^{32}$P-labeled antisense STARFIRE probes directed against the mature sequence of miR-143 or miR-145 (Integrated DNA Technologies). U6 RNA levels were used as a loading control.

Promoter constructs and transgenic mice. Various portions of the 5' upstream region of miR-143/145 were isolated by PCR and cloned upstream of the hsp68 minimal promoter-driven lacZ gene. Transgenic mice harboring various fragments of miR-143/145 regulatory DNA fused to hsp68-lacZ reporter construct were generated as previously reported (Cheng et al., 1992).

Example 2

Myocardin Activates the Regulatory Region of miR-143 and miR-145 Through SRF

To examine the regulation of miR-143/145 at the molecular level, the inventors generated a series of luciferase constructs consisting of truncations of the 5 kb upstream region of miR-143/145 (see FIG. 3), and determined the responsiveness of miR-143/145 regulatory DNA to myocardin in COS cells

```
MOUSE        GGCTCCTGCCCTTATATGGCAAGGCTGCTCTGA    (SEQ ID NO: 1)

RAT          GGCTCCTGTCCTTATATGGCAAGGCTGCTCTGA    (SEQ ID NO: 2)

HUMAN        AGCTCCTTCCCTTATATGGCCAGGCTGCTCTGG    (SEQ ID NO: 3)

ORANGUTAN    GGCTCCTTCCCTTATATGGCCAGGCTGCTCTGG    (SEQ ID NO: 4)

DOG          GGCTCCTTCCCTTATATGGCCAAGCCGCTCCGG    (SEQ ID NO: 5)

HORSE        GGCTCCTTCCCTTATATGGCCAGGCCGCTCTGG    (SEQ ID NO: 6)

OPOSSUM      TGTTCCTTCCCTTATATGGCTATGTAGGTCCAA    (SEQ ID NO: 7)

mutant CArG  CCTTATATTT                           (SEQ ID NO: 8)
```

Figure 4A:
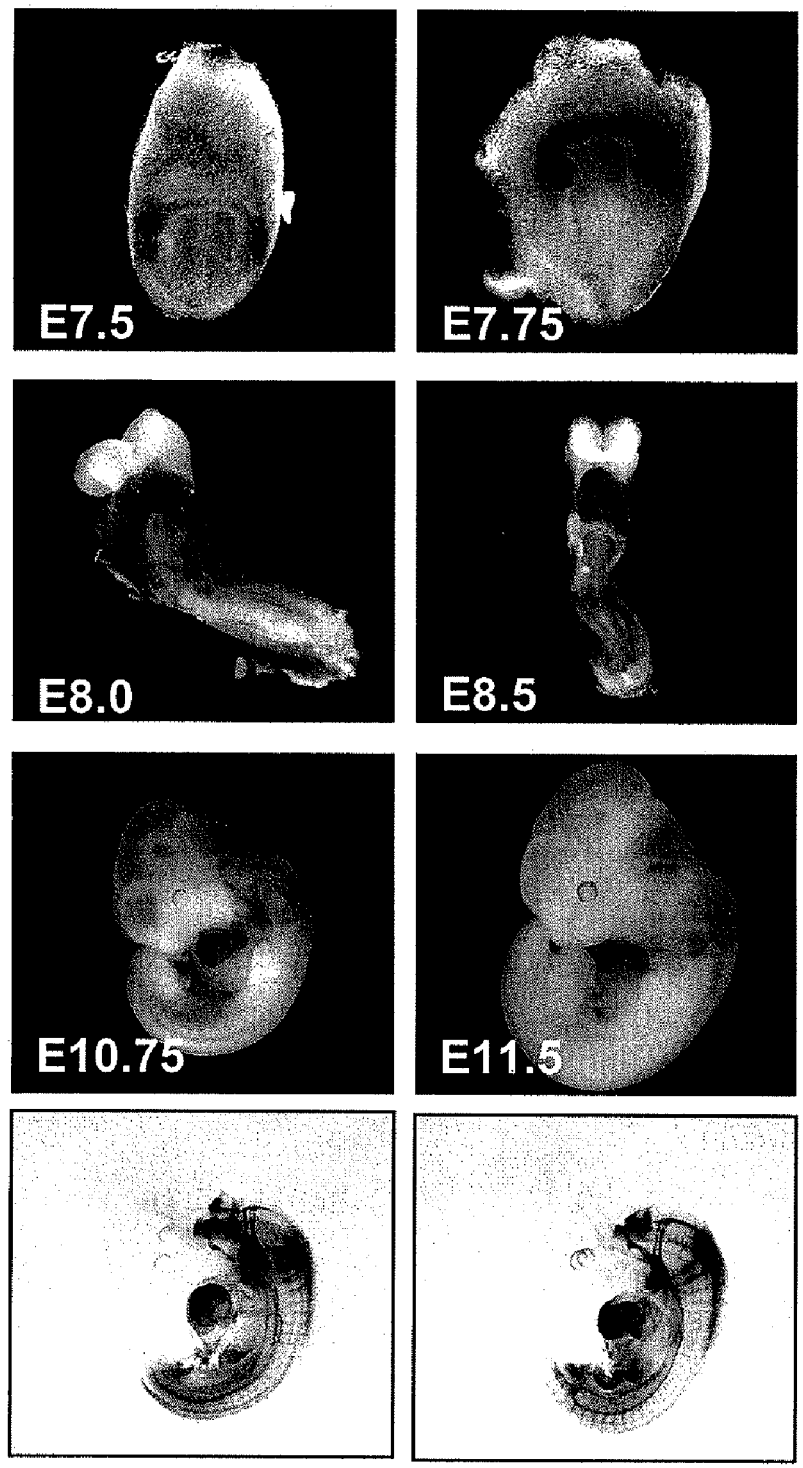
FIG. 4. A. LacZ reporter analysis in transgenic animals demonstrates smooth muscle and cardiac expression is driven by 1.5 kb (construct F) upstream of the miR-143 miR-145 locus. Expression is evident in the cardiac crescent as early as embryonic day 7.5 (E7.5). B. Examination of miR-143/145 regulated βGal expression in adult tissues reveals expression in the heart (Ht) and smooth muscle derivatives. Robust expression is observed in the aorta (Ao), bladder (Bl), and the vessels of the lung (Lu) and skeletal muscle (Sk). C. Mutation of the conserved CArG box abolishes cardiac expression and reduces vascular expression in transgenic animals carrying a mutated lacZ reporter construct (Mut CArG) as compared to wild-type (WT) animals.
Figure 4B:
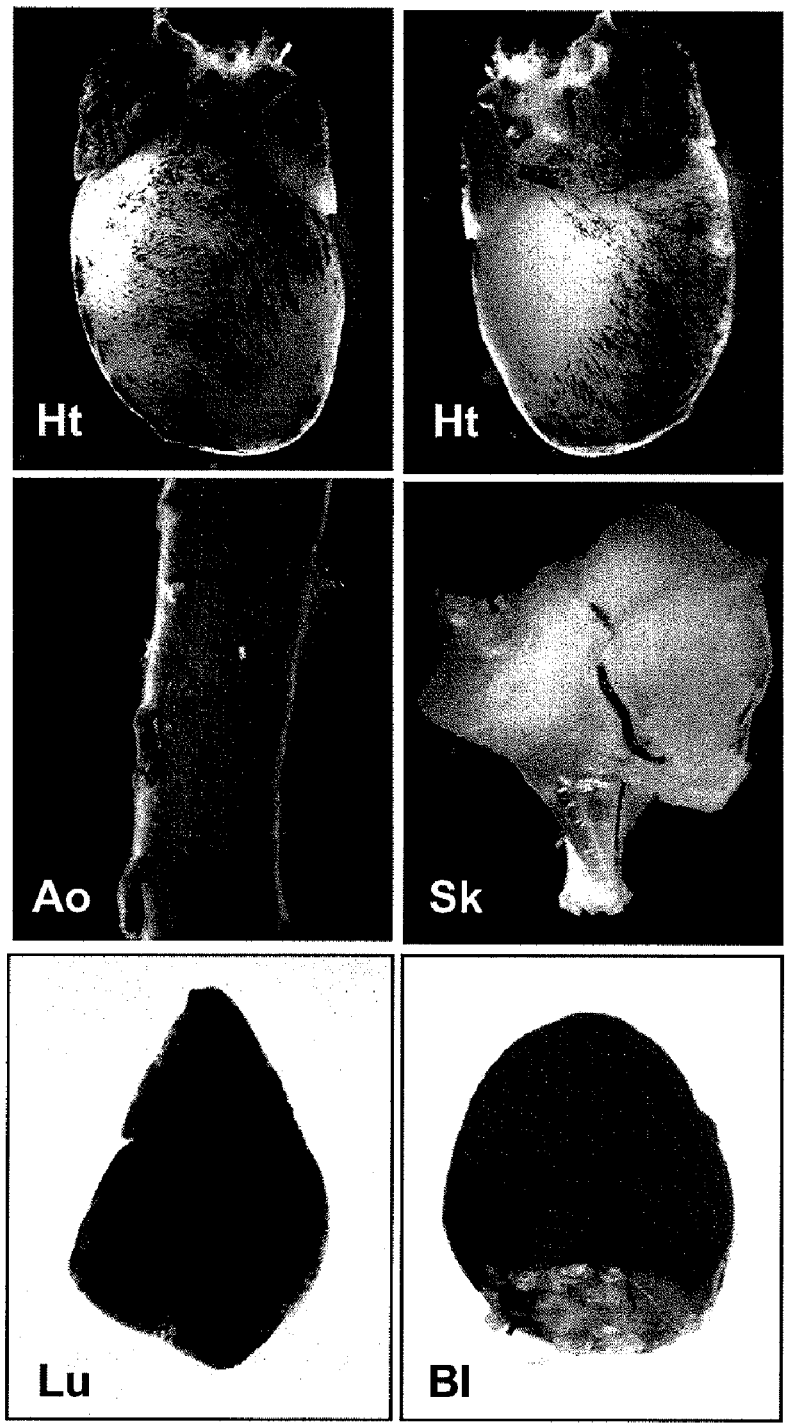
Figure 4C:
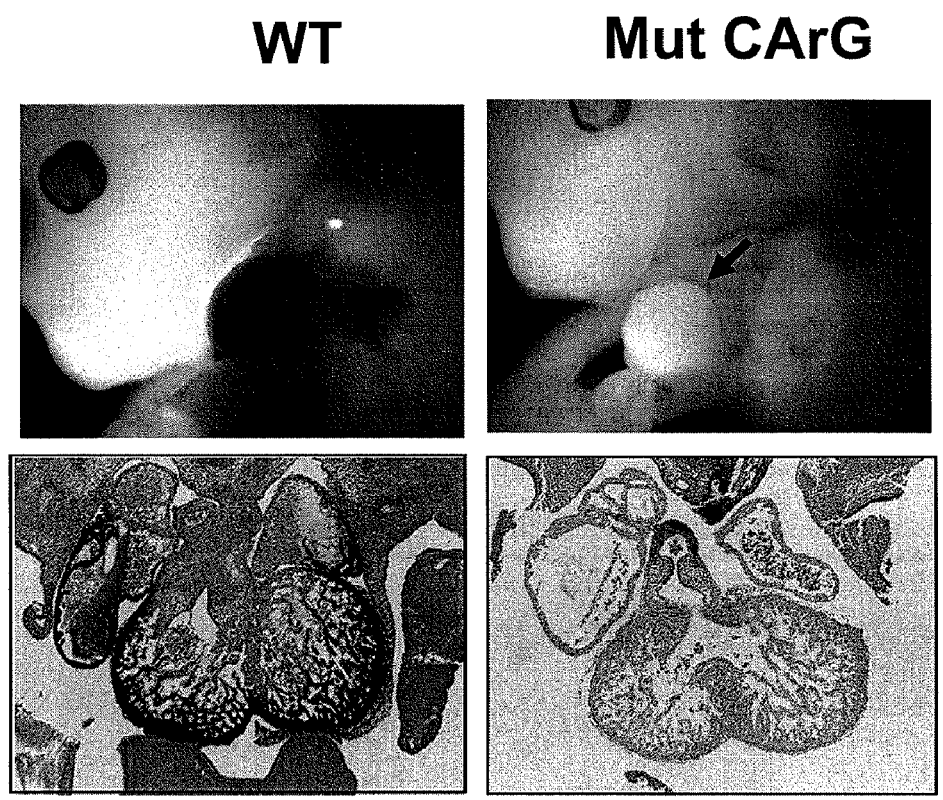

Transgenic embryos harboring a 1.5 kb region upstream of the miR-143/145 locus (construct F in FIG. 3) exhibited expression of the lacZ reporter gene in the cardiac crescent as early as E7.5 (FIG. 4A). LacZ reporter gene expression was observed throughout the heart and in the developing dorsal aorta at E8.0 and E8.5. By E10.75, βGal activity was detected throughout the developing vasculature and the heart. In adults, βGal expression was observed in the heart and smooth muscle tissues (FIG. 4B). Robust expression was observed in the aorta, bladder, and the vessels of the lung and skeletal muscle. Mutation of the conserved CArG box (SEQ ID NO: 8) in the lacZ reporter constructs abolishes cardiac expression and reduces vascular expression (FIG. 4C). These data suggest that SRF and its cofactors including cardiac and smooth muscle transcription factors play important roles in regulating the expression of miR-143/145 in cardiovascular system in vivo.

Specific Methods

RNA purification, microarray analysis and real-time PCR. Total RNA was purified from mouse tissues and cultured cardiomyocytes using Trizol (Invitrogen). Microarray analysis was performed using the mammalian microRNA probe set (LC Sciences). MicroRNA levels were determined using Taq-Man microRNA real time probes (Applied Biosystems).

Figure 5:
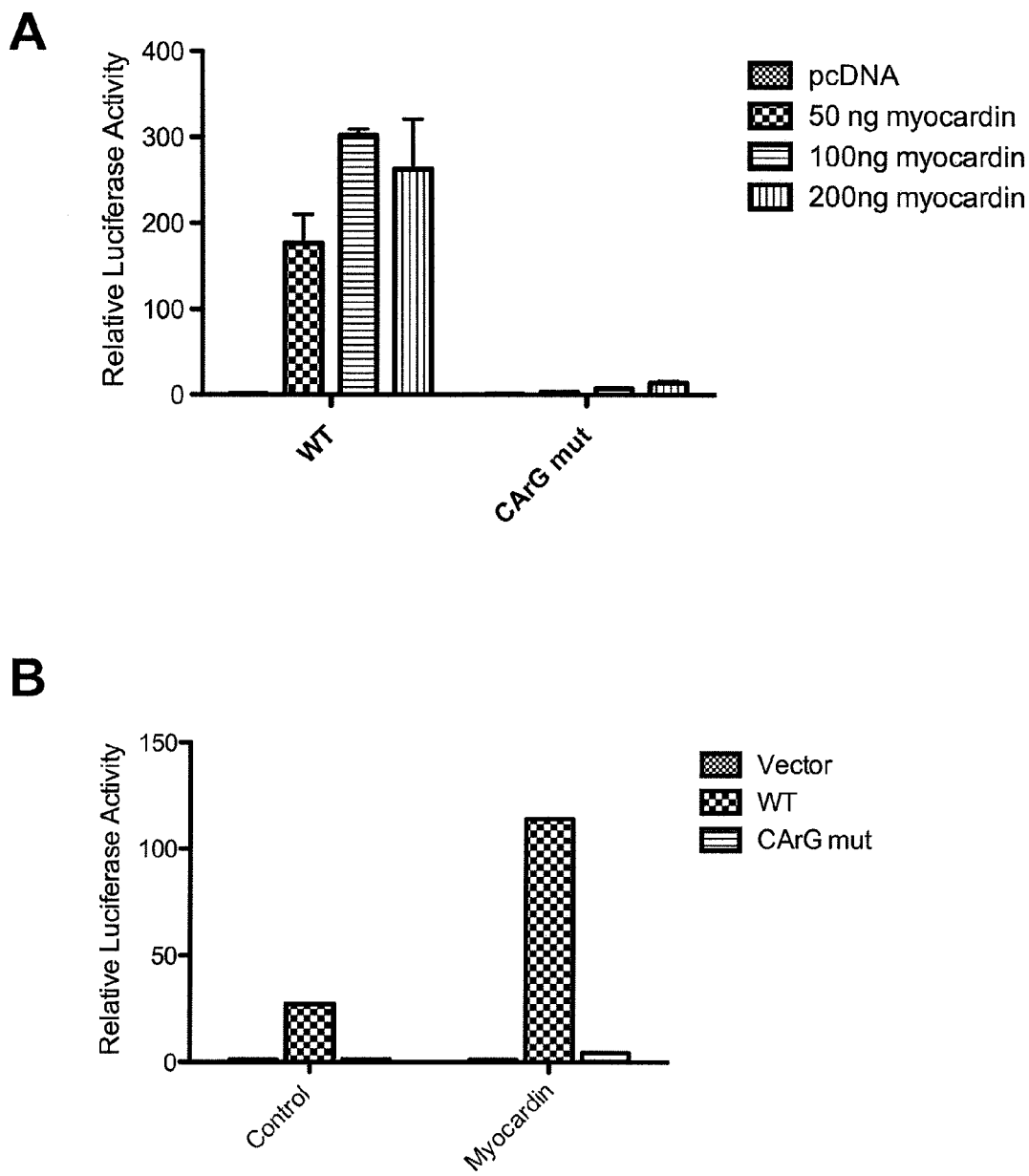
FIG. 5. A. Relative luciferase activities of COS cells co-transfected with myocardin and a 1.5 kb miR143/145 luciferase reporter construct (construct F) having a wild-type (WT) or mutant CArG site (CArG mut). Myocardin activation of the 1.5 kb miR143/145 luciferase reporter is completely dependent on the single conserved CArG box. B. Luciferease reporter gene expression from construct F in neonatal cardiac myocytes demonstrates potent responsiveness and increased activity upon overexpression of myocardin. Reporter gene expression in response to myocardin is significantly reduced by mutation of the CArG site.
Figure 6:
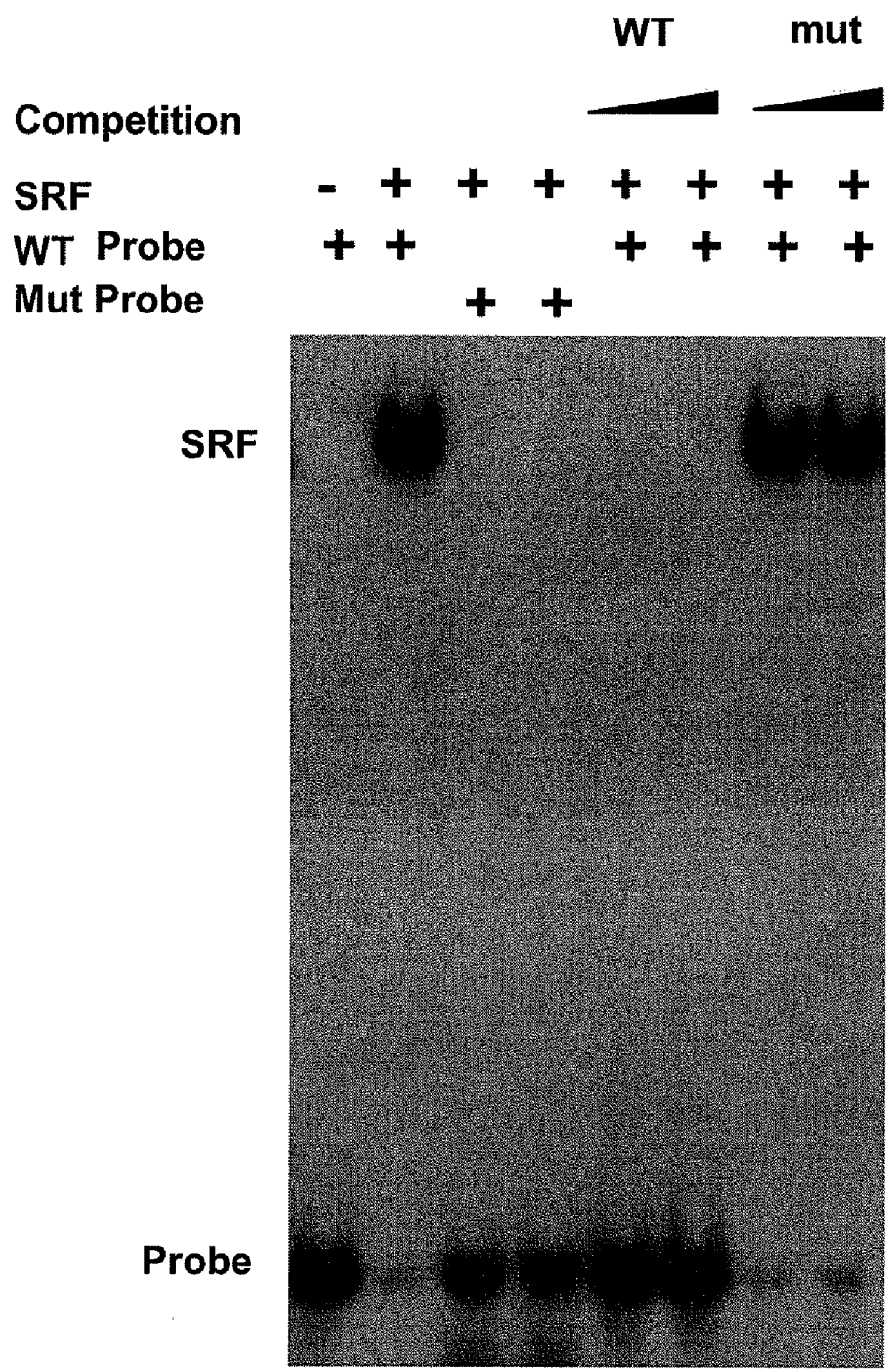
FIG. 6. Serum response factor (SRF) binds to the conserved CArG sequence in the miR-143/145 regulatory DNA as shown by gel shift. Mutant probe fails to bind SRF and cold wild-type oligo effectively competes for SRF binding to the probe. Mutant cold competitor does not abolish gel shift.

Northern Blot. 10 μg of total RNA was loaded onto a denaturing 20% polyacrylamide gel and transferred to a Zetaprobe GT membrane (Bio-Rad), crosslinked by UV irradiation (FIG. 5A). Myocardin activation of the 1.5 kb miR143/145 luciferase reporter (construct F) is completely dependent on the single conserved CArG box, as demonstrated by mutational analysis in transfected COS cells. Luciferase reporter gene expression from construct F in neonatal cardiac myocytes demonstrated potent responsiveness and increased activity upon overexpression of myocardin (FIG. 5B). Myocardin responsiveness of the miR-143/145 luciferase reporter in cardiac myocytes is completely dependent on the single conserved CArG box as shown by the elimination of luciferase expression in FIG. 5B. To determine whether the serum response factor (SRF) could bind to the conserved CArG sequence in the miR-143/145 regulatory region, the inventors performed a gel shift assay. As shown in FIG. 6, SRF bound to the wild-type CArG sequence. However, mutant CArG probe failed to bind SRF and cold wild-type oligos effectively competed for SRF binding to the probe. These results suggest that miR-143/145 expression is regulated by SRF through its interaction with the conserved CArG sequence.

Specific Methods

Cell culture and luciferase assay. COS cells were transfected using Fugene 6.0 (Roche). Various portions of the 5' upstream region of miR-143/145 were isolated by PCR and cloned upstream of the E1b minimal promoter-driven luciferase gene. For miR-143/145 promoter analysis, various miR-143/145-luciferase reporter constructs were transfected with 50 ng, 100 ng, or 200 ng of myocardin. Total DNA was kept constant using empty pcDNA3.1.

Gel Mobility Shift Assay. EMSA was performed largely as previously described (McFadden et al., 2000). Each binding reaction consisted of 3 µl of cell extract from COS cells overexpressing epitope-tagged proteins, as indicated. Extract volume was kept constant with empty pcDNA3.1 transfected lysate. Annealed oligos corresponding to the conserved CArG were used:

```
                                              (SEQ ID NO: 9)
   top strand: 5' ggGCCTTGCCATATAAGGGCAGGA 3'

(SEQ ID NO: 10)
   bottom strand: 5' ggTCCTGCCCTTATATGGCAAGGC 3'
```

(CArG box sequence is underlined). Oligonucleotides were annealed and Klenow labeled as previously described and the DNA-protein complex was resolved on a 6% non-denaturing polyacrylamide gel in 0.5×TBE. Oligos were designed for cold competition and the mutated nucleotides are denoted as lower case.

Example 3

MiR-143 and miR-145 are Down-Regulated after Smooth Muscle Injury

Figure 7:
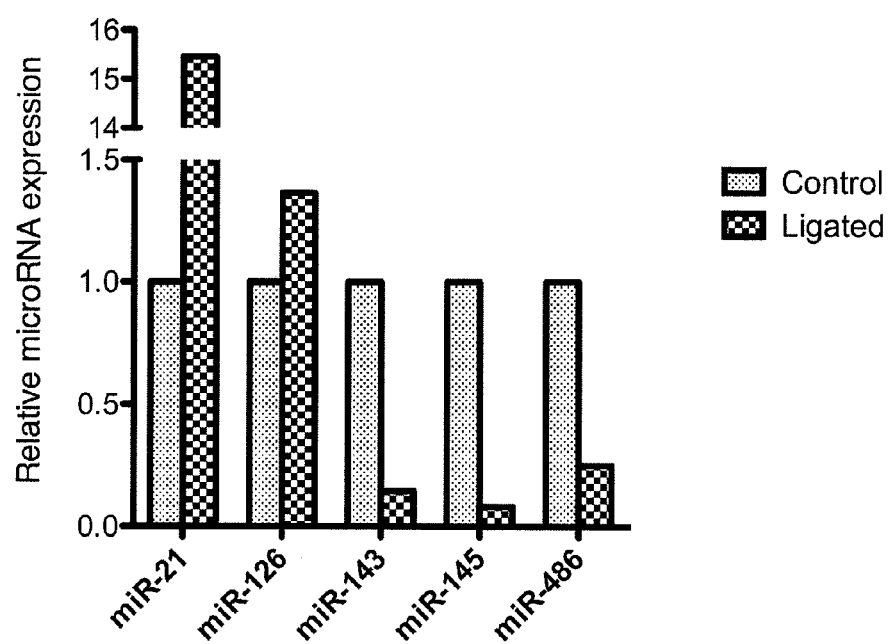
FIG. 7. A. MicroRNA microarray analysis was performed to reveal microRNAs that are altered in a mouse model of phenotypic modulation following smooth muscle injury by carotid artery ligation. MiR-143, miR-145, and miR-486 were all significantly downregulated in the injured carotid artery as compared to unligated control artery. B. Microarray results were validated by Real Time RT-PCR analysis. The expression level of miR-143 and miR-145 was reduced by ~85% and 92%, respectively in the injured carotid artery, while miR-486 was reduced by ~75%. MiR-21 and miR-126 served as positive and negative controls, respectively.

To identify microRNAs that have altered expression after smooth muscle injury, a microRNA microarray analysis was conducted on arterial tissue following smooth muscle injury induced by carotid artery ligation. MiR-143, miR-145, and miR-486 were all significantly downregulated in the injured carotid artery as compared to unligated control artery (FIG. 7A). The microarray results were validated by Real Time RT-PCR analysis. The expression level of miR-143 and miR-145 was reduced by ~85% and 92%, respectively in the injured carotid artery (FIG. 7B). The expression level of miR-486 was reduced by ~75% (FIG. 7B). The expression of miR-21 and miR-126 were used as controls.

Figure 8C:
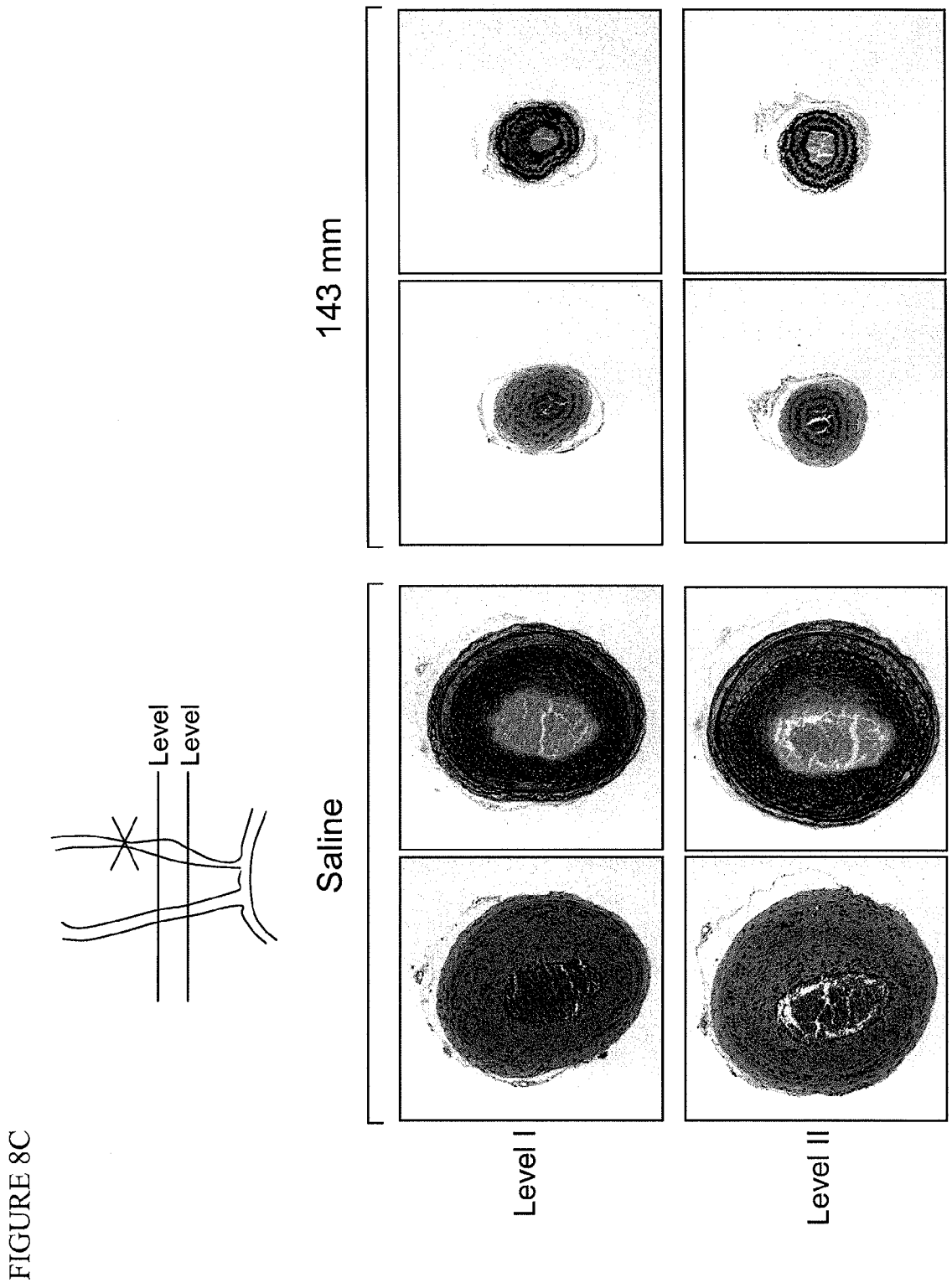
FIG. 8. A. Experimental design for reducing neointima formation following carotid artery ligation by rescuing microRNA levels with miR-143/145 mimic administration. B. The efficacy of miR-mimic (mm) delivery to various tissues was examined by Northern blot 2 days following injection. MiR-143 and miR-145 display significant enrichment in the heart, lung, kidney and liver. C. Histological examination of carotid arteries 28 days after ligation by H&E and elastin staining. Saline-injected control mice display profound neointima formation at all levels examined. Representative histological sections are of Level I (1.5 mm) and Level II (1.9 mm) below the ligature. MiR-143 mimic injected mice displayed a significant reduction in neointima formation at corresponding levels below the ligature.

To examine the potential role of miR-143 and miR-145 in vessel injury, mice were injected via tail vein on two consecutive days with 125 mg/kg of a miR-143 mimic, a miR-145 mimic, or saline. Mimics of the specified miRNAs were double-stranded RNA molecules conjugated to cholesterol that comprised a mature miR-143 or miR-145 sequence. The left carotid artery of each mouse was ligated one day after the second injection (FIG. 8A). Tissue samples of the heart, carotid arteries, lung, liver, and kidney were collected from each animal 28 days following ligation. Northern blot analysis of tissues collected two days after the second injection show that administration of mimics of miR-143 or miR-145 resulted in an overexpression of these two miRs in heart, kidney, liver, and lung, demonstrating effective delivery to these tissues (FIG. 8B). As shown in FIG. 8C, histological examination of carotid arteries 28 days after ligation showed that saline-injected control mice developed profound neointima formation at all levels examined (representative sections taken at Level I (1.5 mm) and Level II (1.9 mm) below the ligature). Mice injected with a miR-143 mimic exhibited a significant reduction in neointima formation at corresponding levels below the ligature. These findings demonstrate that upregulation of miR-143 and miR-145 by administering mimics of the two miRs can reduce neointima formation following vessel injury.

Example 4

MiR-145 Targets Slit-Robo GTPase Activating Protein 1 and 2, Smad3, Sema3, and Cited2

Figure 9A:
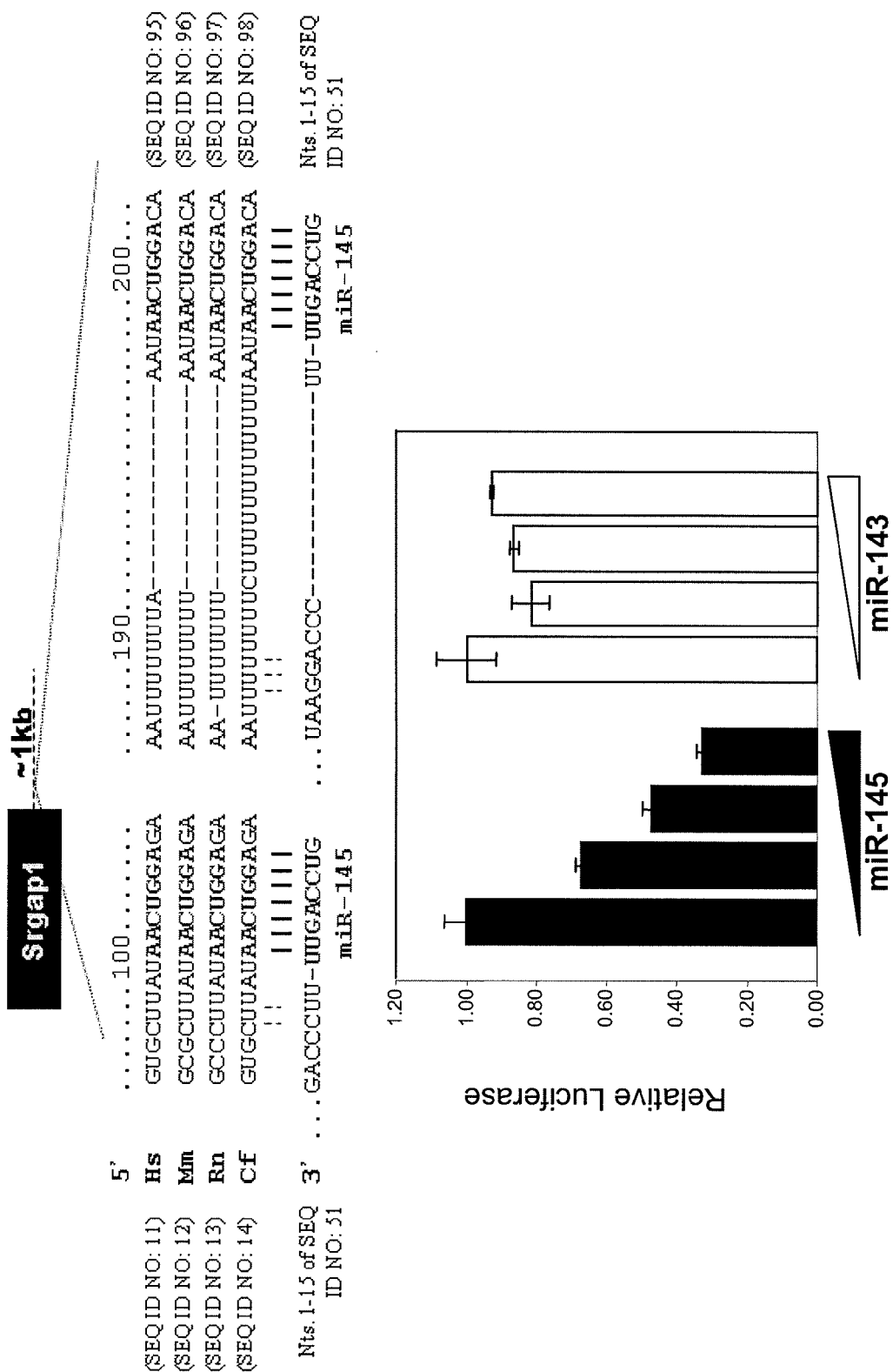
FIG. 9. Predicted targets of miR-143 and miR-145 were identified on TargetScan 5.0. Potential target 3'UTRs were cloned into a CMV-driven luciferase reporter and co-transfected in COS cells with miR-143 or miR-145. MiR-145 repressed the 3'UTRs of Slit-Robo GTPase activating protein 1 (A) and 2 (B) (Srgap), Smad3 (C), Sema3 (D) and Cited2 (E). MiR-145 is also predicted to target KLF5 3'UTR (F). Both miR-143 (G) and miR-145 (H) are predicted to target the MRTFb 3'UTR.
Figure 9B:
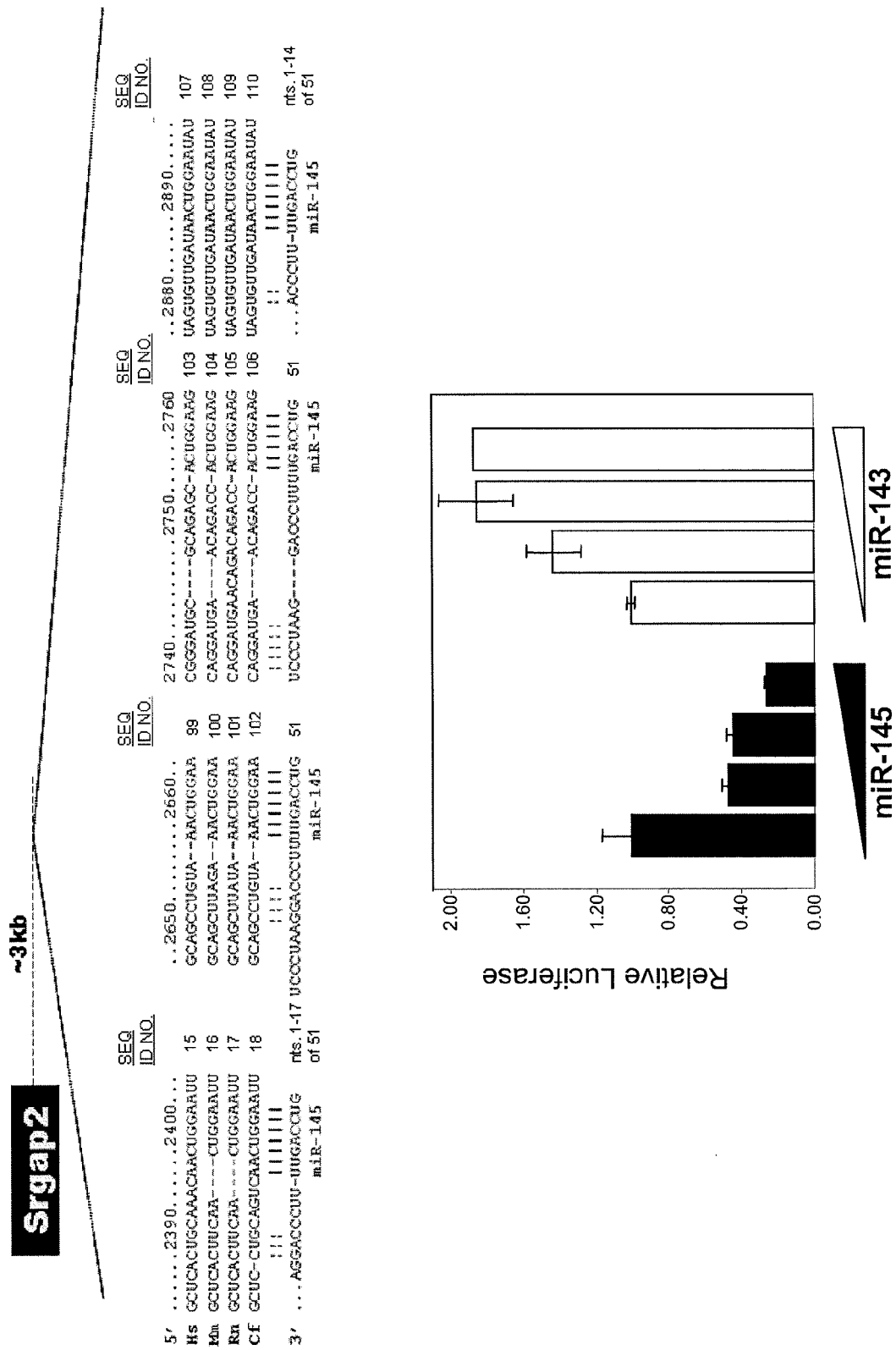

Predicted targets of miR-143 and miR-145 were identified on TargetScan 5.0. The 3' UTRs of potential targets were cloned into a CMV-driven luciferase reporter and co-transfected in COS cells with miR-143 or miR-145. MiR-145 repressed the 3' UTRs of Slit-Robo GTPase activating protein 1 (Srgap1; FIG. 9A), Srgap2 (FIG. 9B), Smad3 (FIG. 9C), Sema3 (FIG. 9D) and Cited2 (FIG. 9E). Expression of miR-143 had no significant effect on luciferase expression from constructs containing the 3' UTRs of these targets. MiR-145 is also predicted to target KLF5 3'UTR (FIG. 9F) and both miR-143 (FIG. 9G) and miR-145 (FIG. 9H) are predicted to target the MRTFb 3'UTR.

Example 5

MRTFa Induces Expression of miR-486 in Cardiomyocytes

To identify additional microRNAs that may play a role in cardiovascular development or disease, the inventors undertook a microRNA microarray analysis designed to select for miRNAs that are induced by the smooth muscle and cardiac-enriched transcription factors, myocardin and MRTFa. Cardiac myocytes were infected with adenovirus directing expression of βgal (control), MRTFa or myocardin. In agreement with previous results, the miR-143/145 cluster was upregulated in cardiomyocytes overexpressing MRTFa. In addition, miR-486 was identified by the miRNA microarray as significantly enriched upon overexpression of MRTFa (FIG. 10A). The induction of miR-486 by MRTFa was independently validated by Northern blot (FIG. 10B). MiR-486 is located in the final intron of the Ank1 gene, which contains an alternative promoter that directs muscle-specific expression. The stem loop structure and mature microRNA are shown in FIG. 10C. Quantitative real time PCR analysis showed significant induction of miR-486 (FIG. 10D) and Ank1 (FIG. 10E) in neonatal cardiac myocytes after 1 day of expressing adenoviral-mediated MRTFa. These data suggest miR-486 is transcribed with the Ank1 gene and is processed as an intronic miRNA.

To determine the tissue distribution of miR-486 in adults, Northern blot analysis was conducted on multiple tissues (FIG. 11A). Expression of miR-486 is enriched in cardiac muscle, skeletal muscle, and smooth muscle-containing tissues. Examination of the expression of the miR-486 host gene, sAnk1, during embryogenesis showed expression in the somites at E11.5 and in the developing skeletal muscle progenitors, tongue, diaphragm, and weakly in the atria and liver (FIG. 11B). Expression is strong specifically in the atria at E17.5, and increases in the atria by P1. Limited expression is also observed in the His bundle branches of the conduction system. By P5, Ank1 expression can be observed in the ventricle and is strongly expressed in both atria and ventricles at adulthood. The in situ hybridization data was confirmed by semi-quantitative RT-PCR analysis of the heart during different embryonic stages (FIG. 11C). In addition, miR-486 expression correlates with skeletal muscle differentiation as demonstrated by increasing expression of miR-486 in differentiating C2C12 cells (FIG. 11D).

To further explore the regulation of miR-486 expression, cardiomyocytes were transfected with increasing concentrations of constructs expressing MRTFa or myocardin. MiR- 486 and Ank1 expression is induced specifically by MRTFa (FIG. 12A). However, myocardin is insufficient to induce miR-486 or Ank1. The regulatory region of the sAnk1 gene contains several putative transcription factor binding sites, including a CArG site, Nkx site, GATA site, and Ebox (FIG. 12B). To better understand the transcriptional regulation of miR-486, the inventors cloned a 1080 bp upstream regulatory region of miR-486 into a lacZ reporter vector. Transgenic embryos harboring a 1080 bp region upstream of the miR-486 locus (1080 bpAnk1-hsp68lacZ) exhibited skeletal muscle specific βgal activity (FIG. 12C). Somite staining is observed at E9.5, and somite and developing skeletal muscle staining is observed at E11.5 and E13.5.

To examine the regulation of miR-486 at the molecular level, the inventors generated luciferase constructs consisting of the 1080 bp upstream region of miR-486 or the 650 bp region of intron 1 (see FIG. 12B), and determined the responsiveness of miR-486 regulatory DNA to MyoD, Nkx2-5, GATA-4, myocardin, or MRTFa in COS cells (FIG. 12D-E). 50 ng, 100 ng and 200 ng of expression plasmids were co-transfected with the luciferase reporter construct. The 1080 bp regulatory region upstream of sAnk1 sequence is activated by MyoD, Nkx2-5 and GATA-4 in COS cells, but not myocardin or MRTFa (FIG. 12D). The 650 bp intron 1 region of sAnk1 is specifically activated by MRTFa, but not myocardin or MRTFb in transiently transfected COS cells (FIG. 12E). Similar results were observed in cardiomyocytes transfected with various luciferase reporters transduced with 10MOI of βgal, myocardin, MRTFa, or Nkx2-5 adenovirus (FIG. 12F). sAnk1 intron-luc was responsive to MRTFa in cardiomyocytes. To further elucidate the regulation of miR-486 expression, mutational analysis of the sAnk1 intron-luciferase reporter constructs was conducted and luciferase expression was measured in COS cells in response to increasing concentrations of MRTFa (FIG. 12G). A 3' truncation or mutation of the distal CArG2 site resulted in loss of luciferase expression.

Specific Methods

RNA purification, microarray analysis and real-time PCR. Total RNA was purified from mouse tissues and cultured cardiomyocytes using Trizol (Invitrogen). Microarray analysis was performed using the mammalian microRNA probe set (LC Sciences). MicroRNA levels were determined using Taq-Man microRNA real time probes (Applied Biosystems).

Northern Blot. 10 µg of total RNA was loaded onto a denaturing 20% polyacrylamide gel and transferred to a Zetaprobe GT membrane (Bio-Rad), crosslinked by UV irradiation, and baked at 85° C. Blots were hybridized overnight at 39° C. with $^{32}$P-labeled antisense STARFIRE probes directed against the mature sequence of miR-486 (Integrated DNA Technologies). U6 RNA levels were used as a loading control.

Transgenic mice. Transgenic mice harboring a hsp68-lacZ reporter construct comprising either the 1080 bp upstream regulatory region of the sAnk1 gene or the 650 bp sAnk1 intron 1 region were generated as previously reported (Cheng et al., 1992).

Example 6

PTEN and Foxo1A are Targets of miR-486

In an attempt to identify potential targets of miR-486 that could play a role in smooth muscle cell phenotypic modulation, the inventors examined predicted targets based on TargetScan 3.0. PTEN (phosphatase and tensin homology located on chromosome 10) is a high quality target of miR-486, containing two 8-mer seed regions conserved among species (FIG. 13A). PTEN is a non-redundant inhibitor of Akt signaling that functions by dephosphorylating PI3Kinase. Further examination of predicted targets for miR-486 by TargetScan 3.0 revealed Foxo1a, the activity of which is inhibited by Akt signaling. Foxo1a also contains a conserved miR-486 binding site (FIG. 13A).

To validate miR-486 targeting of PTEN and Foxo1a, luciferase constructs linked to the 3'UTRs of the PTEN and Foxo1a genes and an artificial miR-486 binding site (sponge) were co-transfected with miR-486 in COS cells. All three reporter constructs exhibited a dose-dependent reduction in luciferase expression with miR-486 expression, suggesting that miR-486 targets these 3' UTR sequences (FIG. 13B).

Next, the inventors examined the endogenous protein levels of PTEN and phospho-Akt in cardiac myocytes overexpressing MRTFa, myocardin or β-Gal. Endogenous PTEN protein levels were reduced in cardiac myocytes upon MRTFa-induced miR-486 overexpression (FIG. 13C). In addition, a corresponding reduction in phosphorylated Akt, which is inhibited by PTEN, was observed. STARS (Striated muscle activator of rho signaling, which activates serum response factor) and MRTFa co-expression result in a more robust repression of PTEN in cardiomyocytes than MRTFa alone. Downstream Akt signaling readouts, phospho-Akt and phospho-GSK3β are synergistically induced upon co-expression of STARS and MRTFa (FIG. 13D).

To further examine the role of miR-486 in the MRTFa-induced downregulation of PTEN, a siRNA approach was adopted to knockdown miR-486. FIG. 13E shows that siRNA-mediated knockdown of miR-486 in cardiac myocytes completely abolished the increase in miR-486 levels in response to MRTFa. Delivery of miR-486 siRNA to cardiomyocytes abrogated the repression of PTEN and Foxo1a and the activation of Akt signaling, suggesting that miR-486 mediates the effects of MRTFa on PTEN and Akt signaling (FIG. 13F). Adenovirus-directed expression of miR-486 in cardiomyocytes resulted in reduction of PTEN protein levels (FIG. 13G). The results from this series of experiments suggest that MRTFa activates Akt survival signaling by inhibiting PTEN via miR-486 induction.

Since miR-486 is highly expressed in the adult heart, and considerable vascular remodeling occurs in the heart after myocardial infarction (MI), the inventors examined the expression of miR-486 after MI. The expression of miR-486 is significantly reduced in the border zone 3 days post myocardial infarction (MI) while expression in remote tissue is unchanged (FIG. 14A). By 14 days post-MI, miR-486 levels are normal in the border zone and increased in remote tissues. To further explore the role of miR-486 in the heart, transgenic mice were generated that overexpress miR-486 under the heart specific αMHC promoter. Northern blot analysis of heart tissue from these transgenic animals showed elevated expression of miR-486 as compared to a non-transgenic littermate (FIG. 14B). MiR-486 transgenic animals exhibited reduced levels of PTEN and increased levels of phospho-Akt in the heart as compared to non-transgenic littermates (FIG. 14C). These results suggest that miR-486 is modulated after cardiac injury and regulates Akt signaling via downregulation of PTEN.

Specific Methods

Myocardial infarction. Myocardial infarction of 12 week-old male mice was performed by ligation of the left coronary artery. RNA was isolated from remote regions of the left ventricle and the border zone of the infarct after 3 days and 2 weeks using Trizol.

Cell culture and luciferase assay. COS cells were transfected using Fugene 6.0 (Roche). For 3' UTR Target assays, 40 ng of pMIR-Report luciferase vector was transfected with increasing amounts of CMV-miR-486 expression vector. Empty CMV expression vector was used as control and to keep total plasmid DNA amounts constant.

Cardiomyocyte cell culture and adenovirus infections. Primary rat cardiomyocytes were prepared as described elsewhere (Molkentin et al., 1998). Forty-eight hours after plating, cells were infected with adenovirus for 3 hours in 10% FBS containing media at 10 MOI MRTFa, 50 MOI STARS or both. βgal adenovirus was used as control. βgal, STARS, and Flag-MRTFa expressing adenoviruses have been previously described (Kuwahara et al., 2005).

Plasmid construction. 3' UTR of the mouse PTEN and Foxo1a genes were amplified and cloned into the SacI/HindIII sites of the pMIR-Report luciferase vector using sequence specific primers. PTEN: For 5'-GGCAATAGGA-CATTGTGTCAG-3' (SEQ ID NO:87), Rev 5'-TGACAA-GAATGAGACTTTAAT-3' (SEQ ID NO:88); Foxo1a: For 5'-GTTAGTGAGCAGGCTACATTT-3' (SEQ ID NO:89), Rev 5'-AAGACTTGGTGCTATGCGCTG-3' (SEQ ID NO:90).

Western blot. Antibodies directed against PTEN, Akt, Akt-phosphoSer473, and phospho-GSK3β (Cell Signaling Technologies) were used to determine protein level by Western blot.

All publications, patents, and patent applications discussed and cited herein are incorporated herein by reference in their entireties. All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The use of the word "a" or "an" when used in conjunction with the term "comprising" in the claims and/or the specification may mean "one," but it is also consistent with the meaning of "one or more," "at least one," and "one or more than one." It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

REFERENCES

The following references, to the extent that they provide exemplary procedural or other details supplementary to those set forth herein, are specifically incorporated herein by reference.

U.S. Pat. No. 6,147,109
U.S. Pat. No. 4,873,191
U.S. Pat. No. 5,844,107
U.S. Pat. No. 5,877,302
U.S. Pat. No. 5,972,900
U.S. Pat. No. 5,972,901
U.S. Pat. No. 5,985,833
U.S. Pat. No. 6,008,336
U.S. Pat. No. 6,060,451
U.S. Pat. No. 6,077,835
U.S. Pat. No. 6,100,237
U.S. Pat. No. 6,174,855
U.S. Pat. No. 6,200,801
U.S. Pat. No. 6,201,006
U.S. Pat. No. 6,232,315
U.S. Pat. No. 6,326,386
U.S. Pat. No. 6,589,286
U.S. Pat. No. 6,682,728
U.S. Pat. No. 6,716,242
U.S. Pat. No. 7,041,127
U.S. Pat. No. 7,048,939
U.S. Pat. No. 7,055,237
U.S. Pat. No. 7,083,642
U.S. Pat. No. 7,087,263
U.S. Pat. No. 7,105,018
U.S. Pat. No. 7,156,869
U.S. Pat. No. 7,232,573
U.S. Pat. No. 7,236,821
U.S. Pat. No. 7,247,313
U.S. Pat. No. 7,273,493
U.S. Pat. No. 7,294,329
U.S. Patent Publn. 20020150626
U.S. Patent Publn. 20030032615
U.S. Patent Publn. 20030203865
U.S. Patent Publn. 20040048787
Abraham et al., *Mol. Med.,* 8:750-760, 2002.
Ambros, *Cell,* 113 (6):673-676, 2003.
Angel et al., *Cell,* 49:729, 1987b.
Angel et al., *Mol. Cell. Biol.,* 7:2256, 1987a.
Atchison and Perry, *Cell,* 46:253, 1986.
Atchison and Perry, *Cell,* 48:121, 1987.
Babak et al., *RNA* 10:1813-1819, 2004.
Baichwal and Sugden, In: *Gene Transfer,* Kucherlapati (Ed.), Plenum Press, NY, 117-148, 1986.
Baldwin and Haddad, *J. Appl. Physiol.,* 90:345-357, 2001.
Banerji et al., *Cell,* 27 (2 Pt 1):299-308, 1981.
Banerji et al., *Cell,* 33 (3):729-740, 1983.
Barad et al., *Genome Res.* 14:2486-2494, 1997.
Barnes et al., *J. Biol. Chem.,* 272 (17):11510-11517, 1997.
Bartel, *Cell,* 116:281-297, 2004.
Benvenisty and Neshif, *Proc. Natl. Acad. Sci. USA,* 83 (24): 9551-9555, 1986.
Berk et al., *J. Clin. Invest.* 117:568-575, 2007.
Berkhout et al., *Cell,* 59:273-282, 1989.
Bhavsar et al., *Genomics,* 35 (1):11-23, 1996.
Blanar et al., *EMBO J,* 8:1139, 1989.
Bock et al., *Nucleic Acids Res.,* 10 (24):8113-8125, 1982.
Bodine and Ley, *EMBO J,* 6:2997, 1987.

Boshart et al., *Cell*, 41:521, 1985.
Bosze et al., *EMBO J*, 5 (7):1615-1623, 1986.
Braddock et al., *Cell*, 58:269, 1989.
Brennecke et al., *Cell*, 113:25-36, 2003.
Brinster et al., *Proc. Natl. Acad. Sci. USA*, 82 (13):4438-4442, 1985.
Bristow, *Cardiology*, 92:3-6, 1999.
Bulla and Siddiqui, *J. Virol.*, 62:1437, 1986.
Calin et al., *Proc. Natl. Acd. Sci. USA*, 99:15524-15529, 2002.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Care et al., *Nat. Med.* 13:613-618, 2007.
Carrington et al. *Science*, 301 (5631):336-338, 2003.
Celander and Haseltine, *J Virology*, 61:269, 1987.
Celander et al., *J Virology*, 62:1314, 1988.
Chandler et al., *Cell*, 33:489, 1983.
Chang and Karin, *Nature*, 410 (6824):37-40, 2001.
Chang et al., *Biochim. Biophys. Acta*, 1092 (2):153-160, 1991.
Chang et al., *Mol. Cell. Biol.*, 9:2153, 1989.
Chang et al., *Nature*, 430 (7001):785-789, 2004.
Chatterjee et al., *Proc. Natl. Acad. Sci. USA*, 86:9114, 1989.
Chen and Okayama, *Mol. Cell. Biol.*, 7 (8):2745-2752, 1987.
Chen et al., *Mol. Cell. Endocrinol.*, 162:45-55, 2000.
Chen et al., *Science*, 303 (5654):83-86, 2004.
Choi et al., *Cell*, 53:519, 1988.
Coffin, In: *Virology*, Fields et al. (Eds.), Raven Press, NY, 1437-1500, 1990.
Cohen et al., *J. Cell. Physiol.*, 5:75, 1987.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J*, 6:3745, 1987.
Culotta and Harner, *Mol. Cell. Biol.*, 9:1376, 1989.
Dandolo et al., *J Virology*, 47:55-64, 1983.
De Villiers et al., *Nature*, 312 (5991):242-246, 1984.
Deschamps et al., *Science*, 230: 1174-1177, 1985.
Dubensky et al., *Proc. Natl. Acad. Sci. USA*, 81:7529-7533, 1984.
Durand et al., *Ann. Med.*, 27:311-317, 1995.
Ebner et al., *Science*, 260: 1344-1348, 1993.
Edbrooke et al., *Mol. Cell. Biol.*, 9:1908, 1989.
Edgerton and Roy, *J Appl. Physiol.*, 89:1224-1231, 2000.
Edlund et al., *Science*, 230:912-916, 1985.
Eichhorn and Bristow, *Circulation*, 94:2285-2296, 1996.
EPO 0273085
Fatkin et al., *J Clin. Invest.*, 106 (11):1351-1359, 2000.
Fechheimer, et al., *Proc Natl. Acad. Sci. USA*, 84:8463-8467, 1987.
Feng and Holland, *Nature*, 334:6178, 1988.
Ferkol et al., *FASEB J.* 7:1081-1091, 1993.
Firak and Subramanian, *Mol. Cell. Biol.*, 6:3667, 1986.
Fitts et al., *J Appl. Physiol.*, 89:823-839, 2000.
Foecking and Hofstetter, *Gene*, 45 (1):101-105, 1986.
Fraley et al., *Proc. Natl. Acad. Sci. USA*, 76:3348-3352, 1979.
Franz et al., *Cardioscience*, 5 (4):235-43, 1994.
Franzen et al., Cell, 75:681-692, 1993.
Frey et al., *Circulation* 109:1580-1589, 2004.
Friedman et al., *Genes Devel.*, 3:1314, 1989.
Fujita et al., *Cell*, 49:357, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Ghosh-Choudhury et al., *EMBO J.* 6:1733-1739, 1987.
Gilles et al., *Cell*, 33:717, 1983.
Gloss et al., *EMBO J.*, 6:3735, 1987.
Godbout et al. *Mol. Cell. Biol.*, 8:1169, 1988.
Gomez-Foix et al., *J. Biol. Chem.*, 267:25129-25134, 1992.
Goodbourn and Maniatis, *Proc. Natl. Acad. Sci. USA*, 85:1447, 1988.
Goodbourn et al., *Cell*, 45:601, 1986.
Gopal, *Mol. Cell. Biol.*, 5:1188-1190, 1985.
Gopal-Srivastava et al., *J. Mol. Cell. Biol.* 15 (12):7081-7090, 1995.
Graham and Prevec, In: *Methods in Molecular Biology: Gene Transfer and Expression Protocol*, Murray (Ed.), Humana Press, Clifton, N.J., 7:109-128, 1991.
Graham and Van Der Eb, *Virology*, 52:456-467, 1973.
Graham et al., *J. Gen. Virl.*, 36 (1):59-74, 1977.
Greene et al., *Immunology Today*, 10:272, 1989
Grishok et al., *Cell*, 106:23-34, 2001.
Grosschedl and Baltimore, *Cell*, 41:885, 1985.
Grunhaus and Horwitz, *Seminar in Virology*, 3:237-252, 1992.
Harland and Weintraub, *J Cell Biol.*, 101 (3):1094-1099, 1985.
Haslinger and Karin, *Proc. Natl. Acad. Sci. USA*, 82:8572, 1985.
Hauber and Cullen, *J Virology*, 62:673, 1988.
Huang, *J Am. Soc. Nephrol.*, 15:1690, 2004.
Huang et al., *Nature*, 384:372-375, 1996.
Hen et al., *Nature*, 321:249, 1986.
Heineke and Molkentin, *Nat. Rev. Mol. Cell. Biol.* 7:589-600, 2006.
Hensel et al., *Lymphokine Res.*, 8:347, 1989.
Hermonat and Muzycska, *Proc. Natl. Acad. Sci. USA*, 81:6466-6470, 1984.
Herr and Clarke, *Cell*, 45:461, 1986.
Hersdorffer et al., *DNA Cell Biol.*, 9:713-723, 1990.
Herz and Gerard, *Proc. Natl. Acad. Sci. USA*, 90:2812-2816, 1993.
Hill et al., *Circulation*, 101:2863-2869, 2000.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Horwich et al. *J. Virol.*, 64:642-650, 1990.
Huang et al., *Cell*, 27:245, 1981.
Huang et al., *Nature*, 384:372-375, 1996.
Hug et al., *Mol. Cell. Biol.*, 8:3065, 1988.
Hutvagner et al., *PLoS Biol.*, 2 (4):E98, 2004.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Ito and Roeder, *Trends Endocrinol. Metab.*, 12:127-134, 2001.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Jones and Shenk, *Cell*, 13:181-188, 1978.
Kadesch and Berg, *Mol. Cell. Biol.*, 6:2593, 1986.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Karlsson et al., *EMBO J*, 5:2377-2385, 1986.
Katinka et al., *Cell*, 20:393, 1980.
Katinka et al., *Nature*, 290:720, 1981.
Kato et al., *J. Biol. Chem.*, 266:3361-3364, 1991.
Kawamoto et al., *Mol. Cell. Biol.*, 8:267, 1988.

Kelly et al., *J. Cell Biol.*, 129 (2):383-396, 1995.
Kiledjian et al., *Mol. Cell. Biol.*, 8:145, 1988.
Kimura et al., *Dev. Growth Differ.* 39 (3):257-265, 1997.
Kinugawa et al., *Circ. Res.*, 89:591-598, 2001.
Kinugawa et al., *J. Clin. Endocrinol. Metab.*, 86:5089-5090, 2001.
Kiriazis and Kranias, *Annu. Rev. Physiol.*, 62:321-351, 2000.
Klamut et al., *Mol. Cell. Biol.*, 10: 193, 1990.
Klein et al., *Nature*, 327:70-73, 1987.
Koch et al., *Mol. Cell. Biol.*, 9:303, 1989.
Krek et al., *Nat. Genet.*, 37:495-500, 2005.
Krek et al., *Nature Genetics*, 37:495-500, 2005.
Krenz and Robbins, *J. Am. Coll. Cardiol.*, 44:2390-2397, 2004.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983a.
Kriegler et al., *Cell*, 38:483, 1984.
Kriegler et al., *Cell*, 53:45, 1988.
Kriegler et al., In: *Gene Expression*, Alan Liss (Ed.), Hamer and Rosenberg, New York, 1983b.
Kriitzfeldt et al., *Nature*, 438:685-689, 2005.
Kuhl et al., *Cell*, 50:1057, 1987.
Kunz et al., *Nucl. Acids Res.*, 17:1121, 1989.
Kuwahara et al., *J Pharmacal. Sci.*, 99 (3):211-213, 2005.
Kuwahara et al., *J Clin. Invest.*, 117 (5):1324-1334, 2007.
Lagos-Quintana et al., *Science*, 294 (5543):853-858, 2001.
LaPointe et al., *Hypertension* 27 (3 Pt 2):715-22, 1996.
LaPointe et al., *J. Biol. Chem.*, 263 (19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Lau et al., *Science*, 294 (5543):858-862, 2001.
Le Gal La Salle et al., *Science*, 259:988-990, 1993.
Lee and Ambros, Science, 294 (5543):862-864, 2001.
Lee et al., *Nature*, 294:228, 1981.
Lee et al., *Nucleic Acids Res.*, 12:4191-206, 1984.
Leung et al., *Proc. Natl. Acad. Sci. USA*, 48:18125-18130, 2006.
Levinson et al., *Nature*, 295:79, 1982.
Levrero et al., *Gene*, 101:195-202, 1991.
Lin et al., *Mol. Cell. Biol.*, 10:850, 1990.
Liu et al., *Proc Natl Acad Sci USA* 101:9740-9744, 2004.
Lowes et al., *J Clin. Invest.*, 100 (9):2315-2324, 1997.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Samow, *Nature*, 353:90-94, 1991.
Majors and Varmus, *Proc. Natl. Acad. Sci. USA*, 80:5866, 1983.
Mann et al., *Cell*, 33:153-159, 1983.
Mansen et al., *Mol. Endocrinol.*, 15:2106-2114, 2001.
Markowitz et al., *J Virol.*, 62:1120-1124, 1988.
McFadden et al., *Development*, 127 (24):5331-5341, 2000.
McNeall et al., *Gene*, 76:81, 1989.
Meister and Tuschl, *Nature*, 431:343-9, 2004.
Miksicek et al., *Cell*, 46:203, 1986.
Molkentin et al., *Cell* 93:215-228, 1998.
Mordacq and Linzer, *Genes and Dev.*, 3:760, 1989.
Moreau et al., *Nucl. Acids Res.*, 9:6047, 1981.
Morkin, *Microsc. Res. Tech.*, 50:522-531, 2000.
Moss et al., *Biol. Chem.*, 271 (49):31688-31694, 1996.
Muesing et al., *Cell*, 48:691, 1987.
Naya et al., *J Biol. Chem.*, 275 (7):4545-4548, 2000.
Ng et al., *Nuc. Acids Res.*, 17:601, 1989.
Nicolas and Rubinstein, In: *Vectors: A survey of molecular cloning vectors and their uses*, Rodriguez and Denhardt (Eds), Stoneham: Butterworth, 494-513, 1988.
Nicolau and Sene, *Biochim. Biophys. Acta*, 721: 185-190, 1982.
Nicolau et al., *Methods Enzymol.*, 149:157-176, 1987.
O'Reilly et al., *Cell*, 79:315-328, 1994.
O'Reilly et al., *Cell*, 88:277-285, 1997.
Ojamaa et al., *Endocrinology*, 141:2139-2144, 2000.
Ondek et al., *EMBO J.*, 6:1017, 1987.
Omitz et al., *Mol. Cell. Biol.*, 7:3466, 1987.
Palmiter et al., *Nature*, 300:611, 1982.
Pantos et al., *Horm. Metab. Res.*, 38:308-313, 2006.
Park et al., *Mol. Cell.*, 19:643-653, 2005.
Paskind et al., *Virology*, 67:242-248, 1975.
Pasquinelli and Ruvkun, *Ann. Rev. Cell Dev. Biol.*, 18:495-513, 2002.
Pavri et al., *Mol. Cell.*, 18:83-96, 2005.
PCT Appln. WO 0071096
PCT Appln. WO 84/03564
PCT Appln. WO 98/33791
Pech et al., *Mol. Cell. Biol.*, 9:396, 1989.
Pelletier and Sonenberg, *Nature*, 334 (6180):320-325, 1988.
Perales et al., *Proc. Natl. Acad. Sci. USA*, 91:4086-4090, 1994.
Perez-Stable and Constantini, *Mol. Cell. Biol.*, 10: 1116, 1990.
Physicians Desk Reference
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Natl. Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9: 169-174, 1995.
Ragot et al., *Nature*, 361:647-650, 1993.
Redondo et al., *Science*, 247:1225, 1990.
Reisman and Rotter, *Mol. Cell. Biol.*, 9:3571, 1989.
Remington's Pharmaceutical Sciences, 15th ed., pages 1035-1038 and 1570-1580, Mack Publishing Company, Easton, Pa., 1980.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Ripe et al., *Mol. Cell. Biol.*, 9:2224, 1989.
Rippe, et al., *Mol. Cell. Biol.*, 10:689-695, 1990.
Rittling et al., *Nuc. Acids Res.*, 17:1619, 1989.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Natl. Acad. Sci. USA*, 86:9079-9083, 1989.
Sakai et al., *Genes and Dev.*, 2: 1144, 1988.
Sambrook and Russell, Molecular Cloning: A Laboratory Manual 3rd Ed., Cold Spring Harbor Laboratory Press, 2001.
Satake et al., *J Virology*, 62:970, 1988.
Schaffner et al., *J. Mol. Biol.*, 201:81, 1988.
Schuyler and Yarbrough, *Basic Res. Cardiol.*, 85:481-494, 1990.
Searle et al., *Mol. Cell. Biol.*, 5:1480, 1985.
Sempere et al., *Genome Biol.*, 5:R13, 2004.
Sharp and Marciniak, *Cell*, 59:229, 1989.
Shaul and Ben-Levy, *EMBO J*, 6:1913, 1987.

Sherman et al., *Mol. Cell. Biol.*, 9:50, 1989.
Shingara et al., *RNA* 11:1461-1470, 2005.
Sleigh and Lockett, *J EMBO*, 4:3831, 1985.
Spalholz et al., *Cell*, 42:183, 1985.
Spandau and Lee, *J Virology*, 62:427, 1988.
Spandidos and Wilkie, *EMBO J.* 2:1193, 1983.
Stephens and Hentschel, *Biochem. J*, 248:1, 1987.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati (Ed.), NY, Plenum Press, 149-188, 1986.
The Merck Index, Eleventh Edition
Thiesen et al., *J Virology*, 62:614, 1988.
Top et al., *J Infect. Dis.*, 124:155-160, 1971.
Treisman, *Cell*, 46 (4):567-174, 1986
Tranche et al., *Mol. Biol. Med.*, 7:173, 1990.
Tronche et al., *Mol. Cell. Biol.*, 9 (11):4759-4766, 1989.
Trudel and Constantini, *Genes and Dev.*, 6:954, 1987.
Tsika et al., *Am. J Physiol. Cell Physiol.*, 283:Cl761-Cl775, 2002.
Tur-Kaspa et al., *Mol. Cell. Biol.*, 6:716-718, 1986.
Tyndell et al., *Nuc. Acids. Res.*, 9:6231, 1981.
Vadaszova et al., *Physiol. Res.* 53 (1):S57-61, 2004.
van Rooij et al., *Proc. Natl. Acad. Sci. USA*, 103 (48):18255-18260, 2006.
Vannice and Levinson, *J Virology*, 62:1305, 1988.
Varmus et al., *Cell*, 25:23-36, 1981.
Vasseur et al., *Proc Natl. Acad. Sci. USA*, 77:1068, 1980.
Wagner et al., *Proc. Natl. Acad. Sci. USA* 87 (9):3410-3414, 1990.
Wang and Calame, *Cell*, 47:241, 1986.
Weber et al., *Cell*, 36:983, 1984.
Wei et al., *J Endocrinol. Invest.*, 28:8-11, 2005.
Weinberger et al. *Mol. Cell. Biol.*, 8:988, 1984.
Winoto and Baltimore, *Cell*, 59:649, 1989.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J Biol. Chem.*, 262:4429-4432, 1987.
Xu et al., *Curr. Biol.*, 13:790-795, 2003.
Yamauchi-Takihara et al., *Proc. Natl. Acad. Sci. USA*, 86 (10):3504-3508, 1989.
Yang and Russell, *Proc. Natl. Acad. Sci. USA*, 87:4144-4148, 1990.
Yang et al., *Nat. Med.* 13:486-491, 2007.
Yao and Eghbali, *Circ. Res.* 71:831-839, 1992.
Young et al., In: *Handbook of Applied Therapeutics*, 7.1-7.12 and 9.1-9.10, 1989.
Yu et al., *Biochem. Biophys. Res. Commun.* 349 (1):59-68. Epub Aug. 11, 2006.
Yutzey et al. *Mol. Cell. Biol.*, 9:1397, 1989.
Zelenin et al., *FEBS Lett.*, 287 (1-2):118-120, 1991.
Zeng et al., *Cancer Res.*, 62 (13):3630-3635, 2002.
Ziober and Kramer, *J Biol. Chem.*, 271 (37):22915-22, 1996.

---

What is claimed is:

1. A method of inhibiting smooth muscle cell proliferation in a subject with a vessel injury comprising contacting a smooth muscle cell at the site of vessel injury with a polynucleotide comprising a sequence of miR-143.

2. The method of claim 1, wherein said polynucleotide comprises a mature sequence of miR-143.

3. The method of claim 2, wherein said polynucleotide comprises a sequence of SEQ ID NO: 38.

4. The method of claim 1, wherein said polynucleotide is formulated in a lipid delivery vehicle.

5. The method of claim 1, wherein said polynucleotide is encoded by an expression vector.

6. The method of claim 1, wherein said subject is a human.

7. A method of inhibiting restenosis or neointima formation in a subject in need thereof comprising administering to the subject a polynucleotide comprising a sequence of miR-143.

8. The method of claim 7, wherein said polynucleotide comprises a mature sequence of miR-143.

9. The method of claim 8, wherein said polynucleotide comprises a sequence of SEQ ID NO: 38.

10. The method of claim 7, wherein said polynucleotide is formulated in a lipid delivery vehicle.

11. The method of claim 7, wherein said polynucleotide is encoded by an expression vector.

12. The method of claim 7, wherein said polynucleotide is administered intraarterially, intravenously, subcutaneously, or sublingually.

13. The method of claim 12, wherein said polynucleotide is administered by a catheter or a coated stent.

14. The method of claim 7, wherein the subject is a human.

15. The method of claim 7, further comprising administering to the subject a second agent that inhibits restenosis or neointima formation.

16. The method of claim 1, wherein said polynucleotide is double stranded.

17. The method of claim 1, wherein said polynucleotide is conjugated to cholesterol.

18. The method of claim 2, wherein said polynucleotide is about 18 to about 25 nucleotides in length.

19. The method of claim 1, wherein said polynucleotide comprises a pri-miRNA or pre-miRNA sequence of miR-143.

20. The method of claim 7, wherein said polynucleotide is double stranded.

21. The method of claim 7, wherein said polynucleotide is conjugated to cholesterol.

22. The method of claim 8, wherein said polynucleotide is about 18 to about 25 nucleotides in length.

23. The method of claim 7, wherein said polynucleotide comprises a pri-miRNA or pre-miRNA sequence of miR-143.

24. The method of claim 15, wherein said second agent is selected from the group consisting of paclitaxel, rapamycin (sirolimus), tacrolimus, zotarolimus, everolimus, docetaxel, pimecrolimus, and derivatives thereof.

25. The method of claim 7, wherein said polynucleotide is administered to the subject following an angioplasty or stenting procedure.

26. A method of inhibiting restenosis or neointima formation in a subject in need thereof comprising administering to the subject a polynucleotide comprising a mature sequence of miR-143.

27. A method of inhibiting restenosis or neointima formation in a subject in need thereof comprising administering to the subject a polynucleotide comprising a mature miR-143 sequence of SEQ ID NO: 38.

28. The method of claim 27, wherein said polynucleotide is formulated in a lipid delivery vehicle.

29. The method of claim 27, wherein the polynucleotide is encoded by an expression vector.

30. The method of claim 27, wherein the polynucleotide is double stranded.

31. The method of claim 27, wherein the polynucleotide is conjugated to cholesterol.

32. The method of claim 27, wherein the polynucleotide is about 18 to about 25 nucleotides in length.

33. A method of inhibiting restenosis or neointima formation in a subject in need thereof comprising administering to the subject a polynucleotide comprising a pri-miRNA or pre-miRNA sequence of miR-143.

34. A method of inhibiting smooth muscle cell proliferation in a subject with a vessel injury comprising contacting a smooth muscle cell at the site of vessel injury with a polynucleotide comprising at least 18-25 consecutive nucleotides of a sequence of miR-143.

35. The method of claim 34, wherein the sequence of miR-143 is SEQ ID NO: 38.

36. A method of inhibiting restenosis or neointima formation in a subject in need thereof comprising administering to the subject a polynucleotide comprising at least 18-25 consecutive nucleotides of a sequence of miR-143.

37. The method of claim 36, wherein the sequence of miR-143 is SEQ ID NO: 38.

* * * * *